United States Patent [19]
Maginot

[11] Patent Number: 6,156,016
[45] Date of Patent: Dec. 5, 2000

[54] CATHETER SYSTEMS AND ASSOCIATED METHODS UTILIZING REMOVABLE INNER CATHETER OR CATHETERS

[75] Inventor: Thomas J. Maginot, Crown Point, Ind.

[73] Assignee: Maginot Vascular Systems, Crown Point, Ind.

[21] Appl. No.: 09/443,877

[22] Filed: Nov. 19, 1999

Related U.S. Application Data

[63] Continuation-in-part of application No. 09/078,834, May 14, 1998, Pat. No. 5,989,213.
[60] Provisional application No. 60/070,583, Jan. 6, 1998.

[51] Int. Cl.$^7$ ....................................................... A61M 5/00
[52] U.S. Cl. .......................... 604/264; 604/523; 604/533; 604/500; 604/508
[58] Field of Search ................................ 604/28, 29, 264, 604/523, 533, 534, 535, 537, 164.01, 164.02, 500, 506, 507, 508

[56] References Cited

U.S. PATENT DOCUMENTS

| | | |
|---|---|---|
| 2,448,232 | 8/1948 | Muse . |
| 4,266,999 | 5/1981 | Baier . |
| 4,468,216 | 8/1984 | Muto . |
| 4,493,696 | 1/1985 | Uldall . |
| 4,738,667 | 4/1988 | Galloway . |
| 4,900,202 | 2/1990 | Weinhold . |
| 5,013,194 | 5/1991 | Weinhold . |
| 5,053,023 | 10/1991 | Martin . |
| 5,156,592 | 10/1992 | Martin et al. . |
| 5,236,424 | 8/1993 | Imran . |
| 5,261,416 | 11/1993 | Taussig . |
| 5,405,320 | 4/1995 | Twardowski et al. . |
| 5,405,323 | 4/1995 | Rogers et al. . |
| 5,417,669 | 5/1995 | Castaneda et al. . |
| 5,470,180 | 11/1995 | Jore . |
| 5,498,240 | 3/1996 | Bagaoisan et al. . |

(List continued on next page.)

OTHER PUBLICATIONS

Marketing brochure entitled "Uldall Double Lumen Hemodialysis Catheter Trays", Cook Critical Care, A Division of of Cook Incorporated, P.O. Box 489, Bloomington, Indiana 47402. 1994.

Interventional Radiology, vol. One, Second Edition, Published by Williams & Wilkins, 428 East Preston Street, Baltimore, Maryland 21202, pp. 366–367; 1992.

Marketing brochure from Micro Therapeutics, Inc. 1062–F Calle Negocio San Clemente, California 92673 Published at least as early as May 13, 1998.

Marketing brochure entitled "Bard Access Systems Hickman: ® Hemodialysis/Plasmapheresis Catheter", Bard Access Systems, Hickman, Groshong, Designs for Life ™, 5425 West Amelia Earhart Drive, Salt Lake City, Utah 84116. Published at least as early as May 13, 1998.

*Primary Examiner*—John D. Yasko
*Attorney, Agent, or Firm*—Paul J. Maginot

[57] ABSTRACT

A catheter system for use in a body of a patient is disclosed. The catheter system includes a guide catheter having a distal guide orifice, a proximal guide orifice, and a guide lumen extending therebetween. The catheter system further includes an original catheter positionable within the guide lumen of the guide catheter, wherein the original catheter has an original lumen and an original distal orifice. In addition, the catheter system includes a replacement catheter positionable within the guide lumen of the guide catheter, wherein the replacement catheter has a replacement lumen and a replacement distal orifice. The catheter system also includes a closure member securable to the guide catheter so as to cover the proximal guide orifice. The original distal orifice is positioned on an original distal segment of the original catheter which extends out of the distal guide orifice of the guide catheter when the original catheter is positioned within the guide lumen of the guide catheter. The replacement distal orifice is positioned on a replacement distal segment of the replacement catheter which extends out of the distal guide orifice of the guide catheter when the replacement catheter is positioned within the guide lumen of the guide catheter. A method of performing a medical procedure with a catheter system is also disclosed.

20 Claims, 26 Drawing Sheets

U.S. PATENT DOCUMENTS

| | | |
|---|---|---|
| 5,514,112 | 5/1996 | Chu et al. . |
| 5,569,182 | 10/1996 | Twardowski et al. . |
| 5,569,204 | 10/1996 | Cramer . |
| 5,591,138 | 1/1997 | Vaillancourt . |
| 5,779,404 | 7/1998 | Jore . |
| 5,971,958 | 10/1999 | Zhang . |

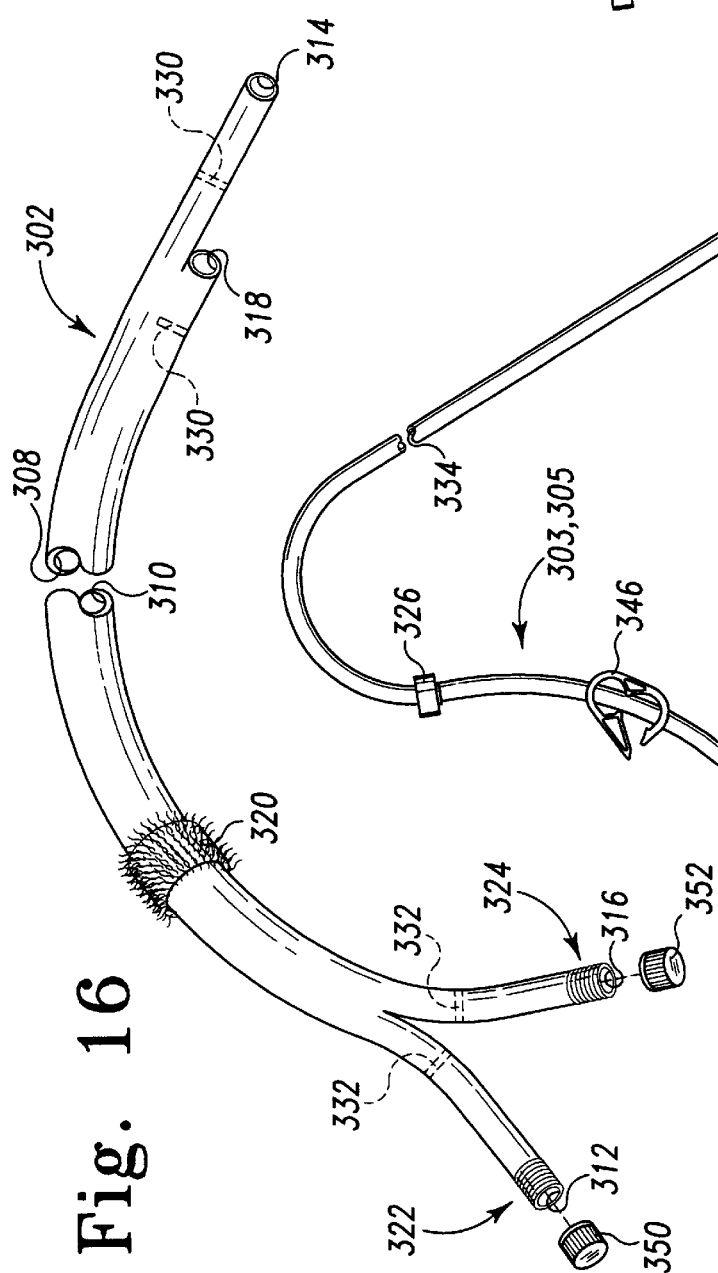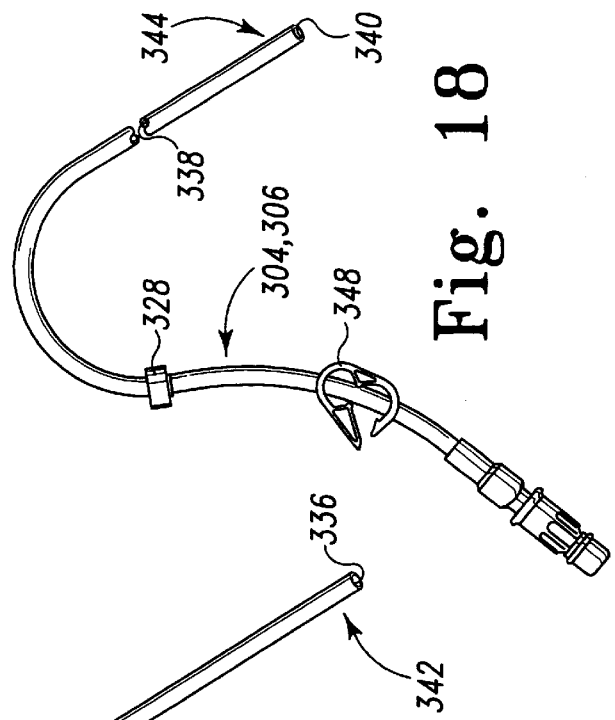
Fig. 16
Fig. 17
Fig. 18

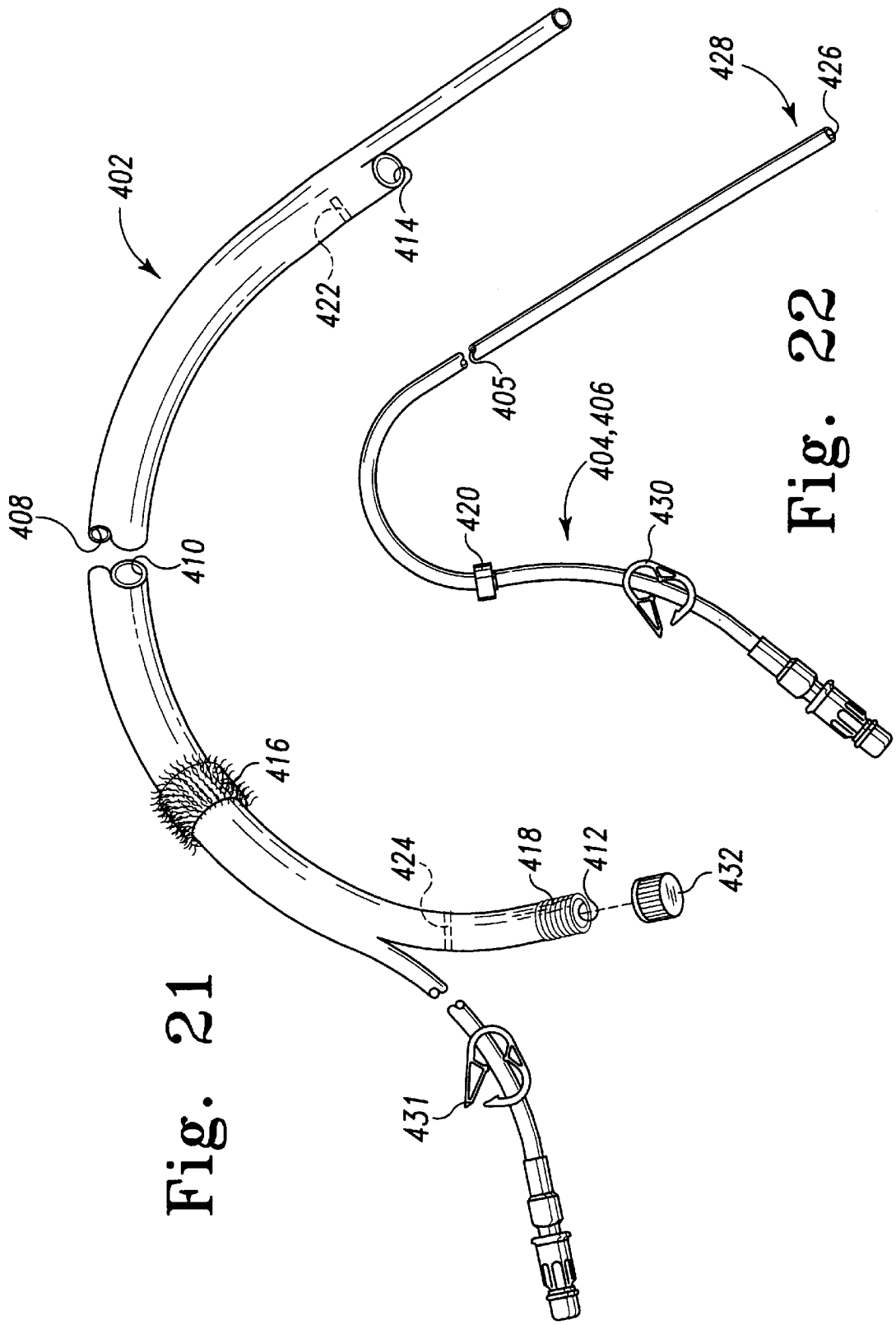

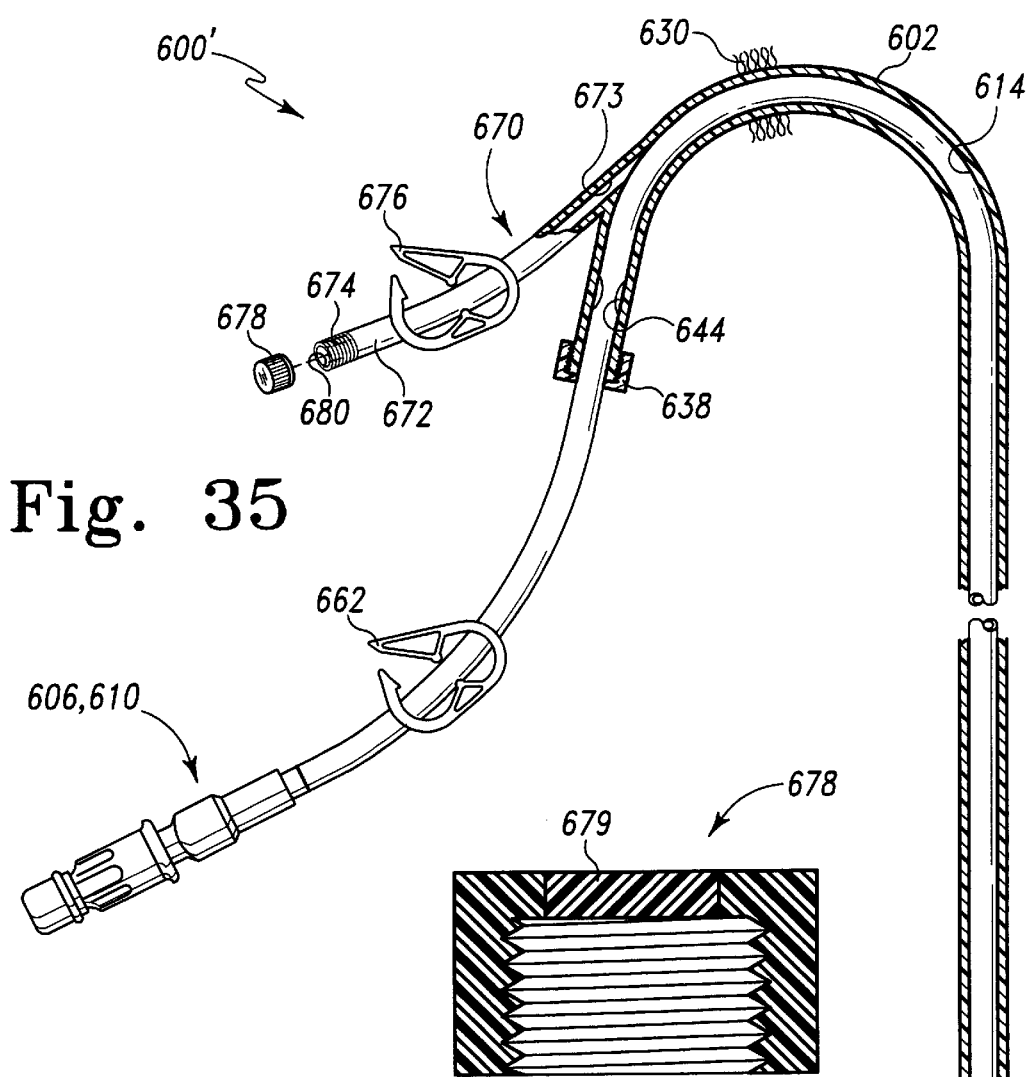
Fig. 35
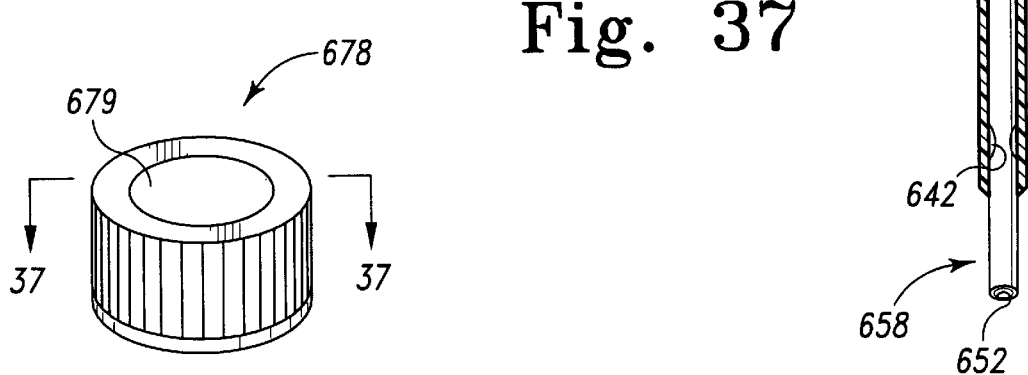
Fig. 37
Fig. 36

CATHETER SYSTEMS AND ASSOCIATED METHODS UTILIZING REMOVABLE INNER CATHETER OR CATHETERS

This application is a continuation-in-part of Application Ser. No. 09/078,834, filed on May 14, 1998 now U.S. Pat. No. 5,989,213, which in turn claims the benefit of U.S. Provisional Application Ser. No. 60/070,583, filed on Jan. 6, 1998.

CROSS REFERENCE

Cross reference is made to co-pending U.S. patent application Ser. No. 09/443,876, entitled "Retractable Catheter Systems and Associated Methods" by Paul J. Maginot and Thomas J. Maginot filed on the same date herewith.

BACKGROUND OF THE INVENTION

The present invention relates generally to catheters, and more particularly to long-term catheter systems, such as long-term dialysis catheter systems, and associated methods of maintaining blood flow in catheter systems.

Various medical procedures require that a patient be catheterized. For example, catheterization may be required when a patient undergoes hemodialysis or has a clot aspirated from a blood vessel. Generally, the length of time the patient will be catheterized dictates whether a physician will utilize a "temporary catheterization technique" (i.e. a technique in which the catheter is left in a blood vessel for a relatively short period of time such as a few minutes, hours, days, or weeks) or a "permanent catheterization technique" (i.e. a technique in which the catheter is left in a blood vessel for a relatively long period of time such as several months or indefinitely).

For example, a procedure in which a clot is aspirated from a blood vessel typically includes placing the catheter in the blood vessel for a relatively short period of time such as a few minutes to a few hours and then withdrawing the catheter once the clot has been removed. Therefore, when performing such an aspiration procedure, it is common for a physician to use the temporary catheterization technique to place the catheter in the blood vessel of the patient.

On the other hand, when a procedure is performed to effect hemodialysis, a physician may place a catheter in the blood vessel for a relatively long period of time. In particular, a patient suffering from kidney failure who is involved in a hemodialysis regimen typically requires a dialysis session three days per week for an indefinite period of time whereby extra fluid, chemicals, and wastes are removed from his/her body. A patient who is involved in such a hemodialysis regimen may need a catheter placed in his/her blood vessel for a relatively long period of time in order to provide a ready means for vascular access into his/her bloodstream over such relatively long period of time. This long term placement of the catheter for dialysis purposes may be desirable for a number of reasons.

Firstly, a patient may have experienced progressive loss of other conventional long term vascular access possibilities such as surgically created arteriovenous fistulas. Accordingly, the long term placement of the catheter in the patient's blood vessel may be the best alternative for the patient as he/she proceeds with the hemodialysis regimen.

Additionally, the long term placement of the catheter in the patient's blood vessel may be desirable after initial creation of an arteriovenous fistula in the patient's body. In particular, it is desirable to provide a ready means for vascular access into the patient's bloodstream during a maturation period of the arteriovenous fistula. The maturation period allows the arteriovenous fistula to develop sufficiently so that it will function as a ready means for vascular access into the patient's bloodstream which may be safely punctured multiple times per week for hemodialysis. The length of time of this maturation period is typically on the order of several weeks (e.g. three weeks) to many months (e.g. six months).

Therefore, when performing a hemodialysis procedure, it is common for a physician to use the permanent catheterization technique to place the catheter in the blood vessel of the patient.

These two catheterization techniques are significantly different with respect to their complexity and degree of invasiveness. For example, in the case of the temporary catheterization technique, it is common to insert a temporary catheter into a patient's blood vessel using a "direct puncture technique." This technique entails creating a small incision in a patient's skin with a scalpel directly over the blood vessel to be catheterized. A needle is then advanced through the skin incision and subcutaneous tissue and into the blood vessel. Thereafter, a guidewire is advanced through the needle into the blood vessel and the needle is subsequerntly removed over the guidewire. Then, one or more tubular vessel dilators are used to widen the opening defined in the skin and subcutaneous tissue, and further to widen the opening defined in the blood vessel wall to a caliber similar to that of the temporary catheter. The temporary catheter is then advanced over the guidewire and into the blood vessel. Thereafter, the guidewire is removed.

When the temporary catheterization technique is used during a clot aspiration procedure, two catheters are usually placed in the blood vessel of a patient. In particular, an outer catheter is usually placed within the blood vessel using the above described direct puncture technique so that its distal opening is located near the clot. Thereafter, an inner catheter having a smaller caliber relative to the outer catheter is advanced through a lumen of the outer catheter. While the inner catheter is positioned within the outer catheter, an aspiration vacuum is applied to the inner catheter with a syringe. If the size of the clot (or fragments thereof) are smaller than the inner diameter of the inner catheter, then the clot or clot fragments are drawn into and through the inner catheter thereby removing the clot from the blood vessel. If the size of the clot or clot fragments are larger than the inner diameter of the inner catheter, then the clot or clot fragments are drawn to a location adjacent to the distal orifice of the inner catheter. Subsequently, while the aspiration vacuum is still being applied, the inner catheter is withdrawn from the outer catheter thereby additionally withdrawing the clot or clot fragments from the outer catheter and the patient's blood vessel. Thereafter, the outer catheter remains temporarily in place within the blood vessel of the patient for subsequent injections of radiographic contrast for imaging purposes to determine the extent of clot remaining in the blood vessel as well as to determine if clot has migrated to another location within the blood vessel. The outer catheter, which remains temporarily in place in the blood vessel, provides a conduit for the inner catheter to be advanced back into the patient's blood vessel for additional aspiration attempts which are usually required for complete removal of the clot from the blood vessel.

If an outer catheter needs to be replaced during a clot aspiration procedure because of catheter malfunction, such replacement can be accomplished by advancing a guidewire through the lumen of the outer catheter and into the blood vessel. The existing outer catheter can then be removed over the guidewire to a location outside of the patient's body. Thereafter, a new outer catheter is placed in the patient's blood vessel by advancing the new outer catheter over the guidewire as discussed above.

In contrast to the temporary catheterization technique, the permanent catheterization technique typically entails inserting a permanent catheter into a patient's blood vessel using a "tunneled catheter technique." The tunneled catheter technique includes (i) creating a first opening by making a small incision in a patient's skin with a scalpel directly over the blood vessel to be catheterized, (ii) puncturing the blood vessel at a location directly below the first opening by advancing a needle through the skin incision and subcutaneous tissue and into the blood vessel, (iii) advancing a guidewire through the needle into the blood vessel, (iv) removing the needle over the guidewire, (v) passing one or more tubular vessel dilators over the guidewire to widen the opening defined in the skin and subcutaneous tissue, and further to widen the opening defined in the blood vessel wall to a caliber similar to that of the tubular guide, (vi) advancing the tubular guide over the guidewire and into the blood vessel, (vii) thereafter, creating a second opening in the patient's skin spaced apart at least several centimeters from the first opening, (viii) advancing a tunneling instrument from the second opening to the first opening so as to create a passageway within the subcutaneous tissue under the skin between the first opening and the second opening, (ix) advancing a permanent catheter having a tissue ingrowth member attached to an outer surface thereof into the second opening and through the passageway such that a distal end of the permanent catheter is located adjacent the first opening, (x) inserting the distal end of the permanent catheter through the tubular guide member and into the blood vessel to be catheterized whereby the tissue ingrowth member is positioned in the subcutaneous tissue, (xi) removing the tubular guide member, and (xii) closing the first opening with suture whereby the permanent catheter (a) is no longer exposed through the first opening, (b) extends for at least several centimeters under the patient's skin between second opening and the location where the permanent catheter enters the blood vessel, and (c) extends out of the second opening so that a proximal end of the permanent catheter is located outside of the patient's body.

In contrast to the direct puncture catheter technique, the tunneled catheter technique results in the placement of a catheter in a patient's body in a manner which allows the catheter to remain safely in the patient's body for a relatively long period of time. For example, a degree of safety is achieved by separating the following two openings by at least several centimeters: (i) the skin opening through which the catheter enters the patient's body, and (ii) the blood vessel opening through which the catheter enters the patient's vascular system. This safety feature decreases the likelihood that bacteria will migrate up the length of the catheter from the skin opening and cause an infection at the blood vessel opening.

In addition, another degree of safety is achieved by providing a tissue ingrowth member which is attached to and extends around an outer surface of the catheter. As the catheter is left in the patient's body over a period of time, the tissue ingrowth member becomes affixed to the subcutaneous tissue of the patient's body thereby providing a secure attachment of the catheter to the patient's body. Providing a secure attachment between the catheter and the patient's body reduces the likelihood that the catheter will be inadvertently removed or withdrawn from the patient's body.

Moreover, since the subcutaneous tissue becomes attached to the tissue ingrowth member, a physical barrier is created between following two openings: (i) the skin opening through which the catheter enters the patient's body, and (ii) the blood vessel opening through which the catheter enters the patient's vascular system. This physical barrier further decreases the likelihood that bacteria will migrate up the length of the catheter from the skin opening and cause an infection at the blood vessel opening.

While the tunneled catheter technique provides the significant advantage of allowing the catheter to remain safely in the patient's body for a relatively long period of time, significant disadvantages of the tunneled catheter technique exists. For example, when a catheter remains in a blood vessel for a long period of time, there is a tendency for blood clots including fibrin (e.g. in the form of a fibrin sheath) to attach to and build-up on the outer and inner surfaces of the portion of the catheter which is located within the blood vessel. The above described attachment and build-up tends to occlude the various distal openings defined in the catheter which enable fluid movement into and out of the catheter. For instance, attempts at withdrawing blood through the catheter may be unsuccessful due to blood clots creating a "ball-valve" effect which occlude the various distal openings of the catheter.

When occlusion of the various distal openings of the catheter occurs due to the above described blood clot attachment and build-up, a physician has several options for eliminating the occlusion thereby reestablishing access to the vascular system. One option is to remove the occluded catheter and replace it with a new catheter. However, in contrast to the ease of exchanging a catheter which was placed in the patient's body using the direct puncture technique, exchanging a catheter which was placed in the patient's body using the tunneled catheter technique is substantially more complicated and invasive. This is true since in order to remove the occluded catheter from the patient's body, the physician must surgically dissect the tissue ingrowth member which is secured to the outer surface of the catheter from the patient's subcutaneous tissue. Recall that the tissue ingrowth member becomes affixed to the subcutaneous tissue over a period of time. Thereafter, the physician would place a new catheter into the patient's body generally using the above described tunneled catheter technique. Thus, this option is undesirable since it requires additional surgery which further traumatizes the patient and increases the cost of the medical care.

Another option for eliminating the occlusion of the various distal openings of the catheter in order to reestablish access to the vascular system involves the performance of a medical procedure in which a blood clot-dissolving medication such as urokinase is infused into the catheter. However, this medication is not always successful in eliminating the occlusion of the various distal openings of the catheter. In addition, infusion of the medication into the catheter subjects the patient to potential bleeding complications due to the medication entering the vascular system and being circulated systemically. Further, this medication is expensive. Thus, this option has serious drawbacks as well.

An additional option for eliminating the occlusion of the various distal openings of the catheter in order to reestablish access to the vascular system involves the performance of a medical procedure in which an intravascular snare is introduced into the blood vessel in order to physically strip off any blood clots or fibrin sheath which has attached and built-up on the distal portion of the catheter. However, for catheters placed in veins, this medical procedure requires a venopuncture in the femoral or jugular vein which is invasive and can be uncomfortable for a patient. Furthermore, this option requires the use of (i) an intravascular snare, (ii) a physician experienced in catheter techniques, and (iii) an angiographic suite to provide fluoroscopic imaging. Use of each of items (i), (ii), and (iii) above causes this option to be relatively expensive. Consequently, this option also has significant disadvantages.

What is needed therefore is a method and apparatus for eliminating the occlusion of the various distal openings of a catheter which has been placed in a patient's body using the tunneled catheter technique which overcomes one or more of the above-mentioned drawbacks.

SUMMARY OF THE INVENTION

In accordance with one embodiment of the present invention, there is provided a catheter system for use in a body of a patient. The catheter system includes a guide catheter having a distal guide orifice, a proximal guide orifice, and a guide lumen extending therebetween. The catheter system further includes an original catheter positionable within the guide lumen of the guide catheter, wherein the original catheter has an original lumen and an original distal orifice. In addition, the catheter system includes a replacement catheter positionable within the guide lumen of the guide catheter, wherein the replacement catheter has a replacement lumen and a replacement distal orifice. Moreover, the catheter system includes a closure member securable to the guide catheter so as to cover the proximal guide orifice. The original distal orifice is positioned on an original distal segment of the original catheter which extends out of the distal guide orifice of the guide catheter when the original catheter is positioned within the guide lumen of the guide catheter. The replacement distal orifice is positioned on a replacement distal segment of the replacement catheter which extends out of the distal guide orifice of the guide catheter when the replacement catheter is positioned within the guide lumen of the guide catheter.

Pursuant to another embodiment of the present invention, there is provided a method of performing a medical procedure with a catheter system which includes (i) a guide catheter having a distal guide orifice, a proximal guide orifice, and a guide lumen extending therebetween, and (ii) an original catheter having an original distal orifice. The method includes the step of positioning the guide catheter within a body of a patient. The method further includes the step of positioning the original catheter within the guide catheter, while the guide catheter is positioned within the body, so that the original distal orifice is advanced through the guide lumen and out of the distal guide orifice, whereby the original distal orifice is positioned outside of the guide lumen. In addition, the method includes the step of performing a first medical procedure on the patient using the original catheter while the original catheter is positioned within the guide catheter and the original distal orifice is positioned outside of the guide lumen. The method also includes the step of removing the original catheter from the guide lumen of the guide catheter after the first medical procedure performing step. Moreover, the method includes the step of attaching a first closure member to the guide catheter so that the first closure member covers the proximal guide orifice of the guide catheter after the original catheter removing step and while the guide catheter is positioned within the body.

It is therefore an object of the present invention to provide a new and useful catheter system and associated method for use in a body of a patient.

It is another object of the present invention to provide an improved catheter system and associated method for use in a body of a patient.

It is yet another object of the present invention to provide a new and useful long-term dialysis catheter system for use in a body of a patient.

It is another object of the present invention to provide an improved long-term dialysis catheter system for use in a body of a patient.

It is a further object of the present invention to provide a new and useful method of maintaining blood flow in a long-term dialysis catheter system.

It is still another object of the present invention to provide an improved method of maintaining blood flow in a long-term dialysis catheter system.

It is yet another object of the present invention to provide a long-term dialysis catheter system and an associated method that does not require additional surgery in order to remove and replace an associated dialysis catheter.

It is moreover another object of the present invention to provide a long-term dialysis catheter system and an associated method which does not require dissection of the tissue ingrowth member of a dialysis catheter in order to remove and replace an associated dialysis catheter.

It is additionally another object of the present invention to provide a long-term dialysis catheter system and an associated method which is relatively less invasive in order to remove and replace an associated dialysis catheter.

It is further another object of the present invention to provide a long-term dialysis catheter system and an associated method which is relatively less expensive in order to remove and replace an associated dialysis catheter.

It is moreover another object of the present invention to provide a long-term dialysis catheter system and an associated method which is relatively safer in order to remove and replace an associated dialysis catheter.

It is yet another object of the present invention to provide a long-term dialysis catheter system and an associated method which is relatively less complicated in order to remove and replace an associated dialysis catheter.

It is further another object of the present invention to provide a long-term dialysis catheter system and an associated method which is relatively less traumatic in order to remove and replace an associated dialysis catheter.

It is still another object of the present invention to provide a long-term dialysis catheter system and an associated method which does not require the infusion of a clot-dissolving medication such as urokinase into the patent's body in order to reestablish an appropriate level of fluid flow in an associated dialysis catheter.

It is yet another object of the present invention to provide a long-term dialysis catheter system and an associated method which does not require the use of an intravascular snare in order to reestablish an appropriate level of fluid flow in an associated dialysis catheter.

It is moreover another object of the present invention to provide a long-term dialysis catheter system and an associated method which does not require use of an angiographic suite in order to reestablish an appropriate level of fluid flow in an associated dialysis catheter.

It is still another object of the present invention to provide a long-term dialysis catheter system and an associated method which does not require use of fluoroscopic imaging in order to reestablish an appropriate level of fluid flow in an associated dialysis catheter.

It is additionally another object of the present invention to provide a long-term dialysis catheter system and an associated method which does not require blood clot to be stripped off of the catheter with an intravascular snare in order to reestablish an appropriate level of fluid flow in an associated dialysis catheter.

It is further another object of the present invention to provide a long-term dialysis catheter system and an associated method that does not involve a medical procedure which requires the patient to be subjected to a venopuncture in the femoral or jugular vein in order reestablish an appropriate level of fluid flow in an associated dialysis catheter.

Other objects and benefits of the present invention can be discerned from the following description and accompanying drawings.

BRIEF DESCRIPTION OF THE DRAWINGS

FIG. 16 is a side elevational view of the guide catheter of the catheter system shown in FIG. 15;

FIG. 17 is a side elevational view of the first original catheter of the catheter system shown in FIG. 15;

FIG. 18 is a side elevational view of the second original catheter of the catheter system shown in FIG. 15;

FIG. 21 is a side elevational view of the guide catheter of the catheter system shown in FIG. 20;

FIG. 22 is a side elevational view of the original catheter of the catheter system shown in FIG. 20;

FIG. 35 is a view similar to FIG. 31, but showing another catheter system which incorporates the features of the present invention therein;

FIG. 36 is an enlarged perspective view of the closure member of FIG. 35;

FIG. 37 is an enlarged cross sectional view of the closure member of FIG. 36 taken along the line 37—37 of FIG. 36 as viewed in the direction of the arrows.

DESCRIPTION OF THE PREFERRED EMBODIMENTS

Figure 1:
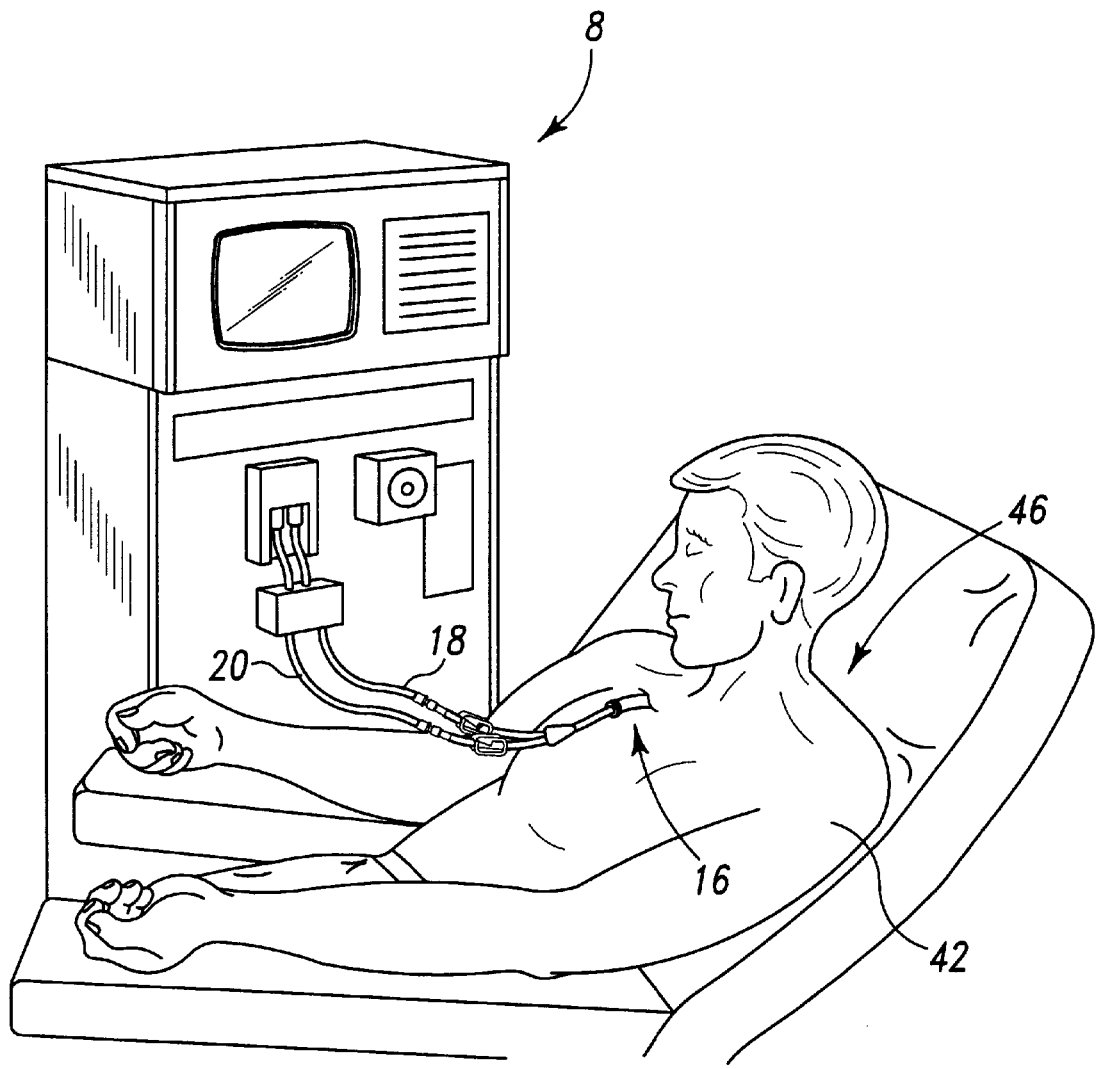
FIG. 1 is a perspective view of a patient undergoing a dialysis procedure utilizing the long-term dialysis catheter system of the present invention.

While the invention is susceptible to various modifications and alternative forms, specific embodiments thereof have been shown by way of example in the drawings and will herein be described in detail. It should be understood, however, that there is no intent to limit the invention to the particular form disclosed, but on the contrary, the intention is to cover all modifications, equivalents, and alternatives failing within the spirit and scope of the invention as defined by the appended claims.

I. Catheter System 16

Referring now to FIG. 1, there is shown a hemodialysis machine 8 to which is attached a long-term dialysis catheter system 16 which incorporates the features of a first embodiment of the present invention therein. The catheter system 16 is inserted in a patient's body 46. The hemodialysis machine 8 includes an inlet line 18 and an outlet line 20 which are each in fluid communication with the catheter system 16. The body 46 includes skin, generally indicated by the reference numeral 42. The body 46 further includes subcutaneous tissue 44 positioned below the skin 42 (see FIG. 7).

Figure 2:
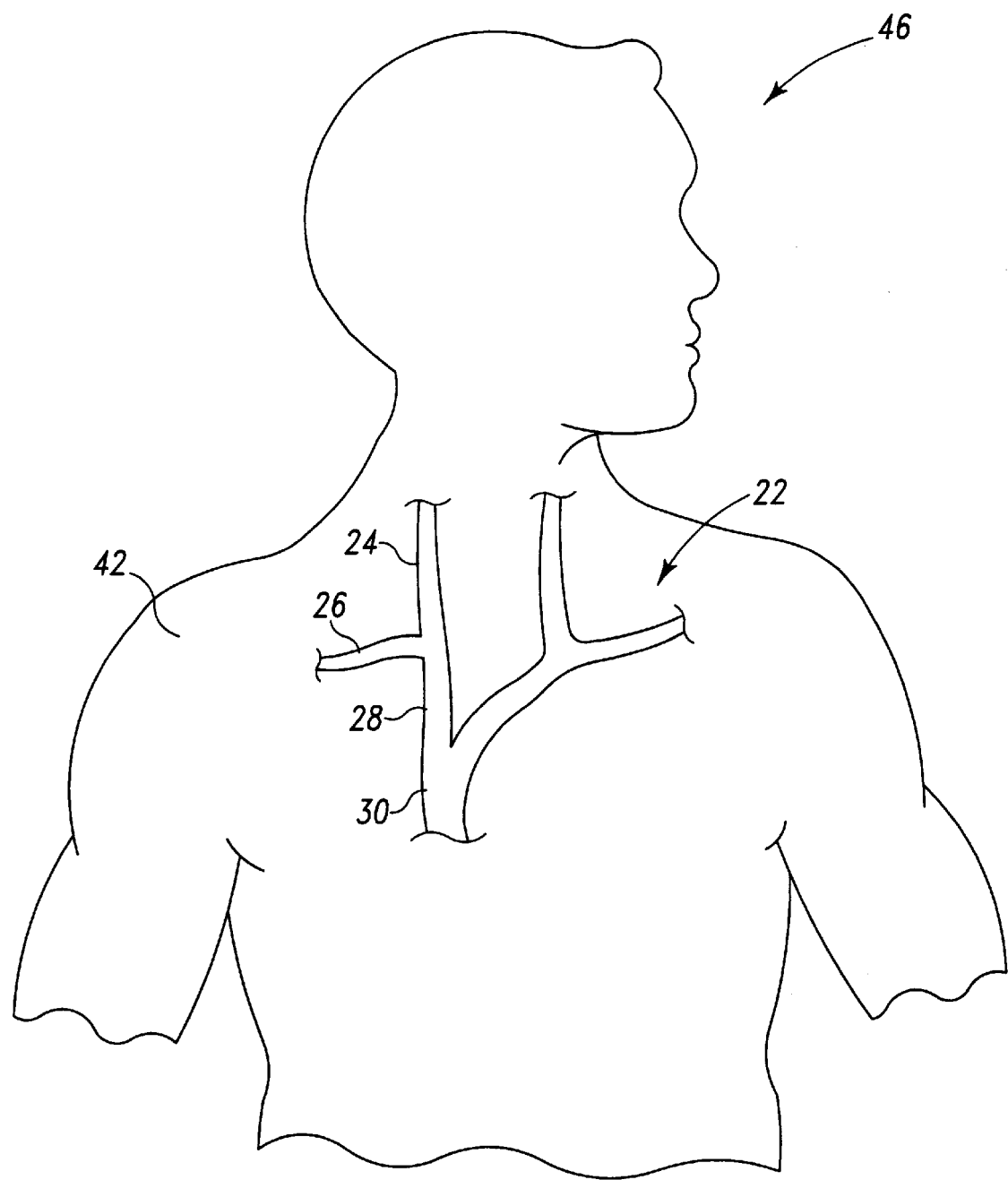
FIG. 2 is a schematic view of a portion of the vascular system of the patient of FIG. 1, showing the right internal jugular vein, the right subclavian vein, the right innominate vein, and the superior vena cava.

As shown in FIG. 2, the body 46 further includes a vascular system 22. The vascular system 22 includes a right internal jugular vein 24, a right subclavian vein 26, a right innominate vein 28, and a superior vena cava 30. Note that the vascular system 22 is positioned within the body 46 underneath the skin 42. However, the vascular system 22, including the right internal jugular vein 24, the right subclavian vein 26, the right innominate vein 28, and the superior vena cava 30, are depicted in FIGS. 2 and 7–10 (and also in FIGS. 11, 30, 34 and 38) with solid lines for clarity of description.

Figure 3:
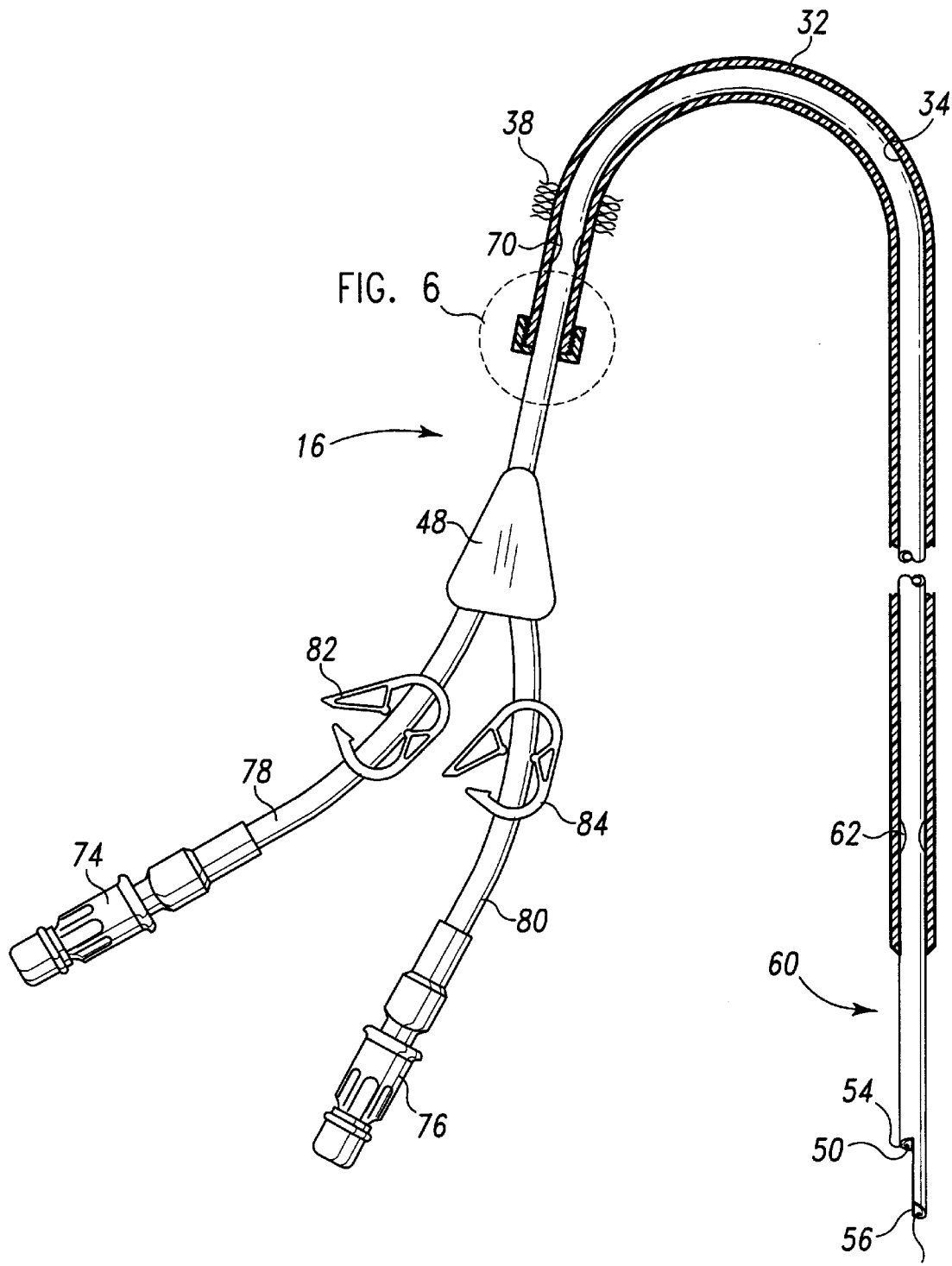
FIG. 3 is an enlarged side elevational view of the long-term dialysis catheter system of FIG. 1, showing the original dialysis catheter positioned within the guide lumen of the guide catheter.

The catheter system 16 is shown in more detail in FIG. 3. In particular, the catheter system includes a guide catheter 32 having a guide lumen 34 which extends the entire length thereof (see also FIGS. 4A–4D). The guide lumen 34 defines a proximal guide orifice 35 and a distal guide orifice 36.

Figure 4A:
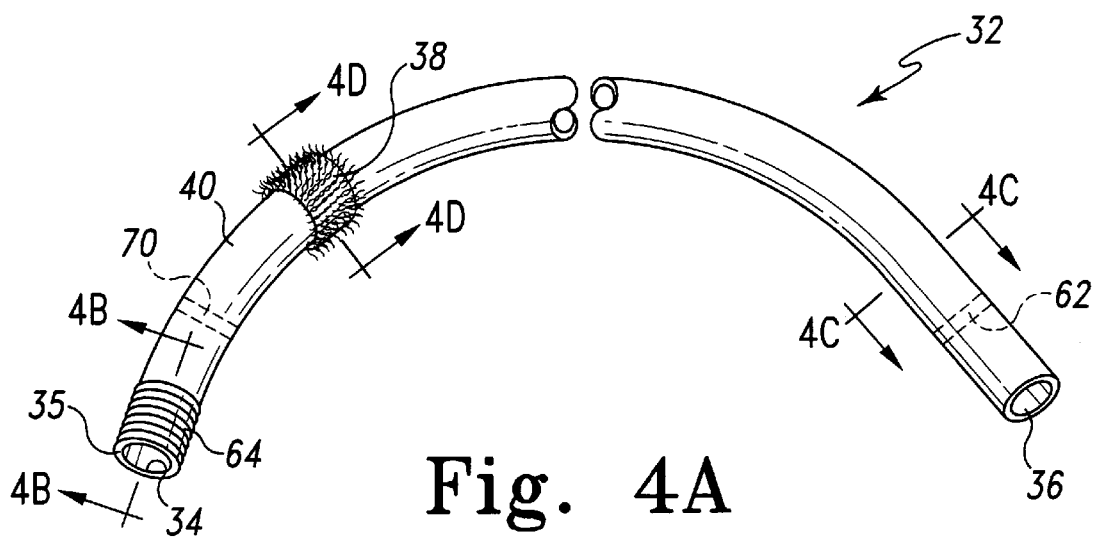
FIG. 4A is an enlarged side elevational view of the guide catheter of the long-term dialysis catheter system shown in FIG. 1.
Figure 4B:
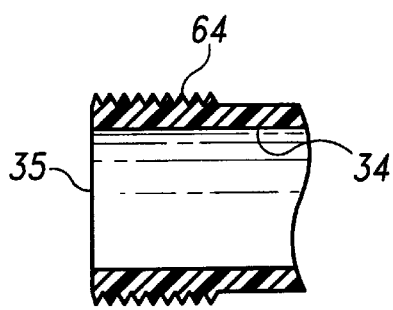
FIG. 4B is an enlarged fragmentary cross sectional view of the guide catheter taken along the line 4B—4B of FIG. 4A as viewed in the direction of the arrows.
Figure 4C:
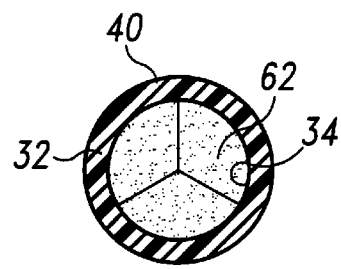
FIG. 4C is an enlarged cross sectional view of the guide catheter taken along the line 4C—4C of FIG. 4A as viewed in the direction of the arrows.
Figure 4D:
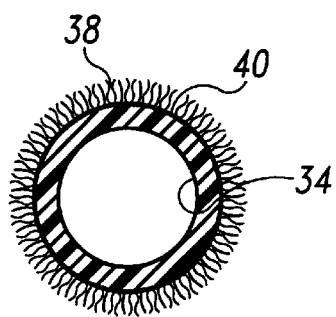
FIG. 4D is an enlarged cross sectional view of the guide catheter taken along the line 4D—4D of FIG. 4A as viewed in the direction of the arrows.

The catheter system 16 further includes a dialysis catheter 48 which is able to be positioned within the guide lumen 34 of the guide catheter 32 (see FIG. 4A). In addition, the catheter system 16 includes a dialysis catheter 58 which is also able to be positioned within the guide lumen 34 of the guide catheter 32 (see FIG. 10). In particular, according to one preferred manner of using the catheter system 16 during a dialysis session, the dialysis catheter 48 is positioned within the guide lumen 34 of the guide catheter 32 for a period of time during which blood is infused and withdrawn therethrough. After the period of time, the blood flow through the lumens of the dialysis catheter 48 may become partially or even totally inhibited due to blood clot build-up. In order to remedy this problem, the dialysis catheter 48 is withdrawn from the guide lumen 34 of the guide catheter 32, and thereafter, the dialysis catheter 58 is positioned within the guide lumen 34 of the guide catheter 32 for a subsequent period of time during which blood is infused and withdrawn therethrough. Since the dialysis catheter 48 is originally used in the catheter system 16 and thereafter replaced with the dialysis catheter 58, the dialysis catheter 48 may be characterized as an "original catheter" and the dialysis catheter 58 may be characterized as a "replacement catheter".

Referring again to FIGS. 4A–4D, the guide catheter 32 also includes an outer surface 40 having a tissue ingrowth member 38 secured thereto. Tissue ingrowth member 38 is configured to facilitate fibrous tissue growth therein. More specifically, the subcutaneous tissue 44 of body 46 becomes affixed to the tissue ingrowth member 38 when the tissue ingrowth member 38 remains in contact with the subcutaneous tissue 44 over a period of time. One type of tissue ingrowth member which may be used as the tissue ingrowth member 38 is a DACRON cuff which is available from Bard Access Systems of Salt Lake City, Utah.

The guide catheter 32 further includes a first locking component 64 defined on a proximal end portion thereof. The first locking component 64 includes external threads which cooperate with an internally threaded cap 67 of dialysis catheter 48 to lock the dialysis catheter 48 to the guide catheter 32 as will be discussed in more detail below.

The guide catheter 32 further includes a distal blood flow valve 62 and a proximal blood flow valve 70 positioned within the guide lumen 34. The blood flow valves 62 and 70 are configured to prevent fluid communication between the proximal guide orifice 35 and the distal guide orifice 36 through the guide lumen 34 when neither the dialysis catheter 48 nor the dialysis catheter 58 are positioned within the guide lumen 34. In addition, when either the dialysis catheter 48 or the dialysis catheter 58 is positioned within the guide lumen 34, the blood flow valves 62 and 70 function to prevent blood and/or air leakage through a space defined between the outer surface of the dialysis catheter 48, 58 and the inner surface of the guide catheter 32.

One valve which may be used as either the distal blood flow valve 62 or the proximal blood flow valve 70 with some minor modifications is available from Micro Therapeutics, Inc. of San Clemente, Calif. under the trademark "Cragg MicroValve™".

Referring now to FIGS. 5A–5D, the dialysis catheter 48 includes an ingress lumen 50 and an egress lumen 52 defined therein. The ingress lumen 50 defines a distal ingress orifice 54. Similarly, the egress lumen 52 defines a distal egress orifice 56. The distal ingress orifice 54 and the distal egress orifice 56 are defined in a distal segment 60 of the dialysis catheter 48.

Figure 6:
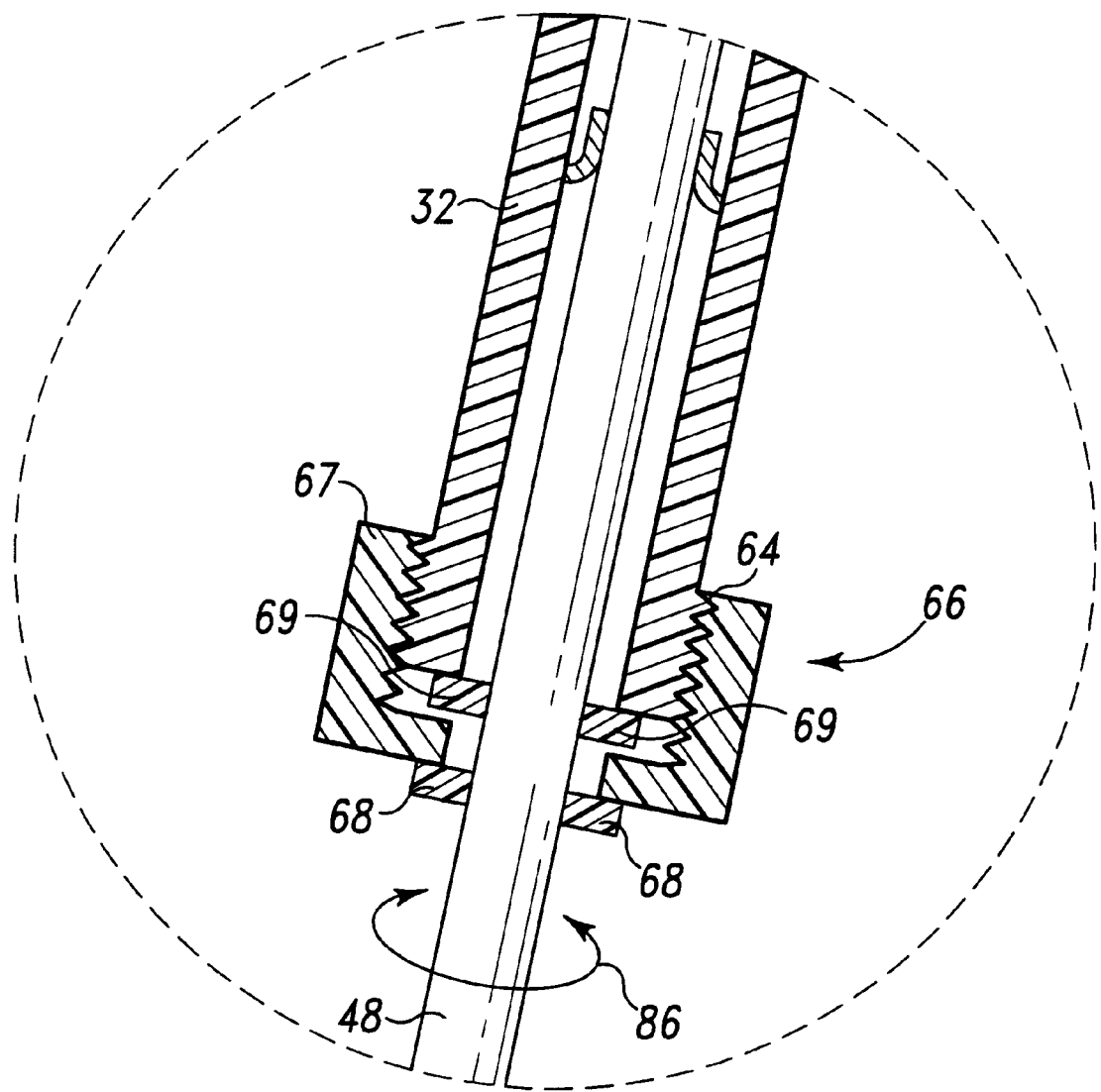
FIG. 6 is an enlarged view of a portion of FIG. 3 which is encircled and indicated as FIG. 6.

The dialysis catheter 48 also includes a second locking component 66 secured thereto. The second locking component 66 cooperates with the first locking component 64 to lock the dialysis catheter 48 to the guide catheter 32. In particular, the second locking component 66 includes the threaded cap 67 which has a hole extending therethrough as shown in FIG. 6. The dialysis catheter 48 may extend through the hole as also shown in FIG. 6. The second locking component 66 further includes an upper tab 68 and a lower tab 69 each which extends around and is secured to the outer surface of the dialysis catheter 48. The cap 67 is interposed between the upper tab 68 and the lower tab 69 so as to be retained therebetween. The threaded cap 67 is able to be rotated relative to the dialysis catheter in the directions indicated by arrow 86 in order to secure/release the dialysis catheter to/from the guide catheter.

While the first locking component 64 and the second locking component 66 have been described herein as functioning to lock the dialysis catheter 48 to the guide catheter 32 and has substantial benefits, numerous other arrangements may alternatively be incorporated into the dialysis system 16 to function to lock the dialysis catheter 48 to the guide catheter 32 and still achieve many of the advantages of the present invention.

For example, another locking arrangement which may be used to lock the dialysis catheter 48 to the guide catheter 32 is a detent and groove type locking arrangement (not shown). In particular, such a locking mechanism would include a circumferential groove which is defined in an outer surface of the dialysis catheter 48 (the sidewall of the dialysis catheter may need to possess an increased thickness in order to define such groove therein). A detent (e.g. a ball), supported by the guide catheter 32, may be spring biased into the groove so as to lock the dialysis catheter 48 in relation to the guide catheter 32. When desired, the detent may be allowed to advance out of the groove. Thereafter, when the detent is positioned out of the groove, the dialysis catheter may be withdrawn from the guide lumen 34 of the guide catheter 32. Examples of detent and groove type locking arrangements which may be used with some modifications to lock the dialysis catheter 48 to the guide catheter 32 are disclosed in U.S. Pat. Nos. 4,900,202 and 5,013,194 each issued to Wienhold, and U.S. Pat. Nos. 5,470,180 and 5,779,404 each issued to Jore, the disclosures of each of these four U.S. patents being hereby incorporated by reference.

Yet another example of a locking arrangement which may be used to lock the dialysis catheter 48 to the guide catheter 32 is a leg and guide channel type locking arrangement (not shown). In particular, such a locking arrangement would include a short leg extending from an outer surface of the dialysis catheter 48. The leg would be fixed in relation to the dialysis catheter 48. The locking arrangement would further include a guide channel defined in a sidewall of the guide catheter 32. The guide channel would extend longitudinally for a short distance (e.g. a few centimeters) along the length of the guide catheter 32. At the distal end of the guide channel, there would exist a narrowed distal channel portion of reduced width. In operation, the leg would be positioned in the guide channel. If it would be desirable to lock the dialysis catheter 48 in relation to the guide catheter 32, the dialysis catheter 48 could be advanced distally in relation to the guide catheter 32 until the leg became wedged within the narrowed distal channel portion. A secondary safety latch may be employed to retain the leg in the narrowed distal channel portion.

The dialysis catheter 48 further includes an egress line 78 and an ingress line 80. The egress line 78 is in fluid communication with the egress lumen 52, while the ingress line 80 is in fluid communication with the ingress lumen 50. The egress line 78 has an adapter or injection cap 74 attached thereto, and the ingress line 80 has an adapter or injection cap 76 attached thereto.

Figure 5A:
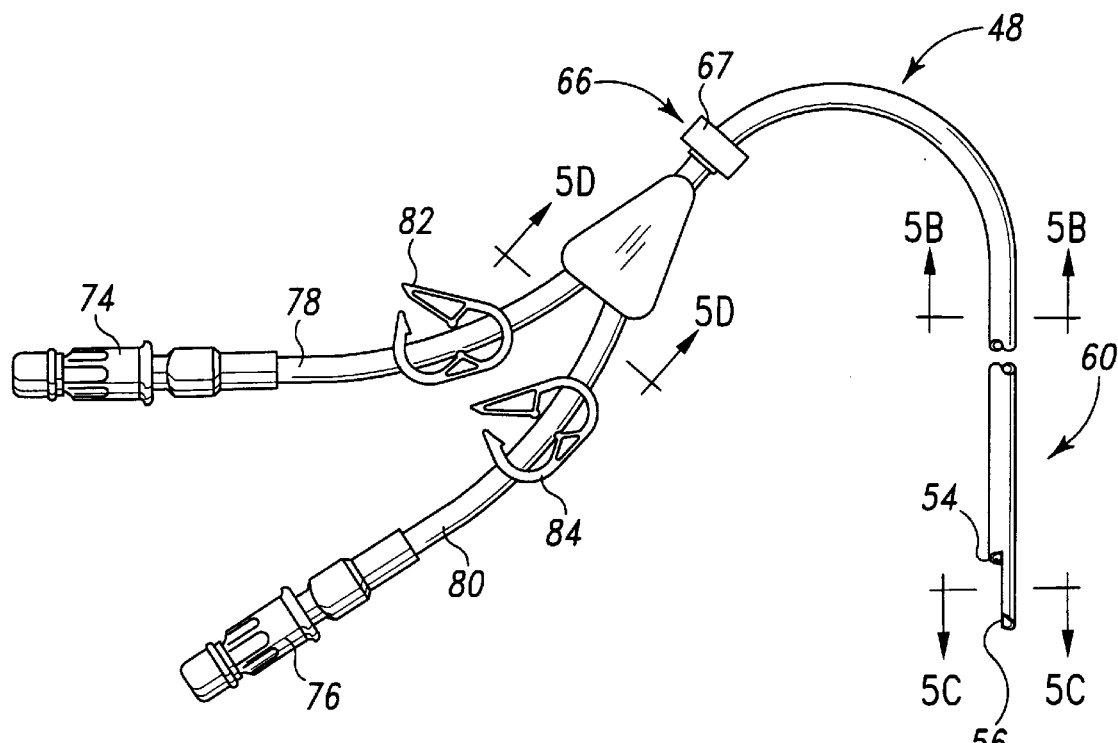
FIG. 5A is an enlarged side elevational view of the original dialysis catheter of the long-term dialysis catheter system shown in FIG. 1.
Figure 5B:
FIG. 5B is an enlarged cross sectional view of the original dialysis catheter taken along the line 5B—5B of FIG. 5A as viewed in the direction of the arrows.
Figure 5C:
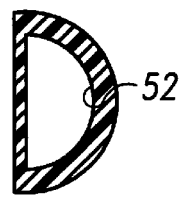
FIG. 5C is an enlarged cross sectional view of the original dialysis catheter taken along the line 5C—5C of FIG. 5A as viewed in the direction of the arrows.
Figure 5D:
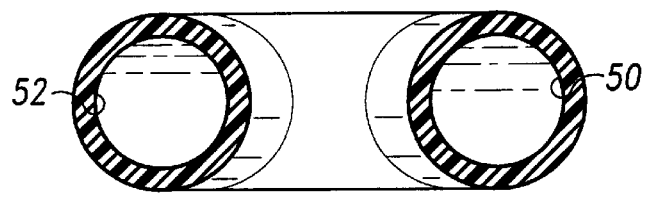
FIG. 5D is an enlarged cross sectional view of the original dialysis catheter taken along the line 5D—5D of FIG. 5A as viewed in the direction of the arrows.

In addition, a clamp 82 is positioned on the egress line 78, while a clamp 84 is positioned on the ingress line 80 as shown in FIG. 5A. It should be understood that closure of the clamp 82 causes fluid communication between adapter 74 and original distal egress orifice 56 to be prevented. Similarly, closure of the clamp 84 prevents fluid communication between the adapter 76 and the distal ingress orifice 54.

The dialysis catheter 48 may be positioned within the guide lumen 34 of the guide catheter 32 as shown in FIG. 3. When the dialysis catheter 48 is positioned within the guide lumen 34 as shown in FIG. 3, the dialysis catheter is said to be positioned in an "inserted position." When the dialysis catheter 48 is entirely removed from the guide lumen 34, the dialysis catheter is said to be positioned in a "removed position."

When the dialysis catheter 48 is positioned in the inserted position, the distal segment 60 of the dialysis catheter 48 extends out of the distal guide orifice 36 of the guide catheter 32. Accordingly, the distal ingress orifice 54 and the distal egress orifice 56 are each positioned outside of guide lumen 34 when the dialysis catheter 48 is located in the inserted position. Moreover, when the dialysis catheter 48 is located in the inserted position, the threaded cap 67 is positioned adjacent to the first locking component 64 such that the threaded cap 67 can be rotated relative to guide catheter 32 so as to lock the second locking component 66 to the first locking component 64. Note that locking the second locking component 66 to the first locking component 64 in the above described manner locks the dialysis catheter 48 to the guide catheter 32.

Figure 8:
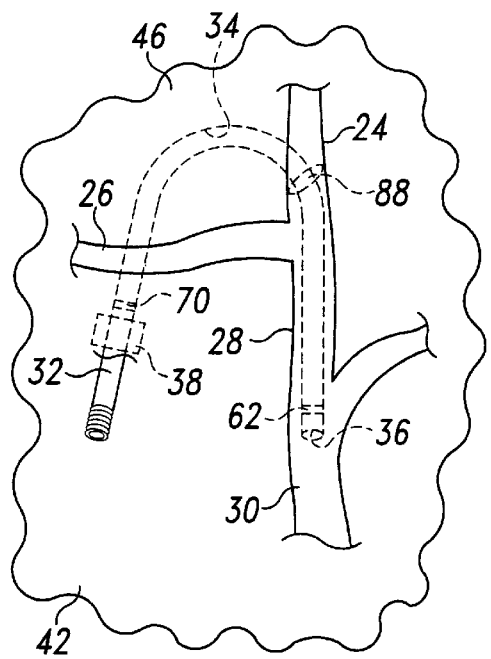
FIG. 8 is a reduced view which is similar to FIG. 7, but showing the original dialysis catheter removed from the guide lumen of the guide catheter.
Figure 9:
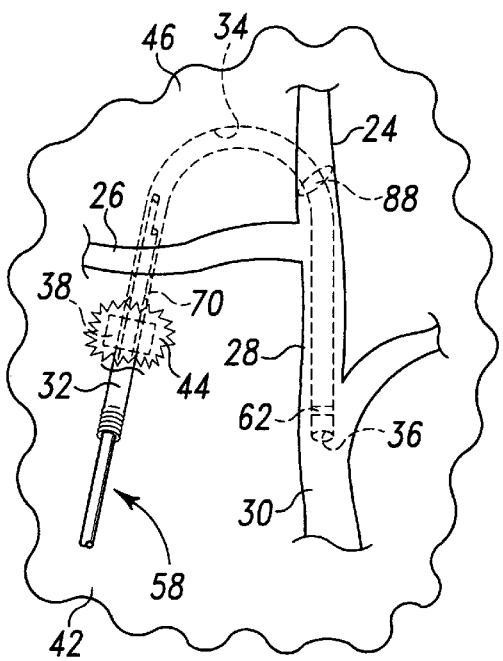
FIG. 9 is a view similar to FIG. 8, but showing a replacement dialysis catheter partially inserted into the guide lumen of the guide catheter.
Figure 10:
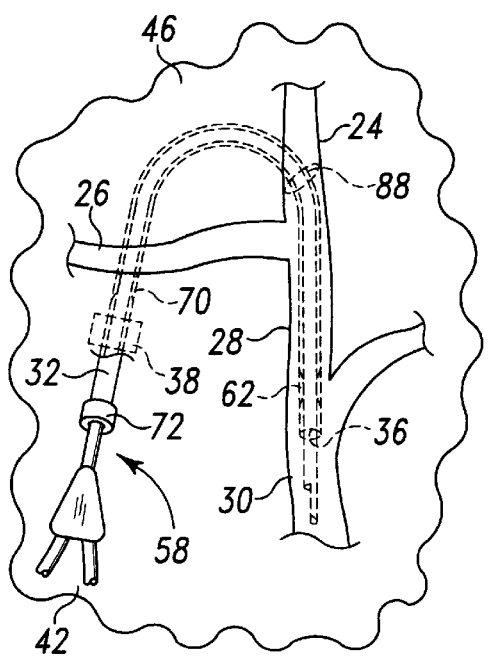
FIG. 10 is a view similar to FIG. 9, but showing the replacement dialysis catheter fully inserted into the guide lumen of the guide catheter.

Referring now to FIGS. 8–10, the structure and use of the dialysis catheter 58 will be described. The dialysis catheter 58 is substantially similar to the dialysis catheter 48. In particular, the dialysis catheter 58 includes an ingress lumen and an egress lumen defined therein. The ingress lumen defines a distal ingress orifice. Similarly, the egress lumen defines a distal egress orifice. The distal ingress orifice and the distal egress orifice are defined in a distal segment of the dialysis catheter 58.

The dialysis catheter 58 also includes a third locking component 72 secured thereto (see FIG. 10). The third locking component 72 cooperates with the first locking component 64 to lock the dialysis catheter 58 to the guide catheter 32. In particular, the third locking component 72 includes a threaded cap which has a hole extending therethrough. The dialysis catheter 58 may extend through the hole as also shown in FIG. 10. The third locking component 72 further includes an upper tab and a lower tab each which extends around and is secured to the outer surface of the dialysis catheter 58. The threaded cap is interposed between the upper tab and the lower tab so as to be retained therebetween. The threaded cap is able to be rotated relative to the dialysis catheter in order to secure/release the dialysis catheter 58 to/from the guide catheter 32.

The dialysis catheter 58 further includes an egress line and an ingress line. The egress line is in fluid communication with the egress lumen, while the ingress line is in fluid communication with the ingress lumen. The egress line has an adapter attached thereto, and the ingress line has another adapter attached thereto. In addition, a clamp may be positioned on the egress line, while another clamp may positioned on the ingress line. It should be understood that closure of the above-identified clamps cause fluid communication between the above adapters and the above distal egress orifice and distal ingress orifice to be prevented.

The dialysis catheter 58 may be positioned within the guide lumen 34 of the guide catheter 32 as shown in FIG. 10. When the dialysis catheter 58 is positioned within the guide lumen 34 as shown in FIG. 10, the dialysis catheter is said to be positioned in an "inserted position." When the dialysis catheter 58 is entirely removed from the guide lumen 34, the dialysis catheter 58 is said to be positioned in a "removed position."

When the dialysis catheter 58 is positioned in the inserted position, a distal segment of the dialysis catheter 58 extends out of the distal guide orifice 36 of the guide catheter 32. Accordingly, the distal ingress orifice and the distal egress orifice of the dialysis catheter 58 are each positioned outside of guide lumen 34 when the dialysis catheter 58 is located in the inserted position. Moreover, when the dialysis catheter 58 is located in the inserted position, the threaded cap is positioned adjacent to the first locking component 64 such that the threaded cap can be rotated relative to guide catheter 32 so as to lock the third locking component 72 to the first locking component 64. Note that locking the third locking component 72 to the first locking component 64 in the above described manner locks the dialysis catheter 58 to the guide catheter 32.

The guide catheter 32 is placed within the body 46 using the tunneled catheter technique. In particular, a first opening is created by making a small incision in the skin 42 with a scalpel directly over the right internal jugular vein 24. Thereafter, the right internal jugular vein 24 is punctured to create a venotomy 88 at a location directly below the first opening by advancing a needle through the skin incision and the subcutaneous tissue 44 and into the right internal jugular vein 24. Thereafter, a guidewire is advanced through the needle into the right internal jugular vein 24 through the venotomy 88. The needle is then removed over the guidewire. One or more tubular vessel dilators is passed over the guidewire to widen the opening defined in the skin 42 and subcutaneous tissue 44, and further to widen the venotomy 88 defined in the wall of the right internal jugular vein 24 to a caliber similar to that of the tubular guide. Thereafter, the tubular guide is advanced over the guidewire and into the right internal jugular vein 24. Then, a second opening is created in the skin 42 which is spaced apart at least several centimeters from the first opening. A tunneling instrument is advanced from the second opening to the first opening so as to create a passageway within the subcutaneous tissue 44 under the skin 42 between the first opening and the second opening. The guide catheter 32 is then advanced into the second opening and through the passageway such that a distal end of the guide catheter 32 is located adjacent the first opening. The distal end of the guide catheter 32 is then inserted through the tubular guide member and into the right internal jugular vein 24 so that the tissue ingrowth member 38 is positioned in the subcutaneous tissue 44. Thereafter, the tubular guide member is removed. The first opening is then closed with suture whereby the guide catheter 32: (a) is no longer exposed through the first opening, (b) extends for at least several centimeters under the skin 42 between the second opening and the venotomy 88, and (c) extends out of the second opening so that the proximal end of the guide catheter 32 is located outside of the body 46.

Figure 7:
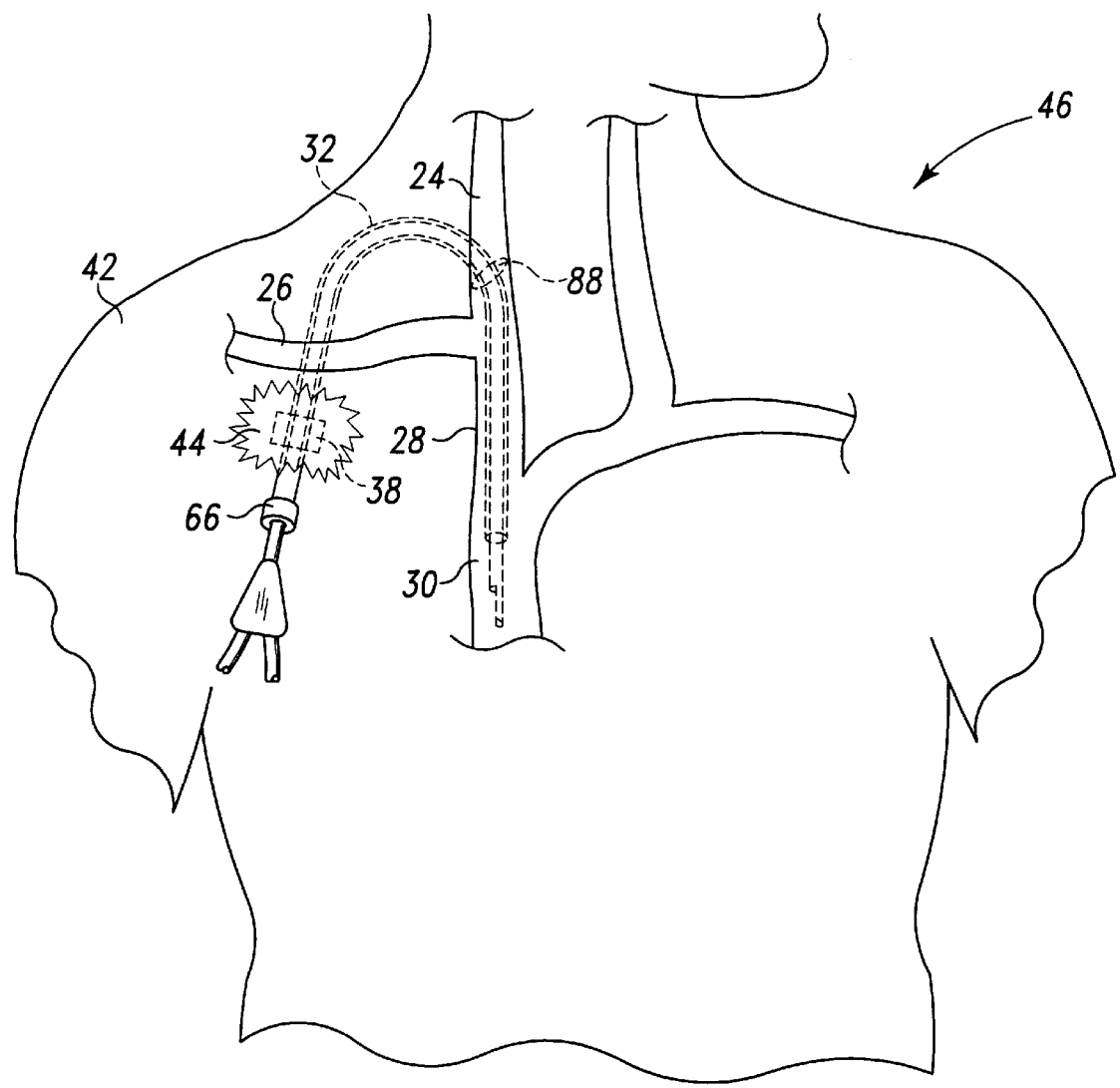
FIG. 7 is an enlarged view which is similar to FIG. 2, but showing the long-term dialysis catheter system of FIG. 3 (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.

Note that after the guide catheter 32 is placed in the vascular system 22 as described above, the guide catheter 32 is positioned in the right internal jugular vein 24, the right innominate vein 28, and the superior vena cava 30 as shown in FIG. 7. Moreover, note that as the tissue ingrowth member 38 remains in contact with the subcutaneous tissue 44 over a period of time, the subcutaneous tissue 44 becomes affixed to the tissue ingrowth member 38 thereby securing the guide catheter 32 to the body 46. As discussed above, affixation of the tissue ingrowth member 38 to the subcutaneous tissue 44 in the above described manner helps prevent bacterial migration up the guide catheter 32 from the second opening to the venotomy 88 thereby preventing serious infection.

Once the guide catheter 32 is placed in the body 46 as described above, the dialysis catheter 48 is advanced through the guide lumen 34 of the guide catheter 32 so that the distal ingress orifice 54 and the distal egress orifice 56 are advanced out of the distal guide orifice 36 and positioned within the superior vena cava 30 as shown in FIG. 7. (In other words, the dialysis catheter 48 is advanced to its inserted position.) The dialysis catheter 48 is then locked to guide catheter 32 utilizing the first locking component 64 and the second locking component 66 in the above described manner.

I(a). First Manner of Using Catheter System 16

According to a first preferred manner of using the catheter system 16 (see FIG. 3), the original dialysis catheter 48 is replaced only after the dialysis catheter 48 becomes substantially inoperative due to partial or total occlusion of either or both of its lumens 50, 52 due to blood clot build-up.

In particular, when a patient desires to be dialyzed (i.e. engage in a dialysis session), egress line 78 and ingress line 80 are respectively connected to the inlet line 18 and the outlet line 20 of the hemodialysis machine 8 as shown in FIG. 1. A dialysis procedure is then performed on the patient's body 46 in a well known manner. Upon completion of the dialysis procedure, the egress line 78 and ingress line 80 are respectively disconnected from the inlet line 18 and the outlet line 20, and the patient is able to carry on about his/her business. Thereafter, when a patient desires to be dialyzed again, the above procedure is repeated. After a number of dialysis sessions, the lumens of the dialysis catheter 48 may become partially or even totally occluded due to blood clot build-up. In order to remedy this problem prior to continuing the dialysis sessions, the dialysis catheter 48 may be replaced with the dialysis catheter 58. In particular, the dialysis catheter 48 is unlocked from the guide catheter 32 and withdrawn from the guide lumen 34. Then, the dialysis catheter 58 is positioned within the guide lumen 34 of the guide catheter 32, and locked to the guide catheter 32. Thereafter, the dialysis sessions may be continued.

It should be understood that the blood flow valves 62 and 70 prevent blood from escaping through guide lumen 34 after the dialysis catheter 48 has been removed from the guide catheter 32 and before the dialysis catheter 58 is inserted into the guide catheter. Note also that the blood flow valves 62 and 70 also prevent air from entering the vascular system 22 through the guide lumen 34 after the dialysis catheter 48 has been removed from the guide catheter 32 and before the dialysis catheter 58 is inserted into the guide catheter.

It should further be appreciated that during a dialysis session when either the dialysis catheter 48 or the dialysis catheter 58 is positioned within the guide catheter 32, the blood flow valves 62 and 70 function to prevent blood and/or air leakage through a space defined between the outer surface of the dialysis catheter 48, 58 and the inner surface of the guide catheter 32.

I(b). Second Manner of Using Catheter System 16

An alternative manner of using the catheter system 16 will be described. In particular, according to a second preferred manner of using the catheter system 16, the original dialysis catheter 48 is a "single use" catheter. In other words, the original dialysis catheter 48 is only used for a single dialysis session, and thereafter discarded. Hence, the dialysis catheter 48 would typically never be left in the vascular system 22 long enough to become substantially inoperative due to partial or total occlusion of either or both of its lumens 50, 52 due to blood clot build-up.

Figure 11:
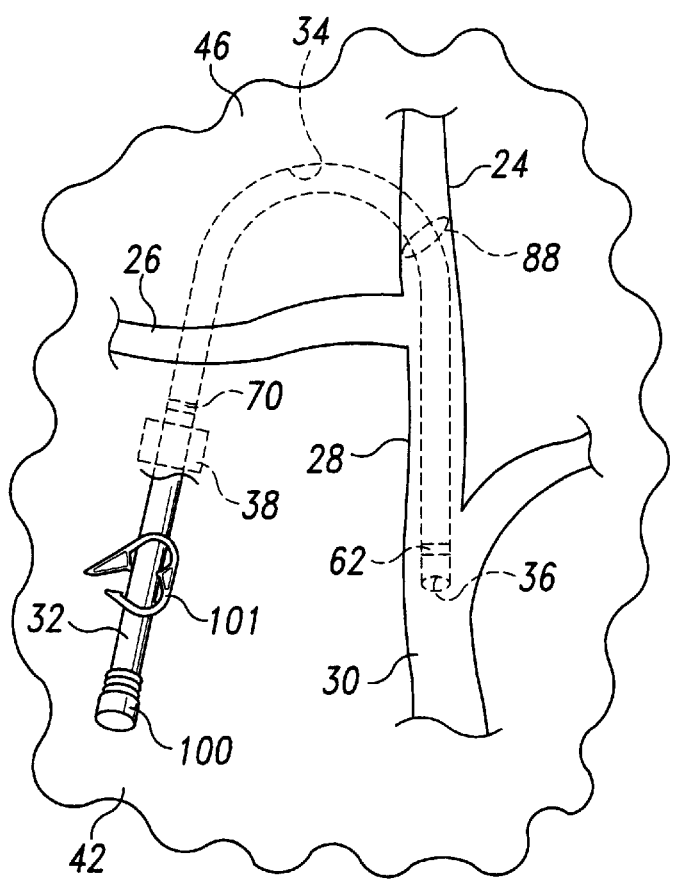
FIG. 11 is a view similar to FIG. 8, but showing neither the original dialysis catheter nor the replacement dialysis catheter inserted into the guide lumen of the guide catheter, but rather showing a closure member secured to the guide catheter so as to cover its proximal guide orifice.
Figures 12, 13:
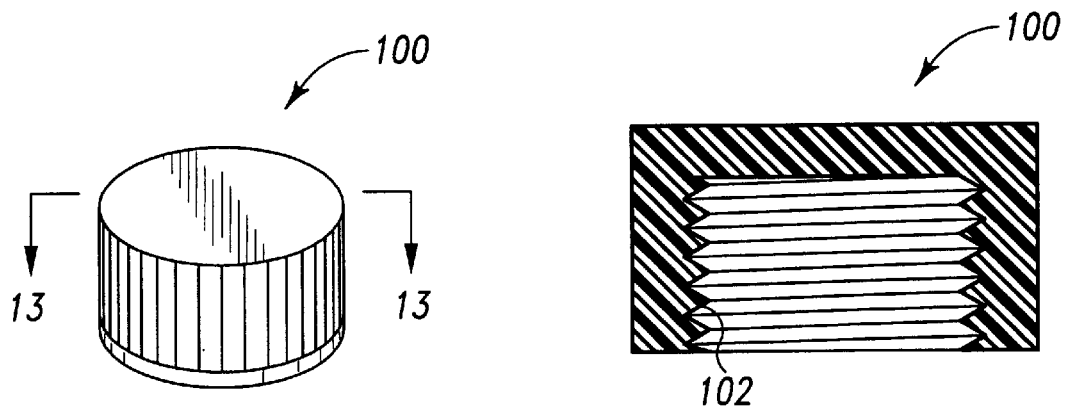
FIG. 12 is an enlarged perspective view of the closure member of FIG. 11.
FIG. 13 is an enlarged cross sectional view of the closure member of FIG. 12 taken along the line 13—13 of FIG. 12 as viewed in the direction of the arrows.

To facilitate use of the catheter system 16 according the second preferred manner, the catheter system 16 further includes a closure member 100, such as a cap, which is able to be secured to the guide catheter 32 so as to cover its proximal guide orifice 35 (see FIG. 11–13). The closure member 100 includes internal threads 102 which cooperates with the first locking component 64 so as to lock the closure member 100 to the guide catheter 32 as shown in FIG. 11. The closure member 100 remains locked to the guide catheter 32 in the above-described manner between dialysis sessions in order to prevent contaminants from advancing into the vascular system 22 via the guide lumen 34. The closure member 100 also prevents blood from escaping through guide lumen 34, as well as, air from entering the vascular system 22 through guide lumen 34. Note that the blood flow valves 62 and 70 also function for similar preventative purposes. Optionally, a clamp 101 may also be positioned on the proximal end portion of the guide catheter 32 as shown in FIG. 11 for similar preventative purposes. The clamp 101 is substantially identical in construction and function to the clamps 82, 84 discussed hereinabove.

While cooperation between the internal threads 102 of the closure member 100 and the external threads of the first locking component 64 function to lock the closure member 100 to the guide catheter 32 and has substantial benefits, numerous other types of locking arrangements may alternatively be incorporated into the dialysis system 16 to function to lock the closure member 100 to the guide catheter 32. For example, a detent and groove type locking arrangement which is somewhat similar to the detent and groove type locking arrangement described above with respect to locking the dialysis catheter 48 to the guide catheter 32 may be used. Moreover, for example, a leg and guide channel type locking arrangement which is somewhat similar to the leg and guide channel type locking arrangement described above with respect to locking the dialysis catheter 48 to the guide catheter 32 may also be used.

Thus, according to this alternative manner of using the catheter system 16, when a patient desires to be dialyzed (i.e. engage in a dialysis session), the guide catheter 32 is prepped in a sterile manner such as by applying an antibacterial solution thereto. Thereafter, the closure member 100 is unlocked from the guide catheter 32. In particular, the closure member 100 is rotated in relation to the guide catheter 32 until the closure member becomes separated from the guide catheter. Thereafter, the dialysis catheter 48 is advanced through the guide lumen 34 of the guide catheter 32 so that the distal ingress orifice 54 and the distal egress orifice 56 are advanced out of the distal guide orifice 36 and positioned within the superior vena cava 30 as shown in FIG. 7. (In other words, the dialysis catheter 48 is advanced to its inserted position.) The dialysis catheter 48 is then locked to guide catheter 32 utilizing the first locking component 64 and the second locking component 66 in the above described manner.

Then, the egress line 78 and ingress line 80 are respectively connected to the inlet line 18 and the outlet line 20 of the hemodialysis machine 8 as shown in FIG. 1. A dialysis procedure is then performed on the patient's body 46 in a well known manner. Upon completion of the dialysis procedure, the egress line 78 and ingress line 80 are respectively disconnected from the inlet line 18 and the outlet line 20. Thereafter, the dialysis catheter 48 is withdrawn from the guide lumen 34 of the guide catheter 32 and then discarded. After such withdrawal, the closure member 100 is secured to the guide catheter 32 in the manner described above so as to cover its proximal guide orifice 35, and the patient is thereafter able to carry on about his/her business.

Then, when the patient desires to be dialyzed again (i.e. engage in a dialysis session), the guide catheter 32 is prepped in a sterile manner such as by applying an antibacterial solution thereto. Thereafter, the closure member 100 is unlocked from the guide catheter 32. Then, the dialysis catheter 58 is advanced through the guide lumen 34 of the guide catheter 32 so that its distal ingress orifice and its distal egress orifice are advanced out of its distal guide orifice and positioned within the superior vena cava 30 as shown in FIG. 10. The dialysis catheter 58 is then locked to guide catheter 32 utilizing its first locking component and the second locking component 64 in the above described manner. Subsequently, its egress line and its ingress line are respectively connected to the inlet line 18 and the outlet line 20 of the hemodialysis machine 8 as shown in FIG. 1. Another dialysis procedure is then performed on the patient's body 46 in a well known mariner. Upon completion of the dialysis procedure, its egress line and its ingress line are respectively disconnected from the inlet line 18 and the outlet line 20. Thereafter, the dialysis catheter 58 is withdrawn from the guide lumen 34 of the guide catheter 32 and then discarded. After such withdrawal, the closure member 100 (or a new closure member similar to closure member 100) is secured to the guide catheter 32 in the manner described above so as to cover its proximal guide orifice 35, and the patient is again able to carry on about his/her business.

Please note that according to the second manner of using the catheter system 16, the dialysis catheters 48, 58 are only a "single use" catheter. Thus, the dialysis, catheter is used during only a single dialysis session whereby the dialysis catheters 48, 58 contact the blood located in the vascular system 22 for only a relatively short period of time (e.g. four hours) during its useful life. Accordingly, the physical structure of the dialysis catheters 48, 58 may be substantially the same or similar to the physical structure of a conventional short-term catheter. For example, the thickness of the sidewalls of the dialysis catheters 48, 58 which define the ingress lumen (e.g. lumen 50) and the egress lumen (e.g. lumen 52) may be made to be substantially thinner than the thickness of the sidewalls which define the corresponding lumens of a conventional long-term dialysis catheter. This may help reduce the necessary magnitude of the outer diameter of the guide catheter 32 in which the dialysis catheter 48 is positionable.

I(c). Third Manner of Using Catheter System 16

Another alternative manner of using the catheter system 16 will be described. In particular, according to a third preferred manner of using the catheter system 16, the original dialysis catheter 48 is replaced with the replacement dialysis catheter 58, as described above, after an experimentally determined number of dialysis sessions is performed. For example, if experimental studies show that most dialysis catheters are operative after four dialysis sessions but become inoperative during or before a fifth dialysis session, then the original dialysis catheter 48 is replaced with the replacement dialysis catheter 58, as described above, after every fourth dialysis session is performed on a particular patient.

Or, if a certain patient has a history which indicates that his/her dialysis catheter will remain operative after three dialysis sessions but will become inoperative during or before a fourth dialysis session, then this particular patient would have his/her original dialysis catheter 48 replaced with a replacement dialysis catheter 58, as described above, after every three dialysis sessions are performed.

Obviously, whatever criteria is used, the original dialysis catheter 48 may be replaced with the replacement dialysis catheter 58, as described above, after any predetermined number of dialysis sessions are performed.

II. Catheter System 200

Figure 14:
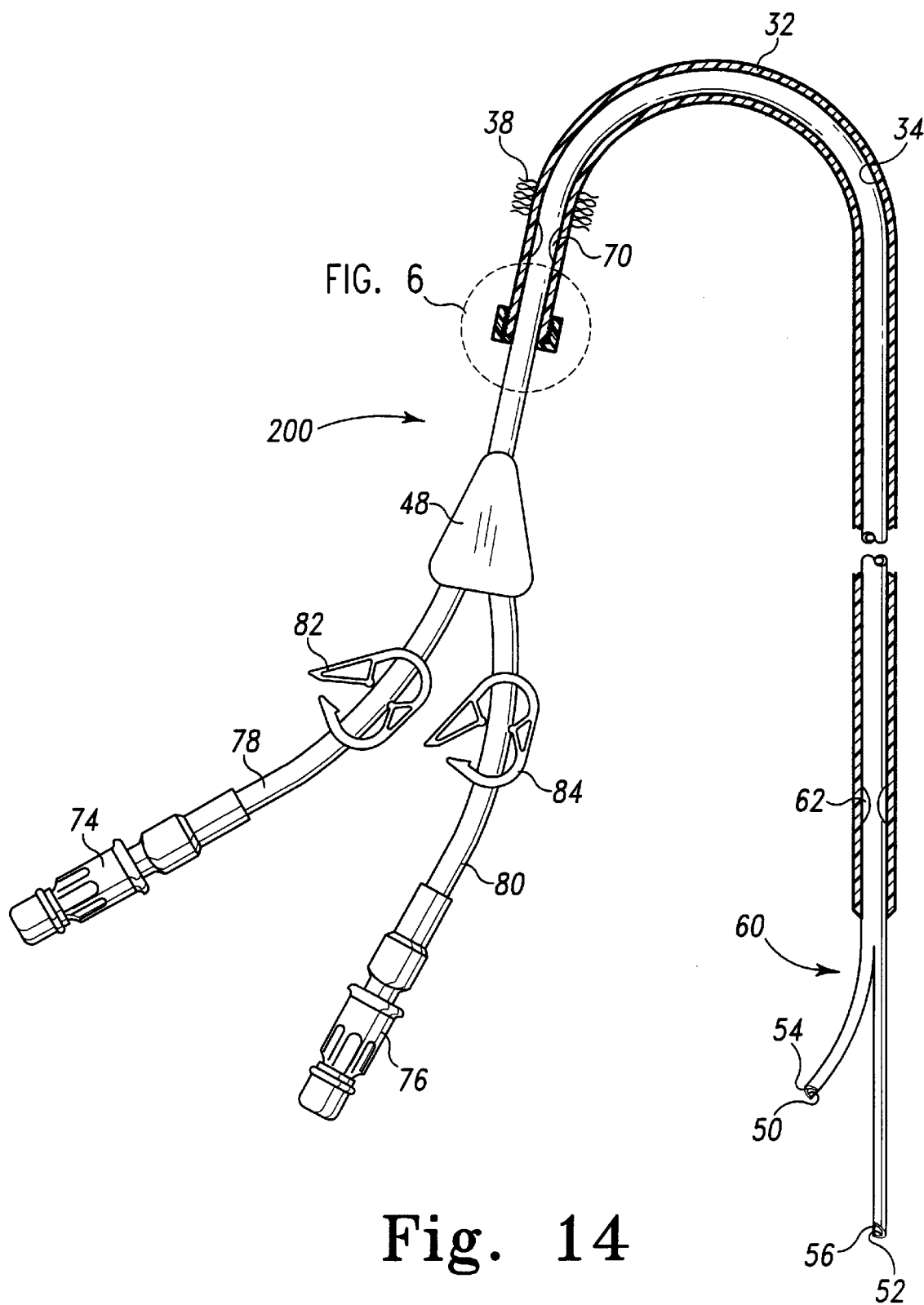
FIG. 14 is a view similar to FIG. 3, but showing another catheter system which incorporates the features of the present invention therein.

FIG. 14 shows a catheter system 200 which also incorporates the features of the present invention therein. The catheter system 200 is somewhat similar to the catheter system 16. Thus, the same reference numerals are used in FIG. 14 to designate common components which were previously discussed with regard to FIGS. 1–13. Moreover, the description of the components of the catheter system 200 which are common to the catheter system 16 will not be undertaken since they are designated with common reference numerals and such components have been previously described hereinabove. In addition, the guide catheter 32 of the catheter system 200 is placed within the body 46 in substantially the same manner as was described hereinabove with respect to the placement of the guide catheter 32 of the catheter system 16 within the body 46 (i.e. by the tunneled catheter technique).

However, the catheter system 200 differs from the catheter system 16 in that a portion of the distal segment 60 of the original dialysis catheter 48 which extends out of the distal guide orifice 36 of the guide catheter 32 is arranged in a bifurcated configuration as shown in FIG. 14. In particular, a distal portion of the ingress lumen 50 is arranged so as to gradually extend away from a distal portion of the egress lumen 52 as shown in FIG. 14. The catheter system 200 would also include a replacement dialysis catheter 58 which possesses the same physical construction and configuration as the original dialysis catheter 48 shown in FIG. 14.

The original dialysis catheter 48, shown in FIG. 14, possess a distal portion configured somewhat similar to the distal portion of a dialysis catheter disclosed in an article entitled "Management of Hemodialysis Catheters" which was published in the July 1999 edition of the periodical entitled "Applied Radiology" at pages 14–24 (authored by Haskel et al.), the disclosure of which is hereby incorporated by reference. Catheters having a distal portion configured in the above-described manner are sometimes referred to in the relevant medical art as "split-tip" catheters. For example, on page 20 of the Haskel article, a "split-tip" catheter is shown in FIG. 8.

II(a). First Manner of Using Catheter System 200

According to a first preferred manner of using the catheter system 200 (see FIG. 14), the original dialysis catheter 48 is replaced only after it becomes substantially inoperative due to partial or total occlusion of either or both of its lumens 50, 52 due to blood clot build-up. Such a manner of using the catheter system 200 would be substantially similar to the manner of using the catheter system 16 which was discussed herein in section 1(a) entitled "First Manner of Using Catheter System 16".

II(b). Second Manner of Using Catheter System 200

In accordance with a second preferred manner of using the catheter system 200, the original dialysis catheter 48 is a "single use" catheter. In other words, the original dialysis catheter 48 of catheter system 200 is only used for a single dialysis session, and thereafter discarded. Hence, the original dialysis catheter 48 would typically never be left in the vascular system 22 long enough to become substantially inoperative due to partial or total occlusion of either or both of its lumens 50, 52 due to blood clot build-up. Such a manner of using the catheter system 200 would be substantially similar to the manner of using the catheter system 16 which was discussed herein in section 1(b) entitled "Second Manner of Using Catheter System 16".

Also, please note that according to the second manner of using the catheter system 200, the original catheter 48 and the replacement catheter 58 are only a "single use" catheter. Accordingly, the physical structure of the catheters 48, 58 of the catheter system 200 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

II(c). Third Manner of Using Catheter System 200

According to a third preferred manner of using the catheter system 200, the original dialysis catheter 48 is replaced with the replacement dialysis catheter 58, as described above, after any predetermined number of dialysis sessions are performed. For example, such predetermined number may be (i) determined from experimental studies, (ii) determined based on patient history, or (iii) determined based on other criteria. Such a manner of using the catheter system 200 would be substantially similar to the manner of using the catheter system 16 which was discussed herein in section 1(c) entitled "Third Manner of Using Catheter System 16".

III. Catheter System 300

Figure 15:
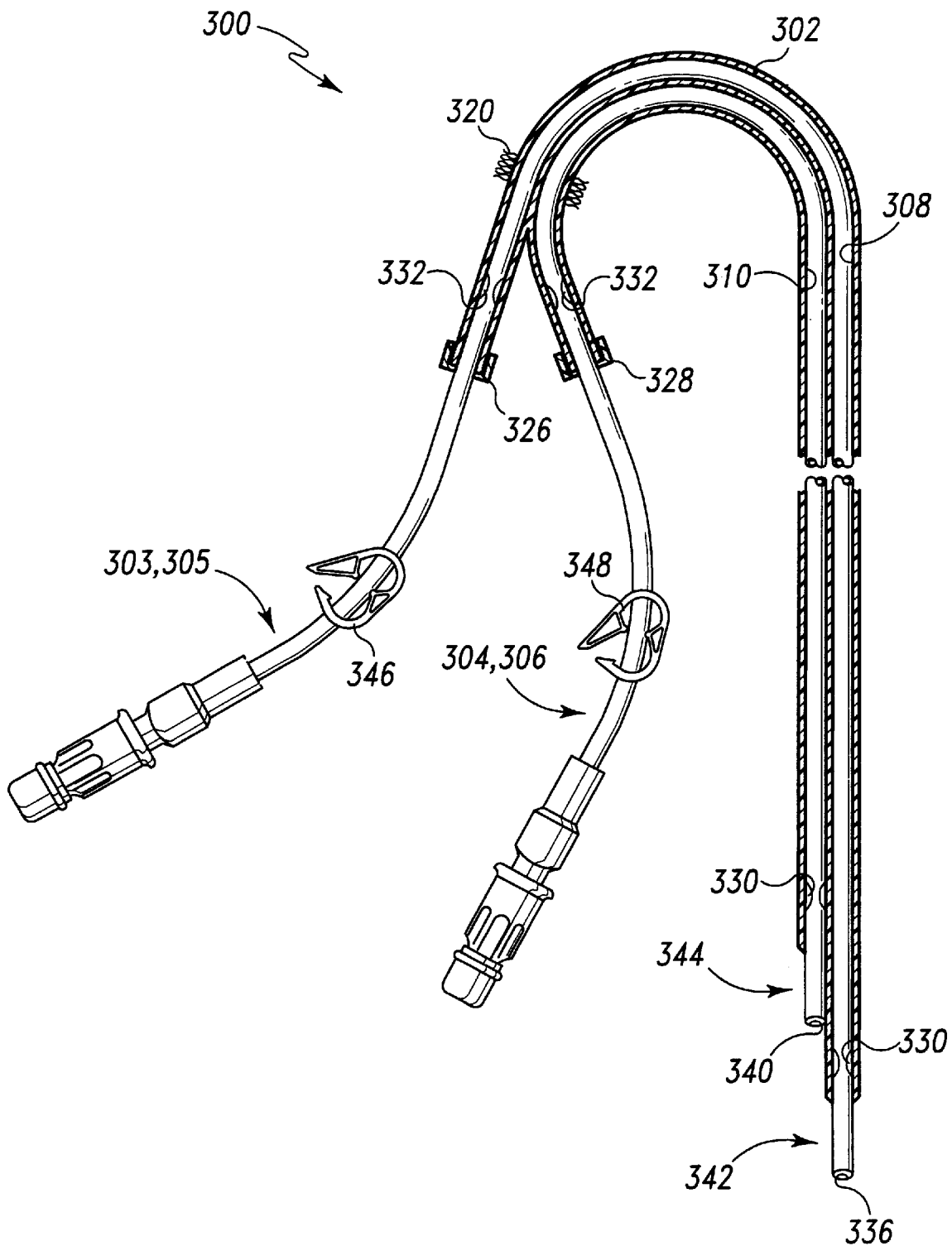
FIG. 15 is a view similar to FIG. 3, but showing yet another catheter system which incorporates the features of the present invention therein.

FIG. 15 shows a catheter system 300 which also incorporates the features of the present invention therein. The catheter system 300 includes a guide catheter 302, a first original single lumen catheter 303, and a second original single lumen catheter 304. The catheter system 300 further includes a first replacement single lumen catheter 305, and a second replacement single lumen catheter 306 as will be discussed below.

The guide catheter 302 has a first guide lumen 308 and a second guide lumen 310 each which extends along the length of the guide catheter 302 as shown in FIG. 15. The first guide lumen 308 defines a first proximal guide orifice 312 and a first distal guide orifice 314, while the second guide lumen 310 defines a second proximal guide orifice 316 and a second distal guide orifice 318.

The first original catheter 303 is able to be positioned within the guide lumen 308 of the guide catheter 302, while the second original catheter 304 is able to be positioned within the guide lumen 310 of the guide catheter 302 as shown in FIG. 15. Similarly, the first replacement catheter 305 is also able to be positioned within the guide lumen 308 of the guide catheter 302, while the second replacement catheter 306 is also able to be positioned within the guide lumen 310 of the guide catheter 302 as shown in FIG. 15.

Note that the first original catheter 303 possesses the same physical construction and configuration as the first replacement catheter 305, and similarly the second original catheter 304 possesses the same physical construction and configuration as the second replacement catheter 306. Thus, for convenience of description, FIGS. 15 and 17 show reference numerals 303 and 305 identifying the same catheter. However, the first original catheter 303 will be located within the guide lumen 308 during a first period of time, while the first replacement catheter 305 will be located within the guide lumen 308 during a second period of time which is after the first period of time. Similarly, for convenience of description, FIGS. 15 and 18 show reference numerals 304 and 306 identifying the same catheter. However, the second original catheter 304 will be located within the guide lumen 310 during a first period of time, while the second replacement catheter 306 will be located within the guide lumen 310 during a second period of time which is after the first period of time.

In particular, according to one preferred manner of using the catheter system 300 during a medical procedure, such as a dialysis session, the first original catheter 303 and the second original catheter 304 are respectively positioned within the first guide lumen 308 and the second guide lumen 310 of the guide catheter 302 for a first period of time during which blood is infused and withdrawn therethrough. After the first period of time, the blood flow through the lumens of the first original catheter 303 and the second original catheter 304 may become partially or even totally inhibited due to blood clot build-up. In order to remedy this problem, the first original catheter 303 and the second original catheter 304 are respectively withdrawn from the first guide lumen 308 and the second guide lumen 310 of the guide catheter 302, and thereafter, the first replacement catheter 305 and the second replacement catheter 306 are respectively positioned within the first guide lumen 308 and the second guide lumen 310 of the guide catheter 302 for a subsequent second period of time during which blood is again infused and withdrawn therethrough.

Referring again to FIG. 15 as well as FIG. 16, the guide catheter 302 has a tissue ingrowth member 320 secured to an outer surface thereof. Tissue ingrowth member 320 is substantially identical to tissue ingrowth member 38 described hereinabove with regard to the catheter system 16.

As shown in FIG. 16, the guide catheter 302 includes (i) a first set of external threads 322 defined on an outer surface thereof near the first proximal guide orifice 312, and (ii) a second set of external threads 324 defined on an outer surface thereof near the second proximal guide orifice 316. The first set of external threads 322 cooperate with a first internally threaded cap 326 of the first original catheter 303 (and the first replacement catheter 305) to lock the first original catheter 303 (and the first replacement catheter 305) to the guide catheter 302 as shown in FIG. 15. Similarly, the second set of external threads 324 cooperate with a second internally threaded cap 328 of the second original catheter 304 (and the second replacement catheter 306) to lock the second original catheter 304 (and the second replacement catheter 306) to the guide catheter 302 as also shown in FIG. 15. The caps 326, 328 are substantially identical to the cap 67 which was described hereinabove with regard to catheter system 16. Moreover, each of the catheters 303, 304 (and 305, 306) are provided with an upper tab and a lower tab, similar to tabs 68, 69 of the catheter system 16 described above (see FIG. 6), to rotatably retain the caps 326, 328 in place.

While the original catheters 303, 304 and the replacement catheters 305, 306 are described as being locked to the guide catheter 302 using a locking arrangement which utilizes cooperating internal and external threads, and has substantial benefits thereby, numerous other arrangements may alternatively be incorporated into the dialysis system 300 to function to lock the original catheters 303, 304 and the replacement catheters 305, 306 to the guide catheter 302 and still achieve many of the advantages of the present invention. For example, the detent and groove type locking arrangement (not shown) or the leg and guide channel type locking arrangement (not shown) which were described above in regard to catheter system 16 may be utilized to lock the original catheters 303, 304 and the replacement catheters 305, 306 to the guide catheter 302.

The guide catheter 302 further includes a pair of distal blood flow valves 330 and a pair of proximal blood flow valves 332 positioned within the guide lumens 308, 310 as shown in FIGS. 15 and 16. The blood flow valves 330 and 332 are substantially identical to the blood flow valves 62 and 70 which were described hereinabove with regard to the catheter system 16.

Referring again to FIGS. 15, 17, and 18, the first original catheter 303 (and the first replacement catheter 305) includes a lumen 334. The lumen 334 defines a distal orifice 336. Similarly, the second original catheter 304 (and the second replacement catheter 306) includes a lumen 338. The lumen 338 defines a distal orifice 340. The distal orifice 336 is defined in a distal segment 342 of the first original catheter 303 (and the first replacement catheter 305). Similarly, the distal orifice 340 is defined in a distal segment 344 of the second original catheter 304 (and the second replacement catheter 306).

A clamp 346 is positioned on the first original catheter 303 (and the first replacement catheter 305), while another clamp 348 is positioned on the second original catheter 304 (and the second replacement catheter 306). The clamps 346, 348 are substantially identical in construction and function to the clamps 82, 84 discussed hereinabove with regard to the catheter system 16.

The first original catheter 303 (and the first replacement catheter 305) may be positioned within the first guide lumen 308 of the guide catheter 302, while the second original catheter 304 (and the second replacement catheter 306) may be positioned within the second guide lumen 310 of the guide catheter 302 as shown in FIG. 15. When the first original catheter 303 (or alternatively the first replacement catheter 305) is positioned within the first guide lumen 308 as shown in FIG. 15, the first original catheter 303 (or alternatively the first replacement catheter 305) is said to be positioned in an "inserted position." Similarly, when the second original catheter 304 (or alternatively the second replacement catheter 306) is positioned within the second guide lumen 310 as shown in FIG. 15, the second original catheter 304 (or alternatively the second replacement catheter 306) is also said to be positioned in an "inserted position." When the first original catheter 303 (or alternatively the first replacement catheter 305) is entirely removed from the first guide lumen 308, the first original catheter 303 (or alternatively the first replacement catheter 305) is said to be positioned in a "removed position." Similarly, when the second original catheter 304 (or alternatively the second replacement catheter 306) is entirely removed from the second guide lumen 310, the second original catheter 304 (or alternatively the second replacement catheter 306) is also said to be positioned in a "removed position."

When the first original catheter 303 (and the first replacement catheter 305) is positioned in the inserted position, the distal segment 342 of the first original catheter 303 (and the first replacement catheter 305) extends out of the distal guide orifice 314 of the guide catheter 302 as shown in FIG. 15. Similarly, when the second original catheter 304 (and the second replacement catheter 306) is positioned in the inserted position, the distal segment 344 of the second original catheter 304 (and the second replacement catheter 306) extends out of the distal guide orifice 318 of the guide catheter 302 as shown in FIG. 15. Accordingly, the distal orifices 336, 340 are each respectively positioned outside of the guide lumens 308, 310 when the first original catheter 303 (and the first replacement catheter 305) and the second original catheter 304 (and the second replacement catheter 306) are located in their inserted position.

Moreover, when the first original catheter 303 (and the first replacement catheter 305) is located in the inserted position, the threaded cap 326 is positioned adjacent to the first set of external threads 322 such that the threaded cap 326 can be rotated relative to the guide catheter 302 so as to lock the first original catheter 303 (and the first replacement catheter 305) to the guide catheter 302. Similarly, when the second original catheter 304 (and the second replacement catheter 306) is located in the inserted position, the threaded cap 328 is positioned adjacent to the second set of external threads 324 such that the threaded cap 328 can be rotated relative to the guide catheter 302 so as to lock the second original catheter 304 (and the second replacement catheter 306) to the guide catheter 302.

The guide catheter 302 is placed within the body 46 in substantially the same manner as was described hereinabove with respect to the placement of the guide catheter 32 of the catheter system 16 within the body 46 (i.e. by the tunneled catheter technique). Once the guide catheter 302 is placed in the body 46 as described above, the first original catheter 303 and the second original catheter 304 are respectively advanced through the guide lumens 308, 310 of the guide catheter 302 so that the distal orifices 336, 340 are respectively advanced out of the distal guide orifices 314, 318 and positioned within the superior vena cava 30 of the body 46. (In other words, the first original catheter 303 and the second original catheter 304 are respectively advanced to their inserted positions.) The first original catheter 303 and the second original catheter 304 are then respectively locked to the guide catheter 302 in the manner which has been previously described hereinabove.

Figure 19:
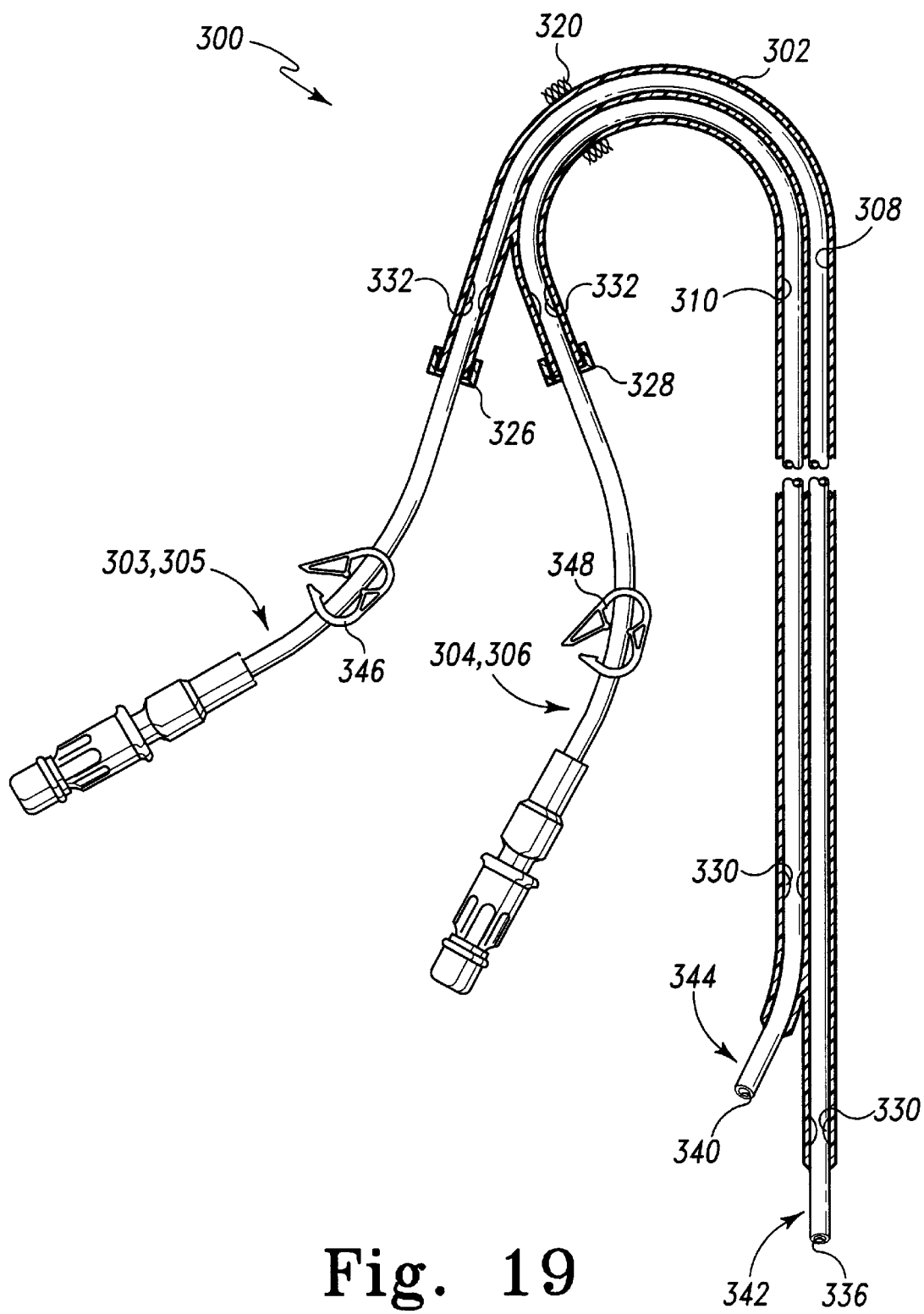
FIG. 19 is a view similar to FIG. 15, but showing another catheter system which incorporates the features of the present invention therein.

The catheter system 300 is shown in FIGS. 15 and 16 as having the distal segment of the guide lumen 310 located adjacent to the guide lumen 308. In the embodiment shown in FIGS. 15 and 16, the guide catheter 302 can be said to possess a side-by-side configuration. An alternative to providing the guide catheter 302 with a side-by-side configuration is shown in FIG. 19. In particular, a distal portion of the guide lumens 308, 310 of the catheter system 300 may be alternatively configured so that the distal portion of the guide catheter 302 is arranged in a bifurcated configuration as shown in FIG. 19. In such a configuration, the distal portion of the guide lumen 310 is arranged so as to gradually extend away from the distal portion of the guide lumen 308 as shown in FIG. 19. In the embodiment shown in FIG. 19, the guide catheter 302 can be said to possess a "split-tip" configuration.

III(a). First Manner of Using Catheter System 300

According to a first preferred manner of using the catheter system 300, the first original catheter 303 is replaced with the first replacement catheter 305 only after it becomes substantially inoperative due to partial or total occlusion of its lumen 334 due to, for example, blood clot build-up. Moreover, the second original catheter 304 is replaced with the second replacement catheter 306 only after it becomes substantially inoperative due to partial or total occlusion of its lumen 338 due to, for example, blood clot build-up. Such a manner of using the catheter system 300 would be substantially similar to the manner of using the catheter system 16 which was discussed herein in section 1(a) entitled "First Manner of Using Catheter System 16". However, it should be noted that it is possible, and may even be likely, that the first original catheter 303 (and the first replacement catheter 305) will be replaced due to blood clot build-up at a lower frequency in comparison to the replacement of the second original catheter 304 due to blood clot build-up. Such lower frequency of replacement may be attributable to the fact that during use of the catheter system 300, blood is advanced out of the first original catheter 303 (and the first replacement catheter 305) through the distal orifice 336. In contrast, during use of the catheter system 300, blood is advanced into the second original catheter 304 (and the second replacement catheter 306) through the distal orifice 340. Historically, occlusion problems occur more frequently during a dialysis procedure when attempting to withdraw blood from a patient's vascular system through a dialysis catheter in comparison to attempting to infuse blood back into a patient's vascular system through the dialysis catheter.

III(b). Second Manner of Using Catheter System 300

In accordance with a second preferred manner of using the catheter system 300, each of the first original catheter 303 and the second original catheter 304 is a "single use" catheter. In other words, both the first original catheter 303 and the second original catheter 304 of catheter system 300 are only used for a single dialysis session, and thereafter discarded. Hence, both the first original catheter 303 and the second original catheter 304 would typically never be left in the vascular system 22 long enough to become substantially inoperative due to partial or total occlusion of its respective lumens 334, 338 as a result of, for example, blood clot build-up. Such a manner of using the catheter system 300 would be substantially similar to the manner of using the catheter system 16 which was discussed herein in section 1(b) entitled "Second Manner of Using Catheter System 16".

Note that between dialysis sessions, when the first original catheter 303 (or the first replacement catheter 305) is not located within the guide lumen 308 of the guide catheter 302, a first closure member 350, such as a cap, is secured to the guide catheter 302 so as to cover the first proximal guide orifice 312. Optionally, a clamp (not shown) which is similar in construction and function to the clamp 101 of the catheter system 16 (see FIG. 11) may also be positioned on the branch of the guide catheter 302 near the first proximal guide orifice 312 between dialysis sessions. Also note that between dialysis sessions, when the second original catheter 304 (or the second replacement catheter 306) is not located within the guide lumen 310 of the guide catheter 302, a second closure member 352, such as another cap, is secured to the guide catheter 302 so as to cover the second proximal guide orifice 316. Optionally, another clamp (not shown) which is similar in construction and function to the clamp 101 of the catheter system 16 (see FIG. 11) may also be positioned on the branch of the guide catheter 302 near the second proximal guide orifice 316 between dialysis sessions. The closure members 350, 352 are substantially identical in construction and function to the closure member 100 of the catheter system 16 shown in FIGS. 11–13.

When the patient desires to be dialyzed again, the guide catheter 302 is prepped in a sterile manner such as by applying an anti-bacterial solution thereto. Thereafter, the closure members 350, 352 would be unlocked from the guide catheter 302, and thereafter the replacement catheters 305, 306 would be respectively inserted into the guide lumens 308, 310 and then locked to the guide catheter 302 as hereinabove described. Again, this manner of using the catheter system 300 would be substantially similar to the manner of using the catheter system 16 which was discussed herein in section 1(b) entitled "Second Manner of Using Catheter System 16".

Also, please note that according to the second manner of using the catheter system 300, the original catheters 303, 304 and the replacement catheters 305, 306 are only "single use" catheters. Accordingly, the physical structure of the original catheters 303, 304, 305, 306 of the catheter system 300 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

III(c). Third Manner of Using Catheter System 300

According to a third preferred manner of using the catheter system 300, the first original catheter 303 is replaced with the first replacement catheter 305 after any predetermined number of dialysis sessions is performed. Moreover, the second original catheter 304 is replaced with the second replacement catheter 306 after any predetermined number of dialysis sessions is performed. For example, such predetermined number may be (i) determined from experimental studies, (ii) determined based on patient history, or (iii) determined based on other criteria. Such a manner of using the catheter system 300 would be substantially similar to the manner of using the catheter system 16 which was discussed herein in section 1(c) entitled "Third Manner of Using Catheter System 16". In addition, the predetermined number of dialysis sessions after which the first original catheter 303 is replaced does not necessarily have to be equal to the predetermined number of dialysis sessions after which the second original catheter 304 is replaced. For example, the first original catheter 303 may be replaced with a first replacement catheter 305 after every four dialysis sessions, while the second original catheter 304 may be replaced with a second replacement catheter 306 after every three dialysis sessions.

IV. Catheter System 400

Figure 20:
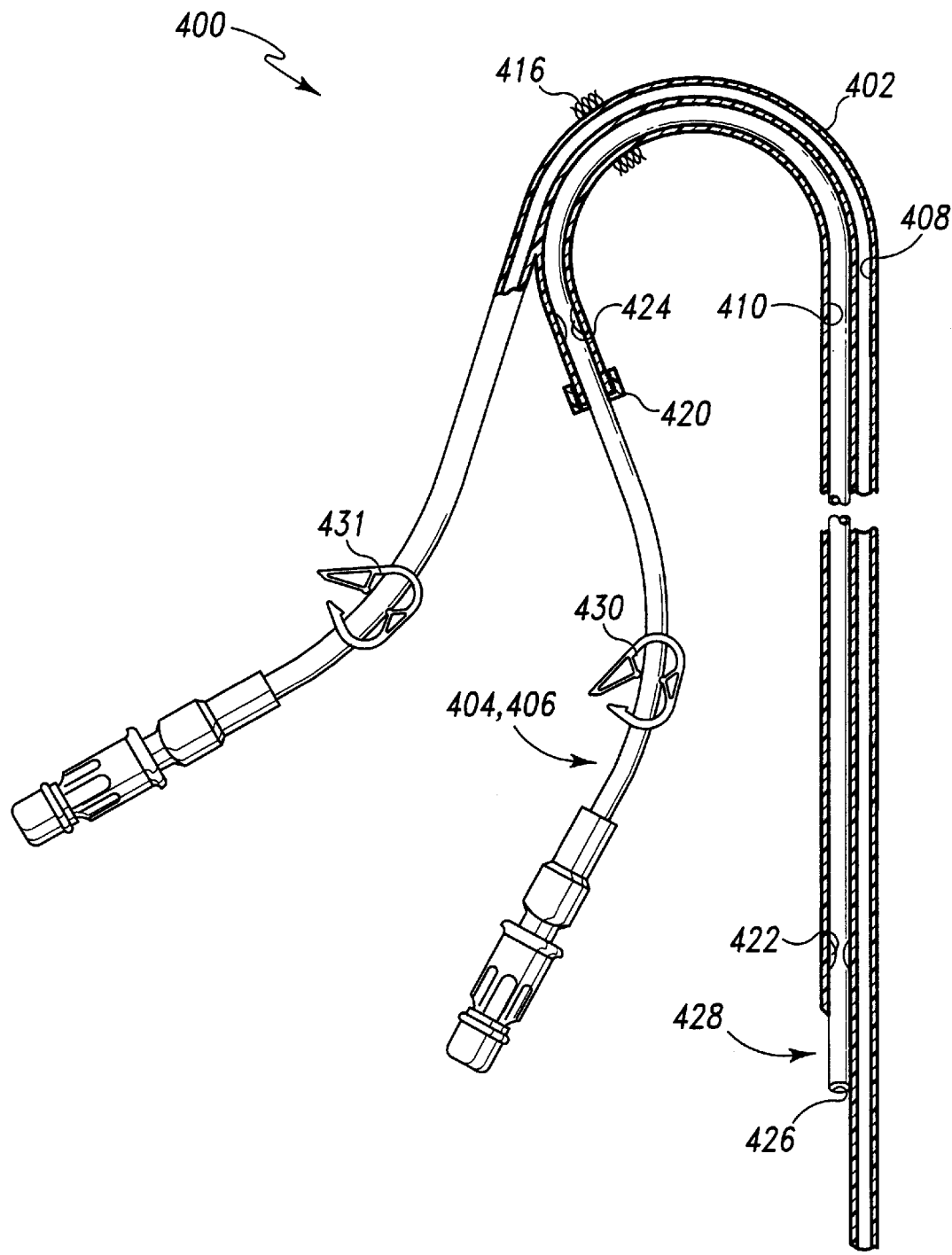
FIG. 20 is a view similar to FIG. 3, but showing another catheter system which incorporates the features of the present invention therein.

FIG. 20 shows a catheter system 400 which incorporates the features of the present invention therein. The catheter system 400 includes a guide catheter 402 and an original single lumen catheter 404. The original catheter 404 defines a lumen 405 through which blood may be advanced. The catheter system 400 further includes a replacement single lumen catheter 406 as will be discussed below. The guide catheter 402 has an active lumen 408 and a guide lumen 410 each which extends along the length of the guide catheter 402 as shown in FIG. 20. The guide lumen 410 defines a proximal guide orifice 412 and a distal guide orifice 414.

The original catheter 404 is able to be positioned within the guide lumen 410 of the guide catheter 402. Similarly, the replacement catheter 406 is also able to be positioned within the guide lumen 410 of the guide catheter 402. Note that the original catheter 404 possesses the same physical construction and configuration as the replacement catheter 406. Thus, for convenience of description, FIGS. 20–22 show reference numerals 404 and 406 identifying the same catheter. However, the original catheter 404 will be located within the guide lumen 410 during a first period of time, while the replacement catheter 406 will be located within the guide lumen 410 during a second period of time which is after the first period of time.

In particular, according to one preferred manner of using the catheter system 400 during a medical procedure, such as a dialysis session, the original catheter 404 is positioned within the guide lumen 410 for a first period of time during which blood is withdrawn from the vascular system 22 through its lumen 405. Also during the first period of time, blood is infused into the vascular system 22 through the active lumen 408 of the guide catheter 402. After the first period of time, the blood flow through the lumen 405 of the original catheter 404 may become partially or even totally inhibited due to, for example, blood clot build-up. In order to remedy this problem, the original catheter 404 is withdrawn from the guide lumen 410, and thereafter, the replacement catheter 406 is positioned within the guide lumen 410 of the guide catheter 402 for a subsequent second period of time during which blood is withdrawn from the vascular system 22 through the lumen 405 of the replacement catheter 406. Also during the second period of time, blood is infused into the vascular system 22 through the active lumen 408 of the guide catheter 402.

Referring again to FIGS. 20–21, the guide catheter 402 has a tissue ingrowth member 416 secured to an outer surface thereof. Tissue ingrowth member 416 is substantially identical to tissue ingrowth member 38 described hereinabove with regard to the catheter system 16.

As shown in FIGS. 20–21, the guide catheter 402 includes a set of external threads 418 defined on an outer surface thereof near the proximal guide orifice 412. The set of external threads 418 cooperates with an internally threaded cap 420 of the original catheter 404 (and the replacement catheter 406) to lock the original catheter 404 (and the replacement catheter 406) to the guide catheter 402 as shown in FIG. 20. The cap 420 is substantially identical to the cap 67 which was described hereinabove with regard to catheter system 16. Moreover, each of the catheters 404 and 406 is provided with an upper tab and a lower tab, similar to tabs 68, 69 of the catheter system 16 described above (see FIG. 6), to rotatably retain the cap 420 in place.

While the original catheter 404 and the replacement catheter 406 is described as being locked to the guide catheter 402 using a locking arrangement which utilizes cooperating internal and external threads, and has substantial benefits thereby, numerous other arrangements may alternatively be incorporated into the dialysis system 400 to function to lock the original catheter 404 and the replacement catheter 406 to the guide catheter 402 and still achieve many of the advantages of the present invention. For example, the detent and groove type locking arrangement (not shown) or the leg and guide channel type locking arrangement (not shown) which were described above in regard to catheter system 16 may be utilized to lock the original catheter 404 and the replacement catheter 406 to the guide catheter 402.

The guide catheter 402 further includes a distal blood flow valve 422 and a proximal blood flow valve 424 positioned within the guide lumen 410 as shown in FIGS. 20 and 21. The blood flow valves 422 and 424 are substantially identical to the blood flow valves 62 and 70 which were described hereinabove with regard to the catheter system 16. The guide catheter 402 may further include an additional distal blood flow valve (not shown) located in the distal portion of the active lumen 408 and an additional proximal blood flow valve (not shown) located in the proximal portion of the active lumen 408. These additional blood flow valves would also be substantially identical to the blood flow valves 62 and 70 which were described hereinabove with regard to the catheter system 16.

Referring again to FIGS. 20–21 and also to FIG. 22, the original catheter 404 (and the replacement catheter 406) defines the lumen 405 through which blood is advanced. The lumen 405 defines a distal orifice 426. The distal orifice 426 is defined in a distal segment 428 of the original catheter 404 (and the replacement catheter 406).

A clamp 430 is positioned on the original catheter 404 (and the replacement catheter 406). Another clamp 431 is positioned on the guide catheter 402 as shown in FIG. 20 and 21. The clamps 430, 431 are substantially identical in construction and function to the clamps 82, 84 discussed hereinabove with regard to the catheter system 16.

The original catheter 404 (and the replacement catheter 406) may be positioned within the guide lumen 410 of the guide catheter 402 as shown in FIG. 20. When the original catheter 404 (or alternatively the replacement catheter 406) is positioned within the guide lumen 410 as shown in FIG. 20, the original catheter 404 (or alternatively the replacement catheter 406) is said to be positioned in an "inserted position." When the original catheter 404 (or alternatively the replacement catheter 406) is entirely removed from the guide lumen 410, the original catheter 404 (or alternatively the replacement catheter 406) is said to be positioned in a "removed position."

When the original catheter 404 (and the replacement catheter 406) is positioned in the inserted position, the distal segment 428 of the original catheter 404 (and the replacement catheter 406) extends out of the distal guide orifice 414 of the guide catheter 402 as shown in FIG. 20. Accordingly, the distal orifice 426 is positioned outside of the guide lumen 410 when the original catheter 404 (and the replacement catheter 406) is located in its inserted position.

Moreover, when the original catheter 404 (and the replacement catheter 406) is located in the inserted position, the threaded cap 420 is positioned adjacent to the set of external threads 418 such that the threaded cap 420 can be rotated relative to guide catheter 402 so as to lock the original catheter 404 (and the replacement catheter 406) to the guide catheter 402.

The guide catheter 402 is placed within the body 46 in substantially the same manner as was described hereinabove with respect to the placement of the guide catheter 32 of the catheter system 16 within the body 46 (i.e. by the tunneled catheter technique). Once the guide catheter 402 is placed in the body 46 as described above, the original catheter 404 is advanced through the guide lumen 410 of the guide catheter 402 so that the distal orifice 426 is advanced out of the distal guide orifice 414 and positioned within the superior vena cava 30 of the body 46. (In other words, the original catheter 404 is advanced to its inserted position.) The original catheter 404 is then respectively locked to the guide catheter 402 in the manner which has been previously described hereinabove.

Figure 23:
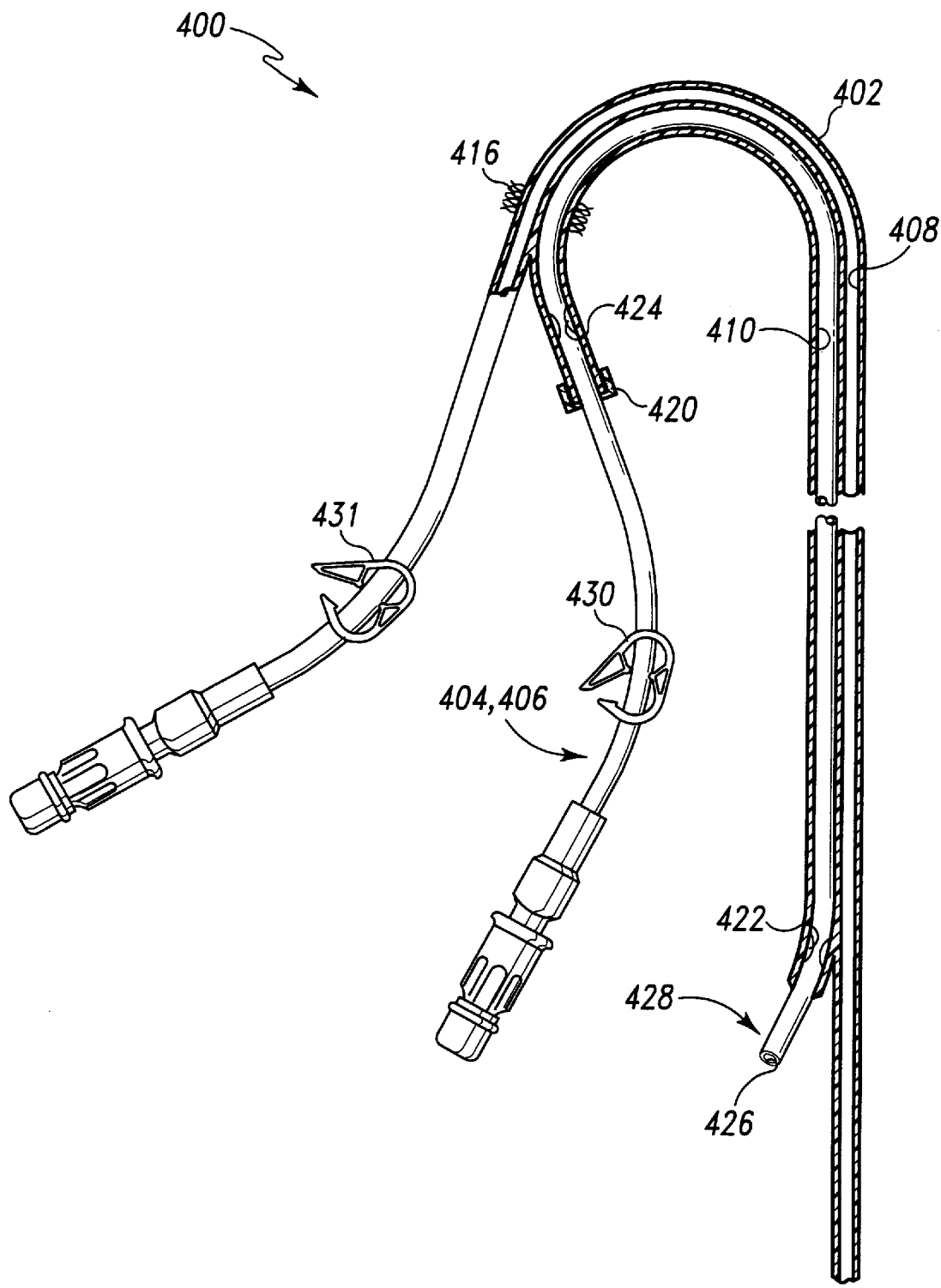
FIG. 23 is a view similar to FIG. 20, but showing another catheter system which incorporates the features of the present invention therein.

The catheter system 400 is shown in FIGS. 20 and 21 as having the distal segment of the guide lumen 410 located adjacent to the active lumen 408. In the embodiment shown in FIGS. 20 and 21, the guide catheter 402 can be said to possess a side-by-side configuration. An alternative to providing the guide catheter 402 with a side-by-side configuration is shown in FIGS. 23. In particular, a distal portion of both the guide lumen 410 and the active lumen 408 of the catheter system 400 may be alternatively configured so that the distal portion of the guide catheter 402 is arranged in a bifurcated configuration as shown in FIG. 23. In such a configuration, the distal portion of the guide lumen 410 is arranged so as to gradually extend away from the distal portion of the active lumen 408 as shown in FIG. 23. In the embodiment shown in FIG. 23, the guide catheter 402 can be said to possess a "split-tip" configuration.

Figure 24:
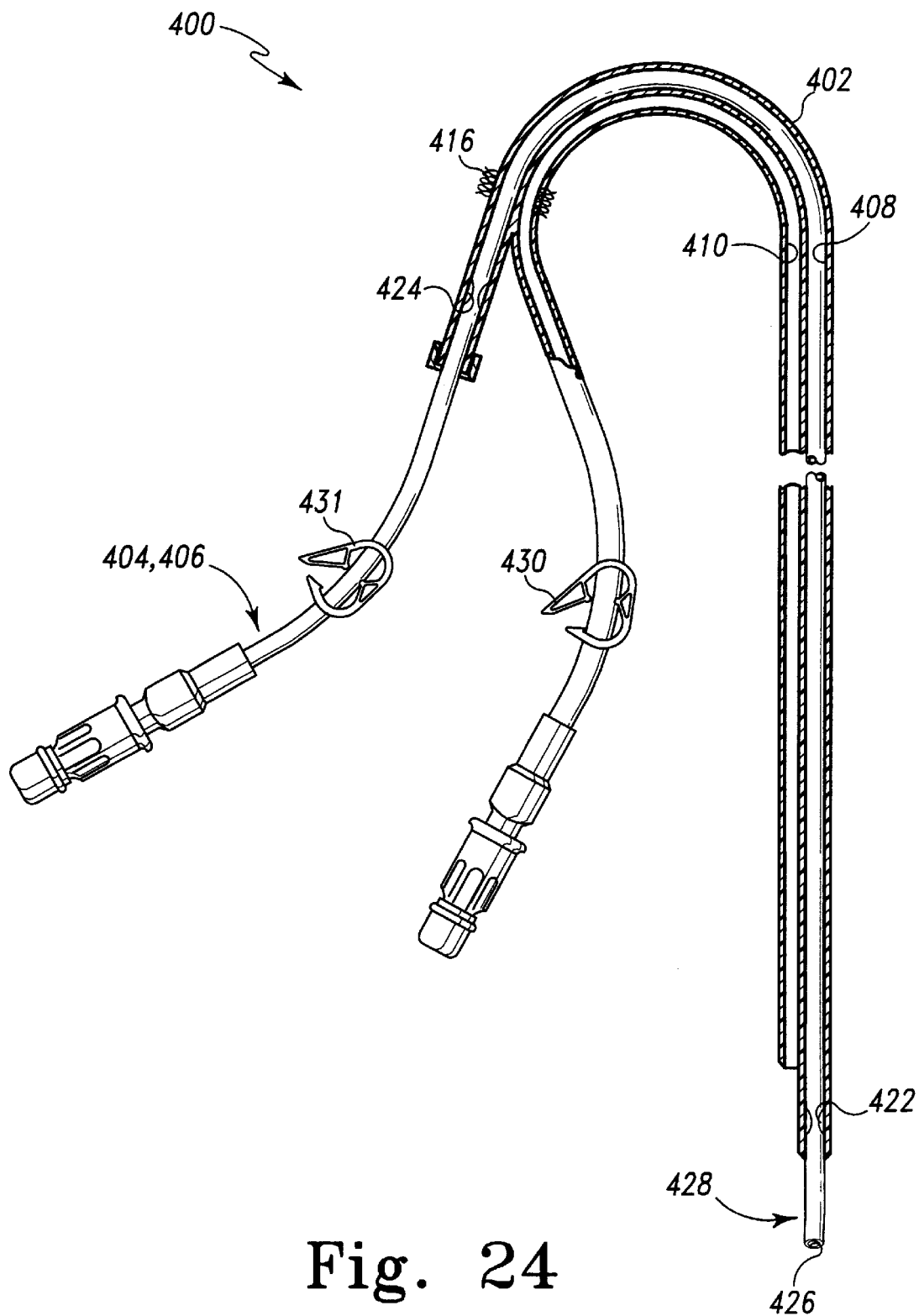
FIG. 24 is a view similar to FIG. 20, but showing still another catheter system which incorporates the features of the present invention therein.

In addition, the catheter system 400 is shown in FIGS. 20 and 21 as having the original catheter 404 (and the replacement catheter 406) positionable within the guide lumen 410 of the guide catheter 402 while the active lumen 408 does not receive any such catheter therein. In an alternative embodiment of the present invention which is shown in FIG. 24, the catheter system 400 may be modified such that the original catheter 404 (and the replacement catheter 406) would be positionable within the lumen 408 of the guide catheter 402 while the lumen 410 would not receive any such catheter therein. In such an embodiment, the lumen 410 would function to advance a fluid therethrough, such as blood.

IV(a). First Manner of Using Catheter System 400

According to a first preferred manner of using the catheter system 400, the original catheter 404 is replaced with the replacement catheter 406 only after it becomes substantially inoperative due to partial or total occlusion of its lumen 405 as a result of, for example, blood clot build-up. Such a manner of using the catheter system 400 would be substantially similar to the manner of using the catheter system 16 which was discussed herein in section 1(a) entitled "First Manner of Using Catheter System 16".

IV(b). Second Manner of Using Catheter System 400

In accordance with a second preferred manner of using the catheter system 400, the original catheter 404 is a "single use" catheter. In other words, the original catheter 404 of catheter system 400 is only used for a single dialysis session, and thereafter discarded. Hence, the original catheter 404 would typically never be left in the vascular system 22 long enough to become substantially inoperative due to partial or total occlusion of its lumen 405 as a result of, for example, blood clot build-up. Such a manner of using the catheter system 400 would be substantially similar to the manner of using the catheter system 16 which was discussed herein in section 1(b) entitled "Second Manner of Using Catheter System 16".

Note that between dialysis sessions, when the original catheter 404 (or the replacement catheter 406) is not located within the guide lumen 410 of the guide catheter 402, a closure member 432, such as a cap, is secured to the guide catheter 402 so as to cover the proximal guide orifice 412. The closure member 432 is substantially identical in construction and function to the closure member 100 of the catheter system 16 shown in FIGS. 11–13. Optionally, a clamp (not shown) which is similar in construction and function to the clamp 101 of the catheter system 16 (see FIG. 11) may also be positioned on the branch of the guide catheter 402 near the proximal guide orifice 412 between dialysis sessions.

Of course, when the patient desires to be dialyzed again, the guide catheter 402 is prepped in a sterile manner such as by applying an anti-bacterial solution thereto. Thereafter, the closure member 432 would be unlocked from the guide catheter 402, and thereafter the replacement catheter 406 would be inserted into the guide lumen 410 and then locked to the guide catheter 402 as hereinabove described. Again, this manner of using the catheter system 400 would be substantially similar to the manner of using the catheter system 16 which was discussed herein in section 1(b) entitled "Second Manner of Using Catheter System 16".

Also, please note that according to the second manner of using the catheter system 400, the original catheter 404 and the replacement catheter 406 are only a "single use" catheter. Accordingly, the physical structure of the catheters 404, 406 of the catheter system 400 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

IV(c). Third Manner of Using Catheter System 400

According to a third preferred manner of using the catheter system 400, the original catheter 404 is replaced with the replacement catheter 406 after any predetermined number of dialysis sessions is performed. For example, such predetermined number may be (i) determined from experimental studies, (ii) determined based on patient history, or (iii) determined based on other criteria. Such a manner of using the catheter system 400 would be substantially similar to the manner of using the catheter system 16 which was discussed herein in section 1(c) entitled "Third Manner of Using Catheter System 16".

V. Catheter System 500

Figure 25:
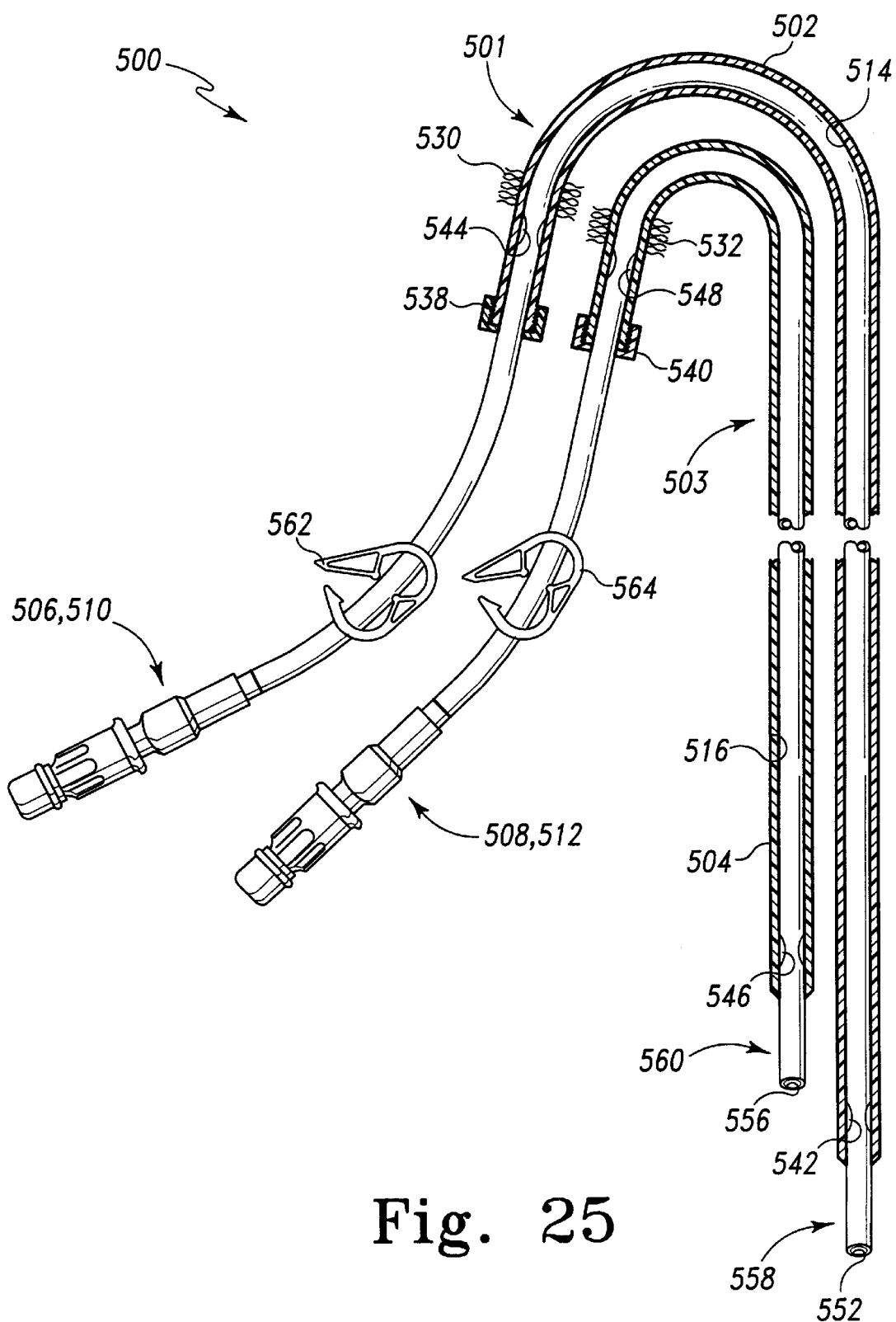
FIG. 25 is a view similar to FIG. 3, but showing yet another catheter system which incorporates the features of the present invention therein.

FIG. 25 shows a catheter system 500 which further incorporates the features of the present invention therein. The catheter system 500 includes a first catheter apparatus 501 and a second catheter apparatus 503. The first catheter apparatus 501 includes a first guide catheter 502 and a first original single lumen catheter 506, while the second catheter apparatus 503 includes a second guide catheter 504 and a second original single lumen catheter 508. The first catheter apparatus 501 further includes a first replacement single lumen catheter 510 as will be discussed below, and the second catheter apparatus further includes a second replacement single lumen catheter 512 as also will be described below.

Figure 26:
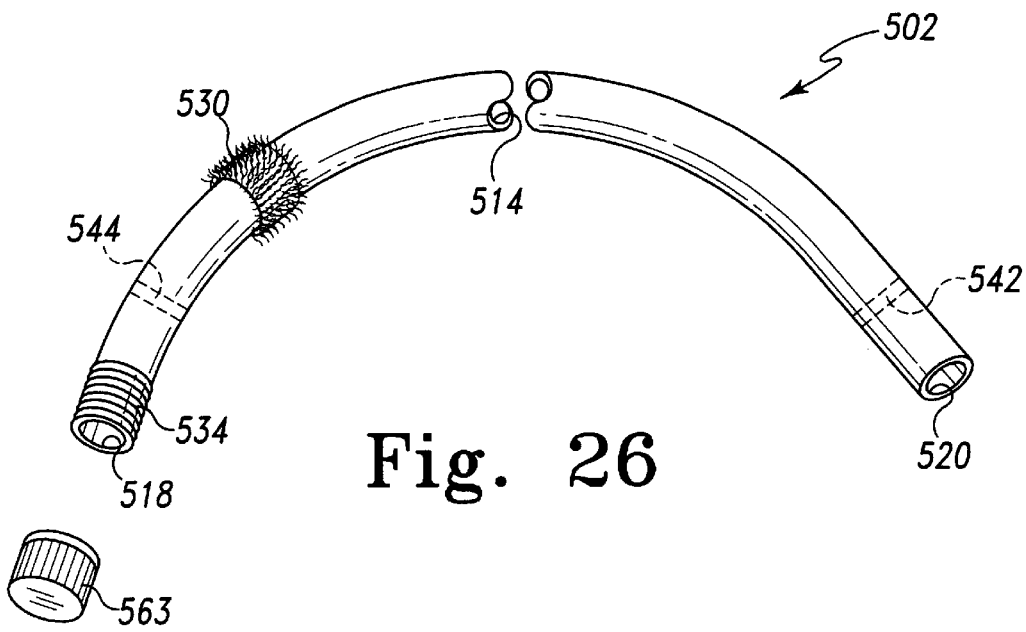
FIG. 26 is a side elevational view of the first guide catheter of the catheter system shown in FIG. 25.
Figure 27:
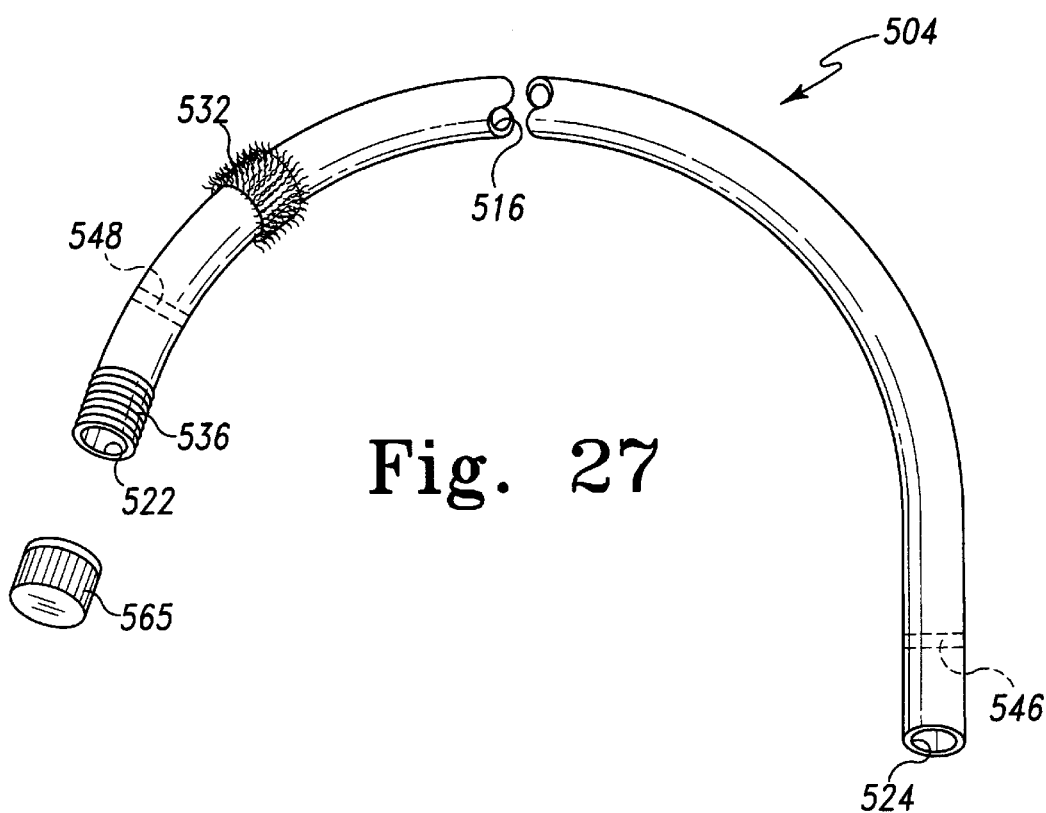
FIG. 27 is a side elevational view of the second guide catheter of the catheter system shown in FIG. 25.

The first guide catheter 502 has a first guide lumen 514 defined therein which extends along the length of the guide catheter 502 as shown in FIGS. 25 and 26. The second guide catheter 504 has a second guide lumen 516 defined therein which extends along the length of the guide catheter 504 as also shown in FIGS. 25 and 27. The first guide lumen 514 defines a first proximal guide orifice 518 and a first distal guide orifice 520, while the second guide lumen 516 defines a second proximal guide orifice 522 and a second distal guide orifice 524.

The first original catheter 506 is able to be positioned within the guide lumen 514 of the guide catheter 502, while the second original catheter 508 is able to be positioned within the guide lumen 516 of the guide catheter 504 as shown in FIG. 25. Similarly, the first replacement catheter 510 is also able to be positioned within the guide lumen 514 of the guide catheter 502, while the second replacement catheter 512 is also able to be positioned within the guide lumen 516 of the guide catheter 504 as shown in FIG. 25.

Figure 28:
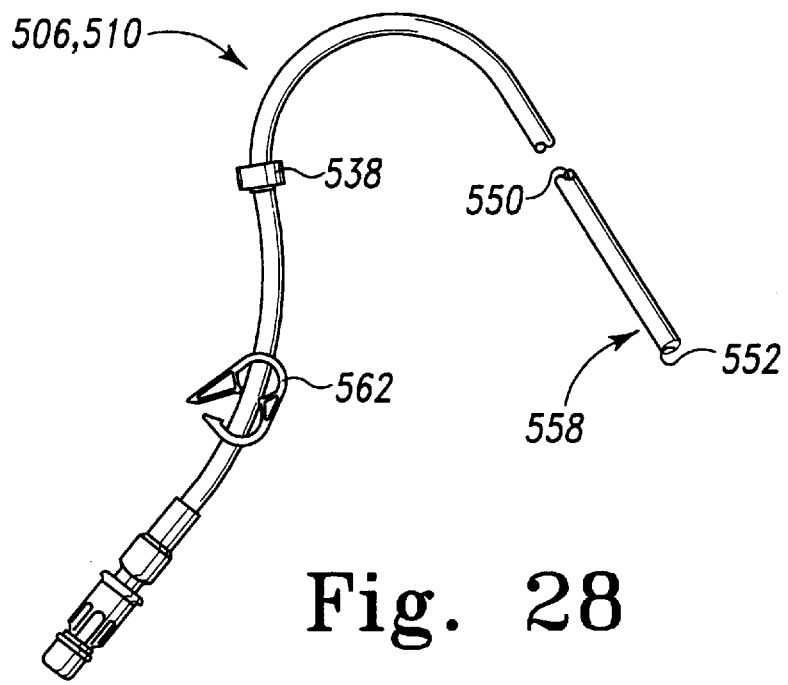
FIG. 28 is a side elevational view of the first original catheter of the catheter system shown in FIG. 25.
Figure 29:
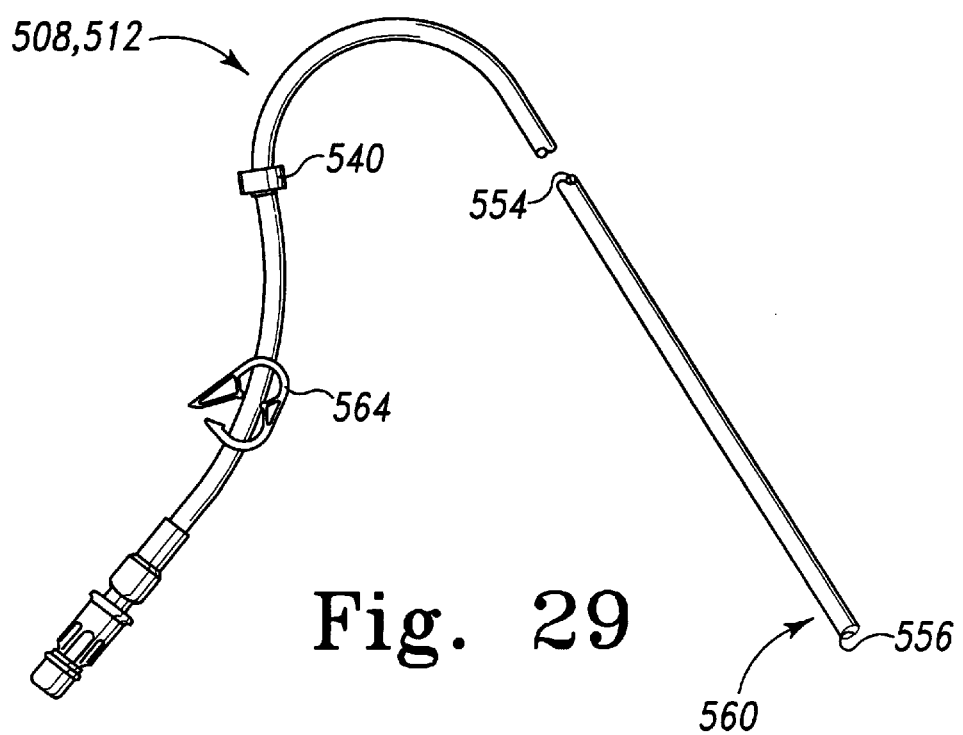
FIG. 29 is a side elevational view of the second original catheter of the catheter system shown in FIG. 25.

Note that the first original catheter 506 possesses the same physical construction and configuration as the first replacement catheter 510, and similarly the second original catheter 508 possesses the same physical construction and configuration as the second replacement catheter 512. Thus, for convenience of description, FIGS. 25, 28, and 29 show (i) reference numerals 506 and 510 identifying the same catheter, and (ii) reference numerals 508 and 512 identifying the same catheter. However, the first original catheter 506 will be located within the first guide lumen 514 during a first period of time, while the first replacement catheter 510 will be located within the first guide lumen 514 during a second period of time which is after the first period of time. Similarly, the second original catheter 508 will be located within the second guide lumen 516 during a first period of time, while the second replacement catheter 512 will be located within the second guide lumen 516 during a second period of time which is after the first period of time.

In particular, according to one preferred manner of using the catheter system 500 during a medical procedure, such as a dialysis session, the first original catheter 506 and the second original catheter 508 are respectively positioned within the first guide lumen 514 of the guide catheter 502 and the second guide lumen 516 of the guide catheter 504 for a first period of time during which blood is infused and withdrawn therethrough. After the first period of time, the blood flow through the lumens of the first original catheter 506 and the second original catheter 508 may become partially or even totally inhibited due to, for example, blood clot build-up. In order to remedy this problem, the first original catheter 506 and the second original catheter 508 are respectively withdrawn from the first guide lumen 514 and the second guide lumen 516, and thereafter, the first replacement catheter 510 and the second replacement catheter 512 are respectively positioned within the first guide lumen 514 and the second guide lumen 516 for a subsequent second period of time during which blood is again infused and withdrawn therethrough.

Referring again to FIGS. 25, 26, 27 and 30, the first guide catheter 502 has a tissue ingrowth member 530 secured to an outer surface thereof, while the second guide catheter 504 has a tissue ingrowth member 532 secured to an outer surface thereof. Tissue ingrowth members 530, 532 are substantially identical to tissue ingrowth member 38 described hereinabove with regard to the catheter system 16.

As shown in FIGS. 26 and 27, the first guide catheter 502 includes a first set of external threads 534 defined on an outer surface thereof near the first proximal guide orifice 518, while the second guide catheter 504 includes a second set of external threads 536 defined on an outer surface thereof near the second proximal guide orifice 522. The first set of external threads 534 cooperate with a first internally threaded cap 538 of the first original catheter 506 (and the first replacement catheter 510) to lock the first original catheter 506 (and the first replacement catheter 510) to the first guide catheter 502 as shown in FIG. 25.

Similarly, the second set of external threads 536 cooperate with a second internally threaded cap 540 of the second original catheter 508 (and the second replacement catheter 512) to lock the second original catheter 508 (and the second replacement catheter 512) to the second guide catheter 504 as also shown in FIG. 25. The caps 538, 540 are substantially identical to the cap 67 which was described hereinabove with regard to catheter system 16. Moreover, each of the catheters 506, 508 (and 510, 512) are provided with an upper tab and a lower tab, similar to tabs 68, 69 of the catheter system 16 described above (see FIG. 6), to rotatably retain the caps 538, 540 in place.

While the original catheters 506, 508 and the replacement catheters 510, 512 are described as being respectively locked to the guide catheters 502, 504 using a locking arrangement which utilizes cooperating internal and external threads, and has substantial benefits thereby, numerous other arrangements may alternatively be incorporated into the dialysis system 500 to function to lock the original catheters 506, 508 and the replacement catheters 510, 512 to the guide catheters 502, 504 and still achieve many of the advantages of the present invention. For example, the detent and groove type locking arrangement (not shown) or the leg and guide channel type locking arrangement (not shown) which were described above in regard to catheter system 16 may be utilized to respectively lock the original catheters 506, 508 and the replacement catheters 510, 512 to the guide catheters 502, 504.

The first guide catheter 502 further includes a distal blood flow valve 542 and a proximal blood flow valve 544 positioned within the first guide lumen 514 as shown in FIGS. 25 and 26. The second guide catheter 504 further includes a distal blood flow valve 546 and a proximal blood flow valve 548 positioned within the second guide lumen 516 as also shown in FIGS. 25 and 26. The blood flow valves 542, 544, 546, and 548 are substantially identical to the blood flow valves 62 and 70 which were described hereinabove with regard to the catheter system 16.

Referring again to FIGS. 25, 28, 29, and 30, the first original catheter 506 (and the first replacement catheter 510) includes a lumen 550. The lumen 550 defines a distal orifice 552. Similarly, the second original catheter 508 (and the second replacement catheter 512) includes a lumen 554. The lumen 554 defines a distal orifice 556. The distal orifice 552 is defined in a distal segment 558 of the first original catheter 506 (and the first replacement catheter 510). Similarly, the distal orifice 556 is defined in a distal segment 560 of the second original catheter 508 (and the second replacement catheter 512).

A clamp 562 is positioned on the first original catheter 506 (and the first replacement catheter 510), while another clamp 564 is positioned on the second original catheter 508 (and the second replacement catheter 512). The clamps 562, 564 are substantially identical in construction and function to the clamps 82, 84 discussed hereinabove with regard to the catheter system 16.

The first original catheter 506 (and the first replacement catheter 510) may be positioned within the first guide lumen 514 of the guide catheter 502, while the second original catheter 508 (and the second replacement catheter 512) may be positioned within the second guide lumen 516 of the second guide catheter 504 as shown in FIG. 25. When the first original catheter 506 (or alternatively the first replacement catheter 510) is positioned within the first guide lumen 514 as shown in FIG. 25, the first original catheter 506 (or alternatively the first replacement catheter 510) is said to be positioned in an "inserted position." Similarly, when the second original catheter 508 (or alternatively the second replacement catheter 512) is positioned within the second guide lumen 516 as shown in FIG. 25, the second original catheter 508 (or alternatively the second replacement catheter 512) is also said to be positioned in an "inserted position." When the first original catheter 506 (or alternatively the first replacement catheter 510) is entirely removed from the first guide lumen 514, the first original catheter 506 (or alternatively the first replacement catheter 510) is said to be positioned in a "removed position." Similarly, when the second original catheter 508 (or alternatively the second replacement catheter 512) is entirely removed from the second guide lumen 516, the second original catheter 508 (or alternatively the second replacement catheter 512) is also said to be positioned in a "removed position."

When the first original catheter 506 (and the first replacement catheter 510) is positioned in the inserted position, the distal segment 558 of the first original catheter 506 (and the first replacement catheter 510) extends out of the first distal guide orifice 520 of the guide catheter 502 as shown in FIG. 25. Similarly, when the second original catheter 508 (and the second replacement catheter 512) is positioned in the inserted position, the distal segment 560 of the second original catheter 508 (and the second replacement catheter 512) extends out of the distal guide orifice 524 of the guide catheter 504 as shown in FIG. 25. Accordingly, the distal orifices 552, 556 are each respectively positioned outside of the guide lumens 514, 516 when the first original catheter 506 (and the first replacement catheter 510) and the second original catheter 508 (and the second replacement catheter 512) are located in their inserted position.

Moreover, when the first original catheter 506 (and the first replacement catheter 510) is located in the inserted position, the threaded cap 538 is positioned adjacent to the first set of external threads 534 such that the threaded cap 538 can be rotated relative to the first guide catheter 502 so as to lock the first original catheter 506 (and the first replacement catheter 510) to the first guide catheter 502.

Similarly, when the second original catheter 508 (and the second replacement catheter 512) is located in the inserted position, the threaded cap 540 is positioned adjacent to the second set of external threads 536 such that the threaded cap 540 can be rotated relative to the second guide catheter 504 so as to lock the second original catheter 508 (and the second replacement catheter 512) to the second guide catheter 504.

The first guide catheter 502 is placed within the body 46 in substantially the same manner as was described hereinabove with respect to the placement of the guide catheter 32 of the catheter system 16 within the body 46 (i.e. by the tunneled catheter technique). Similarly, the second guide catheter 504 is placed within the body 46 in substantially the same manner as was described hereinabove with respect to the placement of the guide catheter 32 of the catheter system 16 within the body 46 (i.e. by the tunneled catheter technique). Once the first guide catheter 502 and the second guide catheter 504 are placed in the body 46 as described above, the first original catheter 506 and the second original catheter 508 are respectively advanced through the first guide lumen 514 of the guide catheter 502 and the second guide lumen 516 of the guide catheter 504 so that the distal orifices 552, 556 are respectively advanced out of the distal guide orifices 520, 524 and positioned within the superior vena cava 30 of the body 46. (In other words, the first original catheter 506 and the second original catheter 508 are respectively advanced to their inserted positions.) The first original catheter 506 and the second original catheter 508 are then respectively locked to the first guide catheter 502 and the second guide catheter 504 in the manner which has been previously described hereinabove.

Figure 30:
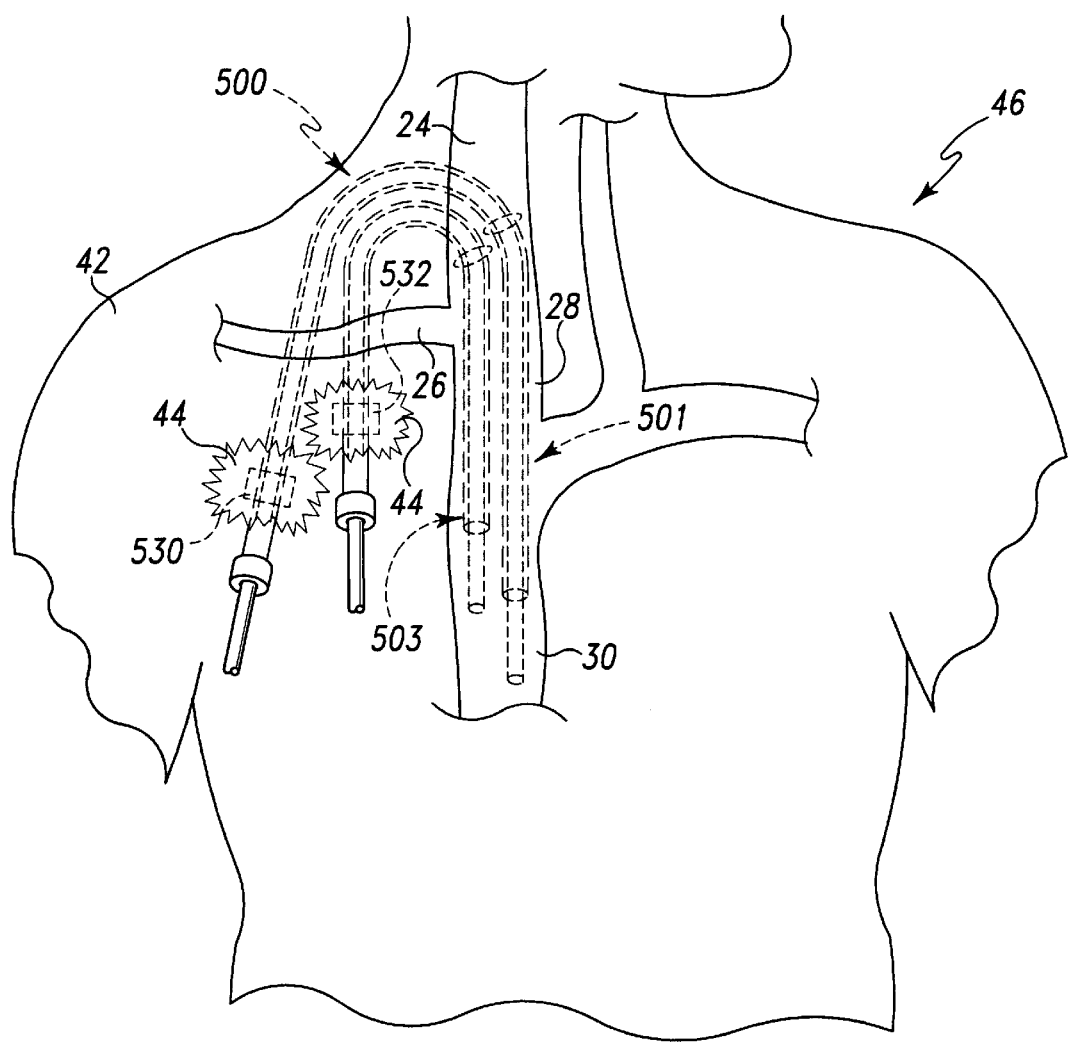
FIG. 30 is an enlarged view which is similar to FIG. 2, but showing the catheter system of FIG. 25 (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.

The catheter system 500 is shown in FIGS. 25–30 as being configured to allow removal and replacement of (i) the first original catheter 506 of the first catheter apparatus 501, as well as (ii) the second original catheter 508 of the second catheter apparatus 503. However, it should be appreciated that a first alternative arrangement (not shown) to the arrangement described in FIGS. 25–30 is to configure the second catheter apparatus 503 to be exactly the same as shown in FIGS. 25 and 30, but to configure the first catheter apparatus 501 to be similar to a conventional single lumen catheter (i.e. a catheter apparatus which does not possess a removable/replaceable inner conduit). It should be further appreciated that a second alternative arrangement (not shown) to the arrangement described in FIGS. 25–30 is to configure the first catheter apparatus 501 to be exactly the same as shown in FIGS. 25 and 30, but to configure the second catheter apparatus 503 to be similar to a conventional single lumen catheter (i.e. a catheter apparatus which does not possess a removable/replaceable inner conduit).

V(a). First Manner of Using Catheter System 500

According to a first preferred manner of using the catheter system 500, the first original catheter 506 is replaced with the first replacement catheter 510 only after it becomes substantially inoperative due to partial or total occlusion of its lumen 550 as a result of, for example, blood clot build-up. Moreover, the second original catheter 508 is replaced with the second replacement catheter 512 only after it becomes substantially inoperative due to partial or total occlusion of its lumen 554 as a result of, for example, blood clot build-up. Such a manner of using the catheter system 500 would be substantially similar to the manner of using the catheter system 16 which was discussed herein in section 1(a) entitled "First Manner of Using Catheter System 16". However, it should be noted that it is possible, and may even be likely, that the first original catheter 506 (and the first replacement catheter 510) will be replaced due to, for example, blood clot build-up at a lower frequency in comparison to the replacement of the second original catheter 508 (and the second replacement catheter 512) due to, for example, blood clot build-up. Such lower frequency of replacement may be due to the fact that during use of the catheter system 500, blood is infused into the vascular system 22 with the first original catheter 506 (and the first replacement catheter 510). In contrast, during use of the catheter system 500, blood is withdrawn from of the vascular system 22 with the second original catheter 508 (and the second replacement catheter 512). Again, historically, occlusion problems occur more frequently during a dialysis procedure when attempting to withdraw blood from a patient's vascular system through a dialysis catheter in comparison to attempting to infuse blood back into a patient's vascular system through the dialysis catheter.

V(b). Second Manner of Using Catheter System 500

In accordance with a second preferred manner of using the catheter system 500, each of the first original catheter 506 and the second original catheter 508 is a "single use" catheter. In other words, both the first original catheter 506 and the second original catheter 508 of catheter system 500 are only used for a single dialysis session, and thereafter discarded. Hence, both the first original catheter 506 and the second original catheter 508 would typically never be left in the vascular system 22 long enough to become substantially inoperative due to partial or total occlusion of its lumens 550, 554 as a result of, for example, blood clot build-up. Such a manner of using the catheter system 500 would be substantially similar to the manner of using the catheter system 16 which was discussed herein in section 1(b) entitled "Second Manner of Using Catheter System 16".

Note that between dialysis sessions, when the first original catheter 506 (or the first replacement catheter 510) is not located within the guide lumen 514 of the first guide catheter 502, a first closure member 563, such as a cap, is secured to the guide catheter 502 so as to cover the first proximal guide orifice 518. Optionally, a clamp (not shown) which is similar in construction and function to the clamp 101 of the catheter system 16 (see FIG. 11) may also be positioned on the guide catheter 502 near the first proximal guide orifice 518 between dialysis sessions. Also note that between dialysis sessions, when the second original catheter 508 (or the second replacement catheter 512) is not located within the second guide lumen 516 of the second guide catheter 504, a second closure member 565, such as another cap, is secured to the second guide catheter 504 so as to cover the second proximal guide orifice 522. Optionally, another clamp (not shown) which is similar in construction and function to the clamp 101 of the catheter system 16 (see FIG. 11) may also be positioned on the guide catheter near the second proximal guide orifice 522 between dialysis sessions. The closure members 563, 565 are substantially identical in construction and function to the closure member 100 of the catheter system 16 shown in FIGS. 11–13.

Obviously, when the patient desires to be dialyzed again, the guide catheters 502, 504 are prepped in a sterile manner such as by applying an anti-bacterial solution thereto. Thereafter, the closure members 563, 563 would be respectively unlocked from the guide catheters 502, 504, and thereafter the replacement catheters 510, 512 would be respectively inserted into the guide lumens 514, 516 and then respectively locked to the guide catheters 502, 504 as hereinabove described. Again, this manner of using the catheter system 500 would be substantially similar to the manner of using the catheter system 16 which was discussed herein in section 1(b) entitled "Second Manner of Using Catheter System 16".

Also, please note that according to the second manner of using the catheter system 500, the original catheters 506, 508 and the replacement catheters 510, 52 are only a "single use" catheters. Accordingly, the physical structure of the catheters 506, 508, 510, 512 of the catheter system 500 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

V(c). Third Manner of Using Catheter System 500

According to a third preferred manner of using the catheter system 500, the first original catheter 506 is replaced with the first replacement catheter 510, as described above, after any predetermined number of dialysis sessions is performed. Moreover, the second original catheter 508 is replaced with the second replacement catheter 512, as described above, after any predetermined number of dialysis sessions is performed. For example, such predetermined number may be (i) determined from experimental studies, (ii) determined based on patient history, or (iii) determined based on other criteria. Such a manner of using the catheter system 500 would be substantially similar to the manner of using the catheter system 16 which was discussed herein in section 1(c) entitled "Third Manner of Using Catheter System 16". In addition, the predetermined number of dialysis sessions after which the first original catheter 506 is replaced does not necessarily have to be equal to the predetermined number of dialysis sessions after which the second original catheter 508 is replaced. For example, the first original catheter 506 may be replaced with a first replacement catheter 510 after every four dialysis sessions, while the second original catheter 508 may be replaced with a second replacement catheter 512 after every three dialysis sessions.

VI. Catheter System 600

FIGS. 31–34 shows a catheter system 600 which additionally incorporates the features of the present invention therein. The catheter system 600 may be used for the administration of total parenteral nutrition (hereinafter referred to as "TPN") to a patient. TPN generally refers to a nutritive solution which is fed intravenously via an indwelling central venous catheter in conditions where patients cannot eat by mouth or receive nutrition enterally (e.g. by gastric tube or small bowel tube). Some examples where prolonged administration of TPN to a patient are indicated include instances where a patient suffers from an insufficient small bowel absorptive area such as short gut syndrome or an instance where a patient suffers from prolonged intestinal ileus which may have resulted due to a severe burn injury or an abdominal surgery. Other examples where prolonged administration of TPN to a patient are indicated include instances where a patient has a condition requiring prolonged bowel rest such as where the patient suffers from pancreatitis or inflammatory bowel disease. Yet another example where prolonged administration of TPN to a patient is indicated is the situation where a patient refuses to eat such as would occur in the case of severe anorexia nervosa.

Figure 31:
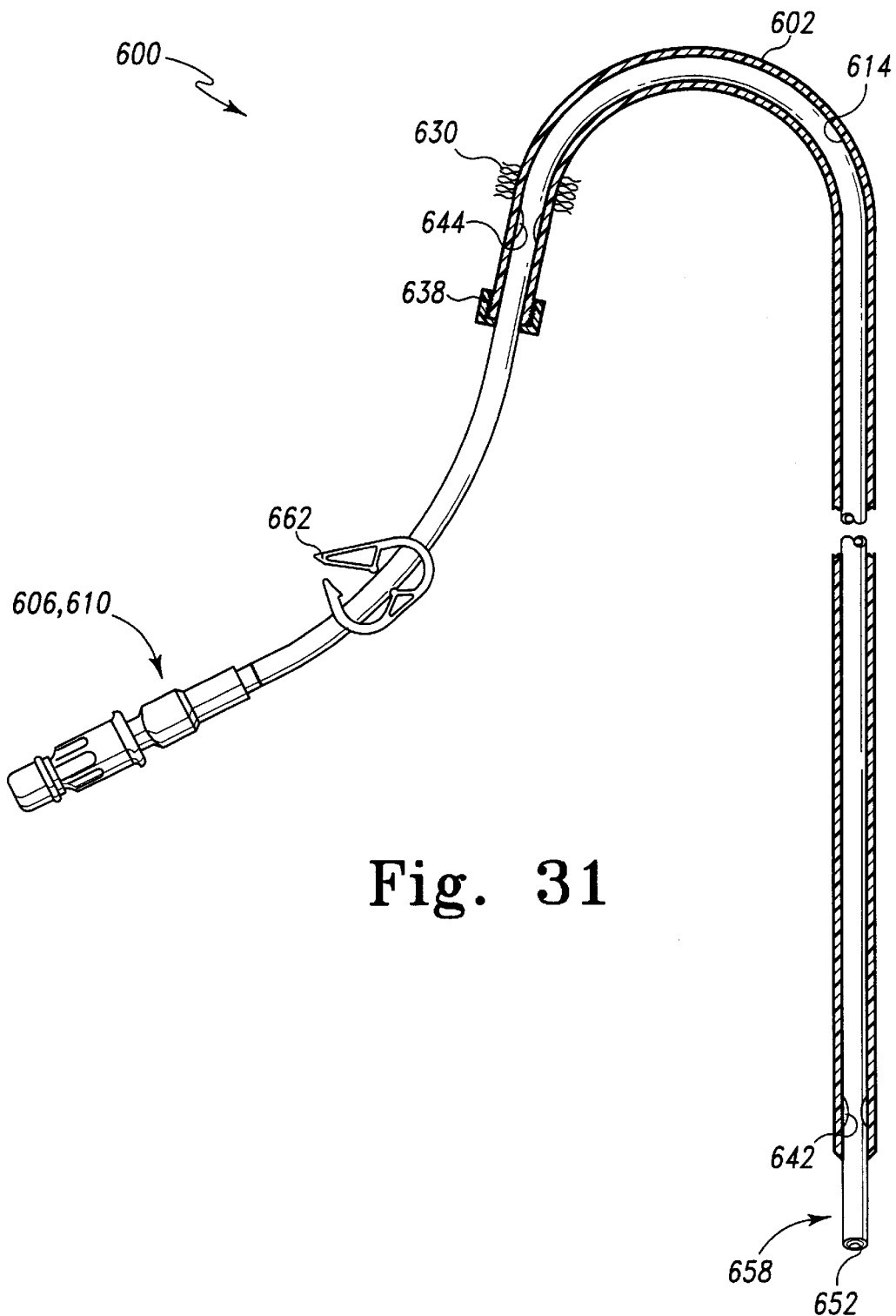
FIG. 31 is a view similar to FIG. 3, but showing still another catheter system which incorporates the features of the present invention therein.

Referring now in detail to FIGS. 31–34, the catheter system 600 includes a guide catheter 602 and an original single lumen catheter 606. The catheter system 600 further includes a replacement single lumen catheter 610 as will be discussed below. The guide catheter 602 has a guide lumen 614 which extends along the length of the guide catheter 602 as shown in FIG. 31. The guide lumen 614 defines a proximal guide orifice 618 and a distal guide orifice 620. The original catheter 606 is able to be positioned within the guide lumen 614 of the guide catheter 602 as shown in FIG. 31. Similarly, the replacement catheter 610 is also able to be positioned within the guide lumen 614 of the guide catheter 602 as shown in FIG. 31.

Figure 33:
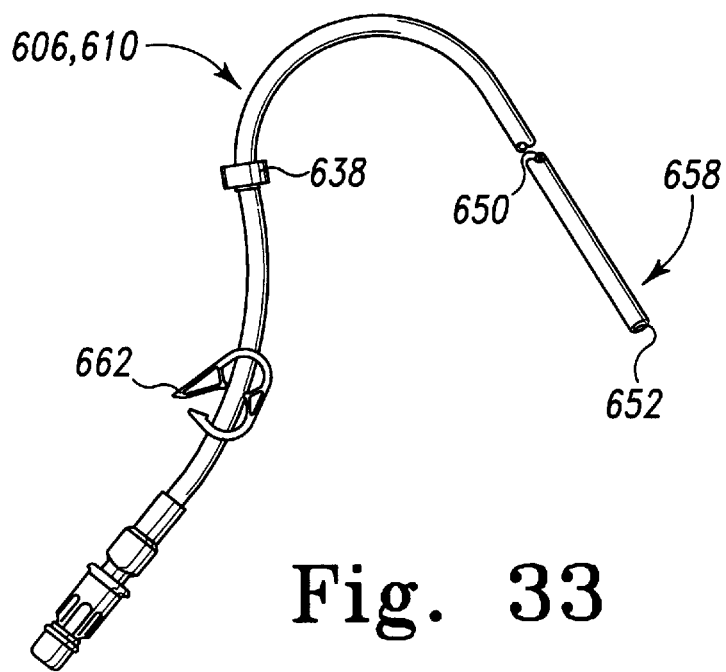
FIG. 33 is a side elevational view of the original catheter of the catheter system shown in FIG. 31.
Figure 34:
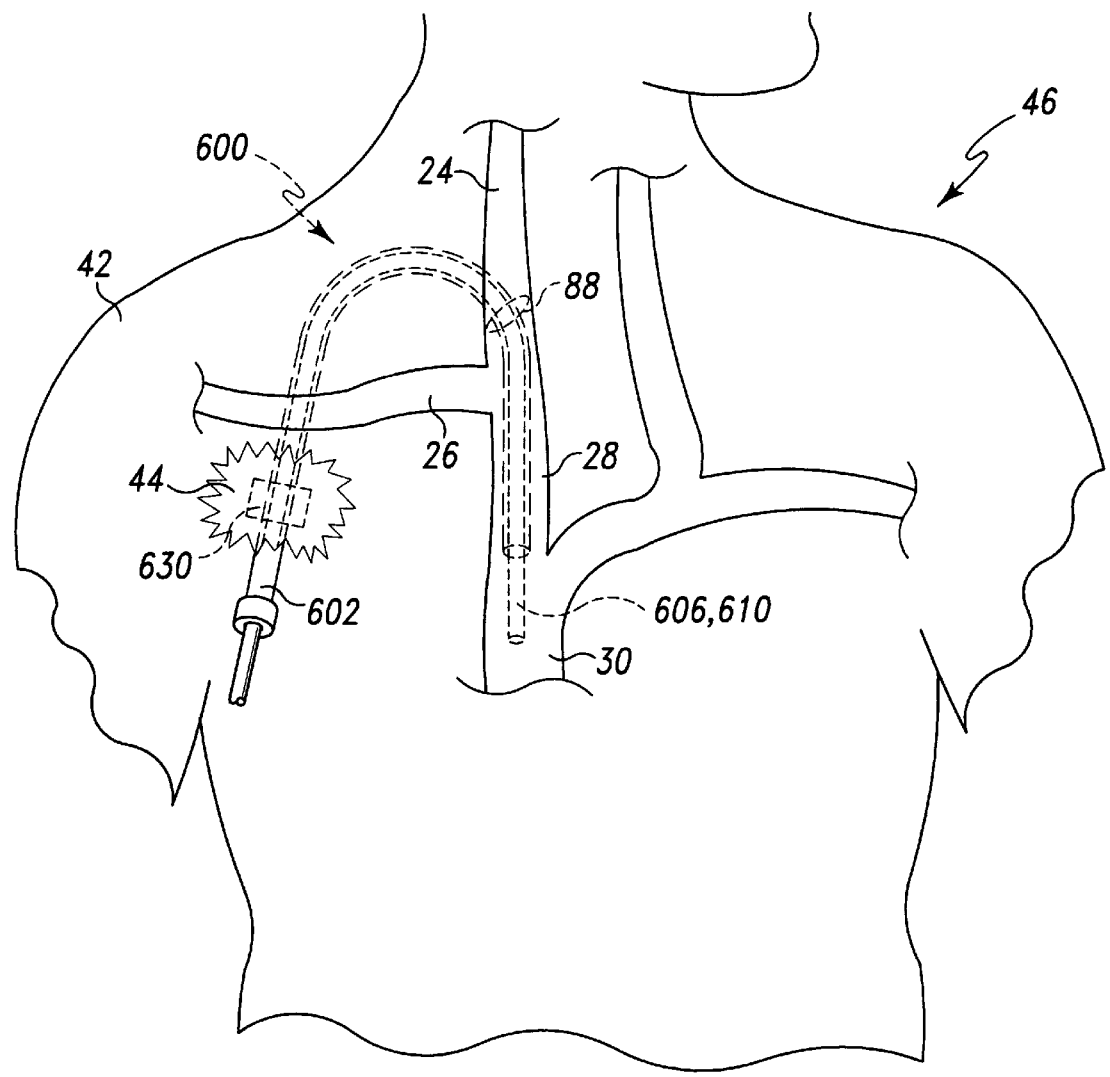
FIG. 34 is an enlarged view which is similar to FIG. 2, but showing the catheter system of FIG. 31(i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.

Note that the original catheter 606 possesses the same physical construction and configuration as the replacement catheter 610. Thus, for convenience of description, FIGS. 31, 33, and 34 show reference numerals 606 and 610 identifying the same catheter. However, the original catheter 606 will be located within the guide lumen 614 during a first period of time, while the first replacement catheter 610 will be located within the guide lumen 614 during a second period of time which is after the first period of time.

In particular, according to one preferred manner of using the catheter system 600 during a TPN administration session, the original catheter 606 is positioned within the guide lumen 614 of the guide catheter 602 for a first period of time during which TPN is infused therethrough. After the first period of time, the flow through the lumen of the original catheter 606 may become partially or even totally inhibited due to, for example, blood clot build-up. In order to remedy this problem, the original catheter 606 is withdrawn from the guide lumen 614, and thereafter, the replacement catheter 610 is positioned within the guide lumen 614 (and locked to the guide catheter 602) for a subsequent second period of time during which TPN is again infused therethrough.

Figure 32:
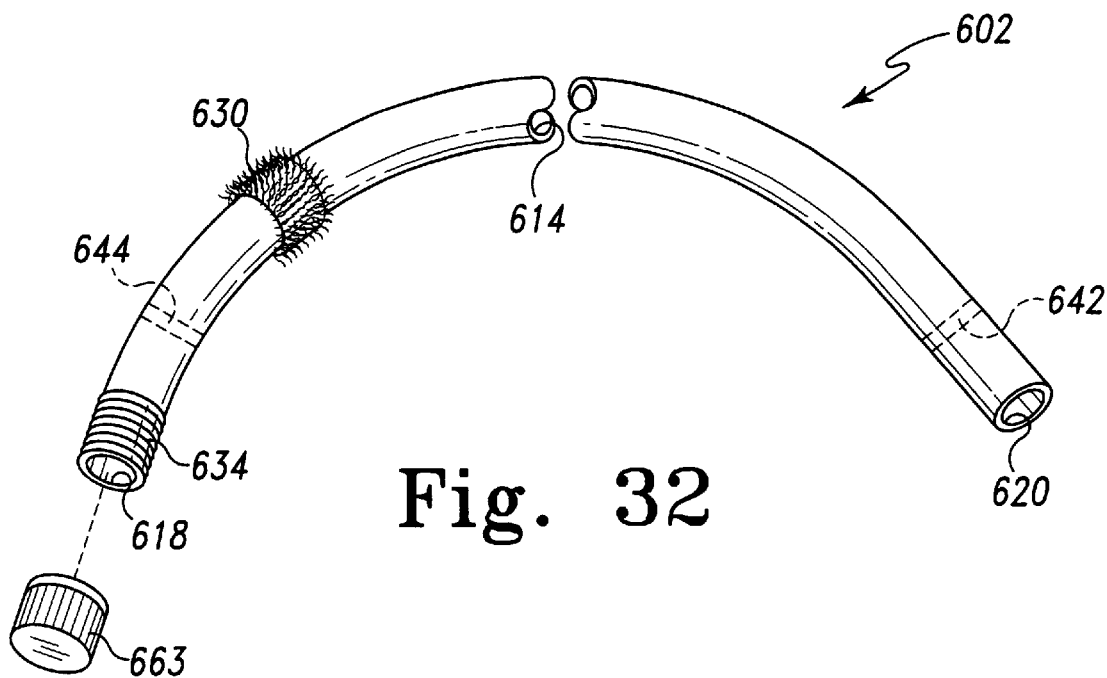
FIG. 32 is a side elevational view of the guide catheter of the catheter system shown in FIG. 31.

Referring to FIGS. 31, 32, and 34, the guide catheter 602 has a tissue ingrowth member 630 secured to an outer surface thereof. The tissue ingrowth member 630 is substantially identical to the tissue ingrowth member 38 described hereinabove with regard to the catheter system 16.

As shown in FIGS. 31 and 32, the guide catheter 602 includes a set of external threads 634 defined on an outer surface thereof near the first proximal guide orifice 618. The set of external threads 634 cooperate with an internally threaded cap 638 of the original catheter 606 (and the replacement catheter 610) to lock the original catheter 606 (and the replacement catheter 610) to the guide catheter 602 as shown in FIG. 31. The cap 638 is substantially identical to the cap 67 which was described hereinabove with regard to catheter system 16. Moreover, each of the catheters 606, 610 are provided with an upper tab and a lower tab, similar to tabs 68, 69 of the catheter system 16 described above (see FIG. 6), to rotatably retain the cap 638 in place.

While the original catheter 606 and the replacement catheter 610 are described as being respectively locked to the guide catheter 602 using a locking arrangement which utilizes cooperating internal and external threads, and has substantial benefits thereby, numerous other arrangements may alternatively be incorporated into the catheter system 600 to function to respectively lock the original catheter 606 and the replacement catheter 610 to the guide catheter 602 and still achieve many of the advantages of the present invention. For example, the detent and groove type locking arrangement (not shown) or the leg and guide channel type locking arrangement (not shown) which were described above in regard to catheter system 16 may be utilized to respectively lock the original catheter 606 and the replacement catheter 610 to the guide catheter 602.

The guide catheter 602 further includes a distal blood flow valve 642 and a proximal blood flow valve 644 positioned within the guide lumen 614 as shown in FIGS. 31 and 32. The blood flow valves 642, 644 are substantially identical to the blood flow valves 62 and 70 which were described hereinabove with regard to the catheter system 16.

Referring again to FIGS. 31, 33, and 34, the original catheter 606 (and the replacement catheter 610) includes a lumen 650. The lumen 650 defines a distal orifice 652. The distal orifice 652 is defined in a distal segment 658 of the original catheter 606 (and the replacement catheter 610).

A clamp 662 is positioned on the original catheter 606 (and the replacement catheter 610). The clamp 662 is substantially identical in construction and function to the clamps 82, 84 discussed hereinabove with regard to the catheter system 16.

The original catheter 606 (and the replacement catheter 610) may be positioned within the guide lumen 614 of the guide catheter 602 as shown in FIG. 31. When the original catheter 606 (or alternatively the replacement catheter 610) is positioned within the guide lumen 614 as shown in FIG. 31, the original catheter 606 (or alternatively the replacement catheter 610) is said to be positioned in an "inserted position." When the original catheter 606 (or alternatively the replacement catheter 610) is entirely removed from the guide lumen 614, the original catheter 606 (or alternatively the replacement catheter 610) is said to be positioned in a "removed position."

When the original catheter 606 (and the replacement catheter 610) is positioned in the inserted position, the distal segment 658 of the original catheter (and the replacement catheter 610) extends out of the distal guide orifice 620 of the guide catheter 602 as shown in FIG. 31. Accordingly, the distal orifice 652 is positioned outside of the guide lumen 614 when the original catheter 606 (and the replacement catheter 610) is located in its inserted position. Moreover, when the original catheter 606 (and the replacement catheter 610) is located in the inserted position, the threaded cap 638 is positioned adjacent to the set of external threads 634 such that the threaded cap 638 can be rotated relative to the guide catheter 602 so as to lock the original catheter 606 (and the replacement catheter 610) to the guide catheter 602.

The guide catheter 602 is placed within the body 46 in substantially the same manner as was described hereinabove with respect to the placement of the guide catheter 32 of the catheter system 16 within the body 46 (i.e. by the tunneled catheter technique). Once the guide catheter 602 is placed in the body 46 as described above, the original catheter 606 is advanced through the guide lumen 614 of the guide catheter 602 so that the distal orifice 652 is advanced out of the distal guide orifice 620 and positioned within the superior vena cava 30 of the body 46. (In other words, the original catheter 606 is advanced to its inserted position.) The original catheter 606 is then locked to the guide catheter 602 in the manner which has been previously described hereinabove.

An alternative configuration for the catheter system 600 is shown in FIG. 35. In particular, this alternative embodiment of the present invention shows a catheter system 600'. The catheter system 600' is used in substantially the same manner as herein described with respect to the catheter system 600. Moreover, the catheter system 600' is exactly the same in construction and configuration as the catheter system 600 shown in FIGS. 31–34, with the exception that the catheter system 600' includes a sideport 670 through which fluid may be withdrawn or advanced. In particular, the sideport 670 includes a conduit 672 having a set of external threads 674 defined on a proximal end thereof. A clamp 676 is positioned on the conduit 672. The clamp 662 is substantially identical in construction and function to the clamps 82, 84 discussed hereinabove with regard to the catheter system 16. The conduit 672 defines a sideport lumen 673 which is in fluid communication with the guide lumen 614. Accordingly, air can be aspirated out of the guide lumen 614 through the sideport 670 via the conduit 672. Alternatively, the guide lumen 614 may be flushed with a fluid such as a saline, heparin, or urokinase solution between uses of the catheter system 600' (e.g. administration of TPN to a patient). It should be noted that the guide lumen 614 may be even be flushed with a saline, heparin, or urokinase solution while the original catheter 606 (or the replacement catheter 610) is located within the guide lumen 614. When not in use, the sideport 670 may be clamped shut with the clamp 676. Moreover, when not in use a closure member or cap 678 may be secured to the conduit 672 to cover a proximal sideport orifice 680 which is defined by the conduit 672. The cap 678 is provided with a set of internal threads which cooperate with the set of external threads 674 so as to lock the cap 678 to the guide catheter 602. Optionally, the cap 678 may be provided with a silicone membrane 679, as shown in FIGS. 36–37, which may be traversed with a needle whereby a saline, heparin, or urokinase solution may be advanced into the conduit 72 in order to flush the guide catheter 602.

It should be noted that any of the other embodiments of the present invention set forth herein (e.g. catheter systems 16, 200, 300, 400, and 500) may be modified to incorporate a sideport which is similar to sideport 670. In particular, any of the guide catheters of the catheter systems 16, 200, 300, 400, and 500 may be modified to include a sideport which is similar in construction, configuration, and use to the construction, configuration and use of the sideport 670 described herein.

Figure 38:
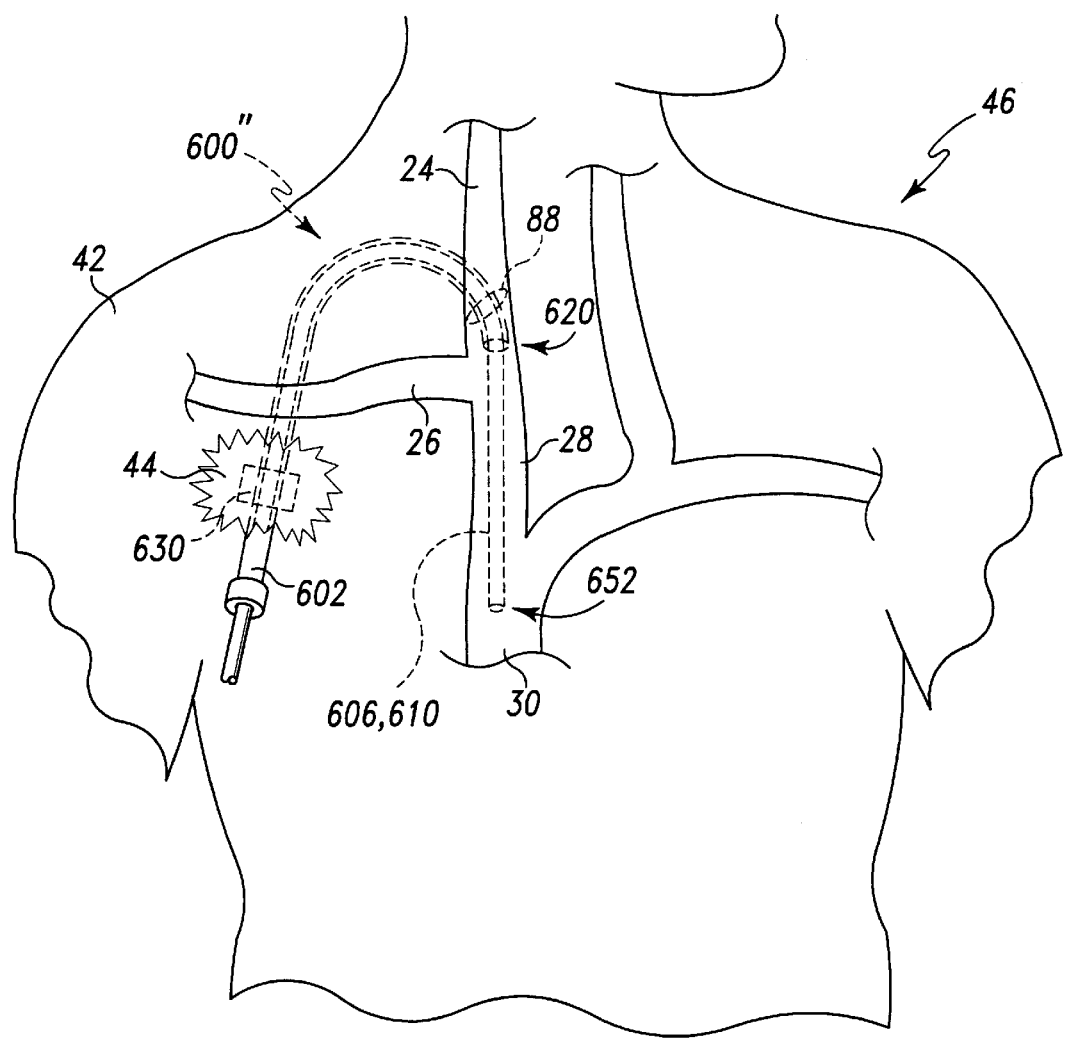
FIG. 38 is an enlarged view which is similar to FIG. 2, but showing still another catheter system which incorporates the features of the present invention therein (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.

Another alternative configuration for the catheter system 600 is shown in FIG. 38. In particular, FIG. 38 shows another catheter system 600" which also incorporates features of the present invention therein. The catheter system 600" is used in substantially the same manner as herein described with respect to the catheter system 600. Moreover, the catheter system 600" is exactly the same in construction and configuration as the catheter system 600 shown in FIGS. 31–34, with the exception that the guide lumen 602 of the catheter system 600" is much shorter in length than the guide lumen 602 of the catheter system 600, while the original catheter 606 (and replacement catheter 610) of the catheter system 600" is the same length as the original catheter 606 (and the replacement catheter 610) of the catheter system 600. (For example, compare FIG. 38 with FIG. 34). In particular, the length of the guide catheter 602 of the catheter system 600" is such that after it is placed in the body 46 as shown in FIG. 38, its distal guide orifice 620 is located in the right internal jugular vein 24 preferably approximately five centimeters distal to the venotomy 88. Moreover, in this embodiment of the present invention shown in FIG. 38, the distance between the distal orifice 652 of the original catheter 606 (and the replacement catheter 610) and the distal guide orifice 620 of the guide catheter 602 is preferably approximately fifteen centimeters. In contrast, in the embodiment shown in FIGS. 31–34, the distance between the distal orifice 652 of the original catheter 606 (and the replacement catheter 610) and the distal guide orifice 620 of the guide catheter 602 is preferably approximately three centimeters. The catheter system 600", which possesses such a relatively shorter guide catheter 602, is configured so as to eliminate the presence of a long-term intravascular catheter structure within the right innominate vein 28 and the superior vena cava 30. In particular, the only catheter structure of the catheter system 600" that remains in the vascular system 22 on a long-term basis is the distal portion of the relatively shorter guide catheter 602 which is shown in FIG. 38. This long-term intravascular catheter structure only extends within the right internal jugular vein 24 from the venotomy 88 to the distal guide orifice 620 as shown in FIG. 38. Note that the right internal jugular vein 24 is not part of a major venous return flow path for the right upper extremity of the patient's body as is the right innominate vein 28 and the superior vena cava 30. While the inner catheter 606 (or 610) does extend within the right innominate vein 28 and the superior vena cava 30 while a dialysis session is being conducted as shown in FIG. 38, such a dialysis session is typically conducted only approximately three time per week, and each session lasts for only approximately four hours. Thus, it should be appreciated that, while the guide catheter 602 of the catheter system 600" is located within the body and the patient is not engaging in a dialysis session, there exists no intravascular catheter structure present in the right innominate vein 28 and the superior vena cava 30. Note that by eliminating the presence of a long-term intravascular catheter structure from the right innominate vein 28 and the superior vena cava 30, the development of central vein stenosis due to, for example, prolonged physical contact between the intravascular catheter structure and the internal sidewall of the right innominate vein 28 and/or the internal sidewall of the superior vena cava 30 may be prevented. It should be appreciated that the fluid path which includes the right subclavian vein 26, the right innominate vein 28 and the superior vena cava 30 represents a major venous return flow path, especially in the case where an arteriovenous fistula has been created or an arteriovenous dialysis graft has been implanted in the right upper extremity of the patient's body. Preventing central venous stenosis within such a major venous return flow path is quite beneficial to a patient, e.g. a dialysis patient.

It should be noted that any of the guide catheters of the catheter systems 16, 200, 300, 400, 500, and 600' may be modified to include a guide catheter which is similar in construction, configuration, and use to the construction, configuration and use of the guide catheter 602 of the catheter system 600" described herein. In particular, any of the other embodiments of the catheter systems of the present invention set forth herein (e.g. catheter systems 16, 200, 300, 400, 500, 600') may be modified to incorporate a relatively short guide catheter similar to the guide catheter 602 of the catheter system 600" (shown in FIG. 38) whereby (i) the distance between its distal orifice of the original catheter (and the replacement catheter) and its distal guide orifice of the guide catheter is preferably approximately fifteen centimeters, and (ii) the length of such shorter guide catheter is such that after it is placed in the body 46, its distal guide orifice of the guide catheter is located in the right internal jugular vein 24 preferably approximately five centimeters distal to the venotomy 88.

VI(a). First Manner of Using Catheter System 600

According to a first preferred manner of using the catheter system 600, the original catheter 606 is replaced with the replacement catheter 610 only after it becomes substantially inoperative due to partial or total occlusion of its lumen 650. Such a manner of using the catheter system 600 would be substantially similar to the manner of using the catheter system 16 which was discussed herein in section 1(a) entitled "First Manner of Using Catheter System 16".

VI(b). Second Manner of Using Catheter System 600

In accordance with a second preferred manner of using the catheter system 600, the original catheter 606 is a "single use" catheter. In other words, the original catheter 606 of the catheter system 600 is only used for a single TPN administration session, and thereafter discarded. Hence, the original catheter 606 would typically never be left in the vascular system 22 long enough to become substantially inoperative due to partial or total occlusion of its lumen 650. Such a manner of using the catheter system 600 would be substantially similar to the manner of using the catheter system 16 which was discussed herein in section 1(b) entitled "Second Manner of Using Catheter System 16".

Note that between TPN administration sessions, when the original catheter 606 (and the replacement catheter 610) is not located within the guide lumen 614 of the guide catheter 602, a first closure member 663, such as a cap, is secured to the guide catheter 602 so as to cover the proximal guide orifice 618. The closure member 663 is substantially identical in construction and function to the closure member 100 of the catheter system 16 shown in FIGS. 11–13. Optionally, a clamp (not shown) which is similar in construction and function to the clamp 101 of the catheter system 16 (see FIG. 11) may also be positioned on the guide catheter 602 near the proximal guide orifice 618 between TPN administration sessions.

When the patient desires to engage in another TPN administration session, the guide catheter 602 is prepped in a sterile manner such as by applying an antibacterial solution thereto. Thereafter, the closure member 663 would be unlocked from the guide catheter 602, and thereafter the replacement catheter 606 would be inserted into the guide lumen 614 and then locked to the guide catheter 602 as hereinabove described. Again, this manner of using the catheter system 600 would be substantially similar to the manner of using the catheter system 16 which was discussed herein in section 1(b) entitled "Second Manner of Using Catheter System 16".

Also, please note that according to the second manner of using the catheter system 600, the original catheter 606 and the replacement catheter 610 are only "single use" catheters. Accordingly, the physical structure of the catheters 606, 610 of the catheter system 600 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

VI(c). Third Manner of Using Catheter System 600

According to a third preferred manner of using the catheter system 600, the original catheter 606 is replaced with the replacement catheter 610 after any predetermined number of TPN administration sessions is performed. For example, such predetermined number may be (i) determined from experimental studies, (ii) determined based on patient history, or (iii) determined based on other criteria. Such a manner of using the catheter system 600 would be substantially similar to the manner of using the catheter system 16 which was discussed herein in section 1(c) entitled "Third Manner of Using Catheter System 16".

VII. Conclusion

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

For instance, while the above-described dual-lumen catheter systems (e.g. catheter systems 16, 200, 300, 400, and 500) were discussed as being effective to perform hemodialysis, such catheter systems can also be utilized to perform other medical procedures in which dual-lumen catheter access to the vascular system (e.g. the central venous system) is required. One example of such a medical procedure is plasmapheresis in which blood is withdrawn from the vascular system, components of the blood are separated outside of the body, and a portion of the blood components are then returned to the vascular system.

In addition, another medical procedure which may be performed using the above-described dual-lumen catheter systems is peritoneal dialysis. In particular, catheter occlusion may occur during peritoneal dialysis, and such occlusion may be eliminated in a manner similar to that described above with respect to the catheter systems 16, 200, 300, 400, and 500.

Moreover, while the above-described single-lumen catheter systems (e.g. catheter systems 600, 600', 600") were discussed as being effective to perform administration of total parenteral nutrition, such catheter systems can be utilized to perform other medical procedures in which single-lumen catheter access to the vascular system is required. Examples of other medical procedures in which single-lumen catheter access to the vascular system is required includes (i) chemotherapy or other long-term medicinal infusions, (ii) repetitive blood transfusions, and (iii) repetitive blood samplings.

Furthermore, each of the above-described catheter systems (e.g. catheter systems 16, 200, 300, 400, 500, 600, 600', 600") were described as having a tissue ingrowth member (e.g. tissue ingrowth members 38, 320, 416, 530, 630) which is configured to facilitate attachment of such catheter system to the subcutaneous tissue 44 of the body. While the provision of such a tissue ingrowth member to effect attachment of such catheter system to the body of a patient has many advantages, the present invention may utilize other mechanisms which can function to attach such catheter system to the body on a long-term or even a short-term basis and still benefit from various advantages of the other features of the present invention. An example of such an attachment mechanism is a plastic member having a hole or recess for receiving a catheter therein and further having one or more wing-like or flap-like extensions which may be sutured or taped to the skin of the patient 46. Additionally, it is possible that the above-described catheters systems of the present invention (e.g. catheter systems 16, 200, 300, 400, 500, 600, 600', 600") may not include any mechanism which specifically functions to attach the catheter systems to the body yet still benefit from some of the advantages of the other features of the present invention.

Additionally, while each of the closure members 100, 350, 352, 432, 563, 565, 663, and 678 is disclosed as being locked to a respective guide catheter or sideport by an arrangement which includes cooperating internal and external threads and has advantages thereby, such closure members 100, 350, 352, 432, 563, 565, 663, and 678 may be locked to the respective guide catheter or sideport by other locking arrangements such as a conventional tamper-proof (or childproof) arrangement typically used on pill containers that contain prescription medication which is dispensed by a pharmacy.

While the above-described catheter systems 16, 200, 300, 400, 500, 600, 600' and 600" were described as being placed in the body 46 utilizing the permanent catheterization technique and has many advantages thereby, such catheter systems 16, 200, 300, 400, 500, 600, 600' and 600" could be placed in the body 46 utilizing other techniques (e.g. the temporary catheterization technique) and still achieve some of the advantages of the present invention. Also, while the above described inner catheters 48, 58, 303, 304, 305, 306, 404, 406, 506, 508, 510, 512, 606, 610, were shown as only having a single hole or orifice defined in its distal segment through which fluid may be advanced, it should be appreciated that the distal segment of any of such inner catheters may have two or more holes defined in its distal segment each through which fluid may be advanced. For example, the distal segment of any of such inner catheters may have a single distal end hole (such as the distal orifice 336 of FIG. 17) and four additional holes defined in the sidewall of the distal segment, wherein each of the four additional holes is spaced apart from the distal end hole in the proximal direction by a distance.

There are a plurality of advantages of the present invention arising from the various features of each of the catheter systems described herein. It will be noted that alternative embodiments of each of the catheter systems of the present invention may not include all of the features described yet still benefit from at least some of the advantages of such features. Those of ordinary skill in the art may readily devise their own implementations of each of the catheter systems that incorporate one or more of the features of the present invention and fall within the spirit and scope of the present invention as defined by the appended claims.

What is claimed is:

1. A catheter system for use in a body of a patient, comprising:

a guide catheter having a distal guide orifice, a proximal guide orifice, and a guide lumen extending therebetween;

an original catheter positionable within said guide lumen of said guide catheter, wherein said original catheter has an original lumen and an original distal orifice;

a replacement catheter positionable within said guide lumen of said guide catheter, wherein said replacement catheter has a replacement lumen and a replacement distal orifice; and a closure member securable to said guide catheter so as to cover said proximal guide orifice, wherein said original distal orifice is positioned on an original distal segment of said original catheter which extends out of said distal guide orifice of said guide catheter when said original catheter is positioned within said guide lumen of said guide catheter, and wherein said replacement distal orifice is positioned on a replacement distal segment of said replacement catheter which extends out of said distal guide orifice of said guide catheter when said replacement catheter is positioned within said guide lumen of said guide catheter.

2. The catheter system of claim 1, wherein:

said closure member has internal threads defined thereon, said guide catheter has external threads defined thereon adjacent to said proximal guide orifice, and said internal threads cooperate with said external threads so as to lock said closure member to said guide catheter.

3. The catheter system of claim 1, wherein:

said guide catheter includes a first locking component, and said original catheter includes a second locking component which cooperates with said first locking component to lock said original catheter to said guide catheter.

4. The catheter system of claim 3, wherein said replacement catheter includes a third locking component which cooperates with said first locking component to lock said replacement catheter to said guide catheter.

5. The catheter system of claim 4, wherein said closure member includes a fourth locking component which cooperates with said first locking component to lock said closure member to said guide catheter.

6. The catheter system of claim 1, wherein said guide catheter includes a blood flow valve configured to restrict blood and air flow through said guide lumen of said guide catheter when neither said original catheter nor said replacement catheter is located within said guide lumen of said guide catheter.

7. The catheter system of claim 1, further comprising a tissue ingrowth member secured to an outer surface of said guide catheter and configured to facilitate fibrous tissue growth therein, whereby subcutaneous tissue of said body becomes affixed to said tissue ingrowth member when said tissue ingrowth member remains in contact with said subcutaneous tissue over a period of time.

8. The catheter system of claim 1, wherein a distal portion of said guide lumen possesses a split-tip configuration.

9. The catheter system of claim 1, wherein a distal portion of said original catheter possesses a split-tip configuration.

10. The catheter system of claim 1, wherein:

said guide catheter includes a sideport, said sideport includes a conduit which defines a sideport lumen, and said sideport lumen is in fluid communication with said guide lumen.

11. A method of performing a medical procedure with a catheter system which includes (i) a guide catheter having a distal guide orifice, a proximal guide orifice, and a guide lumen extending therebetween, and (ii) an original catheter having an original distal orifice, comprising the steps of:

positioning the guide catheter within a body of a patient;

positioning the original catheter within the guide catheter, while the guide catheter is positioned within the body, so that the original distal orifice is advanced through the guide lumen and out of the distal guide orifice, whereby the original distal orifice is positioned outside of the guide lumen;

performing a first medical procedure on the patient using the original catheter while the original catheter is positioned within the guide catheter and the original distal orifice is positioned outside of the guide lumen;

removing the original catheter from the guide lumen of the guide catheter after the first medical procedure performing step; and attaching a first closure member to the guide catheter so that the first closure member covers the proximal guide orifice of the guide catheter after the original catheter removing step and while the guide catheter is positioned within the body.

12. The method of claim 11, wherein the catheter system further includes a replacement catheter having a replacement distal orifice, further comprising the steps of:

detaching the first closure member from the guide catheter after the first closure member securing step;

positioning the replacement catheter within the guide catheter, while the guide catheter is positioned within the body, so that the replacement distal orifice is advanced through the guide lumen and out of the distal guide orifice, whereby the replacement distal orifice is positioned outside of the guide lumen; and performing a second medical procedure on the patient using the replacement catheter while the replacement catheter is positioned within the guide catheter and the replacement distal orifice is positioned outside of the guide lumen.

13. The method of claim 11, wherein (i) the guide catheter has a tissue ingrowth member secured thereto, and (ii) the guide catheter positioning step includes the step of advancing the guide catheter into the body so that the tissue ingrowth member is positioned in subcutaneous tissue of the body, further comprising the step of:

leaving the guide catheter within the body for a period of time sufficient to cause the subcutaneous tissue to become affixed to the tissue ingrowth member.

14. The method of claim 11, wherein the first medical procedure is selected from the following group: a hemodialysis procedure, a peritoneal dialysis procedure, a plasmapheresis procedure, a TPN administration procedure, a medicinal infusion procedure, a blood transfusion procedure, and a blood sampling procedure.

15. The method of claim 14, wherein the first medical procedure is the same type of medical procedure as the second medical procedure.

16. The method of claim 11, wherein the guide catheter further has a sideport, further comprising the step of:

advancing a fluid into the sideport so that the fluid is advanced into the guide lumen and out of the distal guide orifice whereby the guide lumen is flushed by the fluid.

17. The method of claim 16, wherein (i) the sideport includes a conduit which defines a sideport lumen, (ii) the sideport lumen is in fluid communication with the guide lumen, further comprising the step of:

advancing the fluid into the sideport lumen so that the fluid advances into the guide lumen.

18. The method of claim 16, wherein:

the fluid advancing step is performed while the original catheter is positioned within the guide lumen.

19. The method of claim 18, wherein the fluid advancing step is performed during the first medical procedure performing step.

20. The method of claim 16, wherein the sideport defines a proximal sideport orifice, further comprising the step of attaching a second closure member to the sideport so as to cover the proximal sideport orifice after the fluid advancing step.

* * * * *